US010299692B2

(12) United States Patent
Kalinin et al.

(10) Patent No.: US 10,299,692 B2
(45) Date of Patent: May 28, 2019

(54) SYSTEMS, COMPONENTS, DEVICES AND METHODS FOR CARDIAC MAPPING USING NUMERICAL RECONSTRUCTION OF CARDIAC ACTION POTENTIALS

(71) Applicant: EP Solutions SA, Yverdon-les-Bains (CH)

(72) Inventors: Alexander Kalinin, Korolyov (RU); Vitaly Kalinin, Voronezh (RU); Mikhail Tsiklauri, Moscow (RU); Walther Schulze, Cheyres (CH)

(73) Assignee: EP SOLUTIONS, S.A., Yvderon-les-Bains (CH)

( * ) Notice: Subject to any disclaimer, the term of this patent is extended or adjusted under 35 U.S.C. 154(b) by 223 days.

(21) Appl. No.: 15/143,599

(22) Filed: May 1, 2016

(65) Prior Publication Data
US 2016/0338611 A1    Nov. 24, 2016

Related U.S. Application Data

(60) Provisional application No. 62/161,147, filed on May 13, 2015, provisional application No. 62/161,208, filed on May 13, 2015.

(51) Int. Cl.
*A61B 5/00* (2006.01)
*A61B 5/042* (2006.01)
(Continued)

(52) U.S. Cl.
CPC ......... *A61B 5/0422* (2013.01); *A61B 5/0022* (2013.01); *A61B 5/04012* (2013.01);
(Continued)

(58) Field of Classification Search
CPC .............................. A61B 5/0422; G16H 50/50
(Continued)

(56) References Cited

U.S. PATENT DOCUMENTS

| 6,939,309 B1 | 9/2005 | Beatty et al. | |
| 2003/0120163 A1* | 6/2003 | Rudy | A61B 5/0402 600/509 |
| 2014/0235996 A1 | 8/2014 | Kim et al. | |

FOREIGN PATENT DOCUMENTS

WO    WO 2007/134190    11/2007

OTHER PUBLICATIONS

Zsolt Badics et al: "Real-time reconstruction of endocardial potential maps in non-contact cardiac mapping", Compel: The International Journal for Computation and Mathematics in Electrical and Electronic Engineering, vol. 28, No. 4, Jul. 10, 2009 (Jul. 10, 2009), pp. 865-878, XP055306237, GB ISSN: 0332-1649, DOI: 10.1108/03321640910958973 * the whole document*.
(Continued)

*Primary Examiner* — Nadia A Mahmood
(74) *Attorney, Agent, or Firm* — Leason Ellis LLP

(57) ABSTRACT

Disclosed are various embodiments of invasive and non-invasive systems for electrophysiological mapping of a patient's heart, where cardiac action potentials (APs) on a myocardial surface of a human heart are reconstructed. In one embodiment, the APs are reconstructed using known electrical potentials on the myocardial surface in combination with known geometries of the heart and/or the torso. A mathematical model of cardiac electrical activity may be employed that takes into account homogeneous and isotropic intracellular, extracellular, and human body electrical conductivities.

24 Claims, 31 Drawing Sheets
(7 of 31 Drawing Sheet(s) Filed in Color)

(51) Int. Cl.
| | |
|---|---|
| *A61B 5/04* | (2006.01) |
| *A61B 5/055* | (2006.01) |
| *A61B 6/03* | (2006.01) |
| *A61B 5/0408* | (2006.01) |
| *A61B 5/0452* | (2006.01) |
| *G16H 50/50* | (2018.01) |
| *G06F 19/00* | (2018.01) |

(52) U.S. Cl.
CPC ........ *A61B 5/0452* (2013.01); *A61B 5/04085* (2013.01); *A61B 5/055* (2013.01); *A61B 5/6805* (2013.01); *A61B 5/6853* (2013.01); *A61B 5/7425* (2013.01); *A61B 6/03* (2013.01); *G06F 19/00* (2013.01); *G16H 50/50* (2018.01); *A61B 5/7239* (2013.01); *A61B 5/7242* (2013.01)

(58) Field of Classification Search
USPC .......................................................... 600/509
See application file for complete search history.

(56) References Cited

OTHER PUBLICATIONS

Chengzong Han et al: "Noninvasive Three-Dimensional Cardiac Activation Imaging From Body Surface Potential Maps: A Computational and Experimental Study on a Rabbit Model", IEEE Transactions on Medical Imaging, IEEE Service Center, Piscataway, NJ, US, vol. 27, No. 11, Nov. 1, 2008 (Nov. 1, 2008), pp. 1622-1630, XP011232592, ISSN: 0278-0062, DOI: 10.1109/TMI.2008.929094 * the whole document *.

* cited by examiner

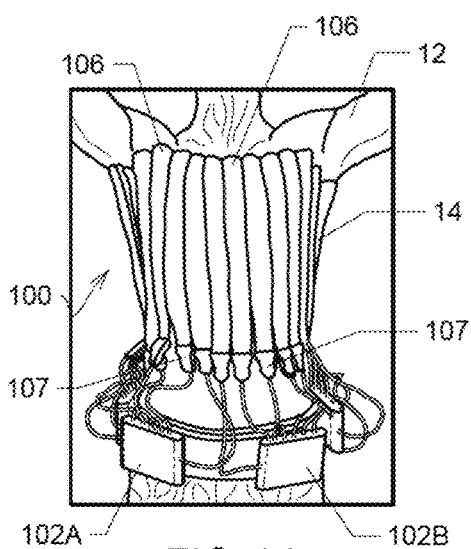
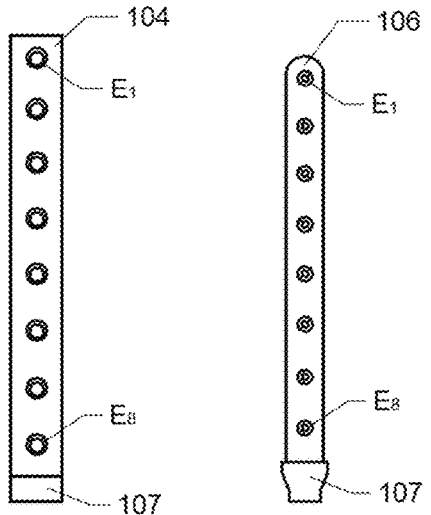
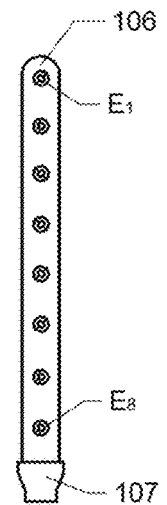
FIG. 3A  FIG. 3B  FIG. 3C
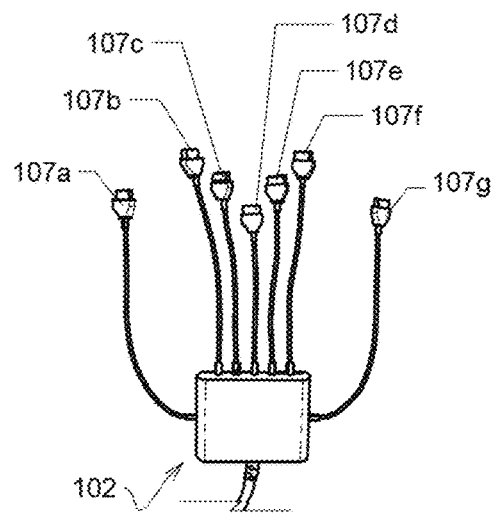
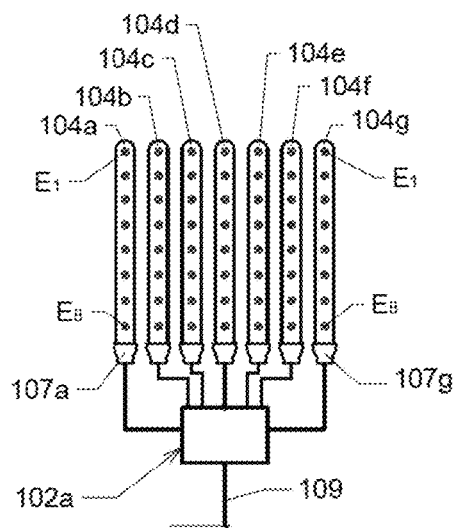
FIG. 3D  FIG. 3E

SYSTEMS, COMPONENTS, DEVICES AND METHODS FOR CARDIAC MAPPING USING NUMERICAL RECONSTRUCTION OF CARDIAC ACTION POTENTIALS

RELATED APPLICATIONS

This application claims priority and other benefits from: (a) U.S. Provisional Patent Application Ser. No. 62/161,147 entitled "Systems and Methods for Noninvasive Cardiac Mapping Using Reconstruction of Action Potentials" to Kalinin et al. filed May 13, 2015, and (b) U.S. Provisional Patent Application Ser. No. 62/161,208 entitled "Systems and Methods for Noninvasive Cardiac Mapping Using a Mathematical Model of the Spread of Cardiac Excitation" to Kalinin et al. filed May 13, 2015, which are both hereby incorporated by reference in their respective entireties. This application also incorporates by reference in their respective entireties: (a) U.S. patent application Ser. No. 15/143,610, filed on May 1, 2016 entitled "Customizable Electrophysiological Mapping Electrode Patch Systems, Devices, Components and Methods" to Cailler et al. (hereafter "the '610 application to Cailler"), and (b) U.S. patent application Ser. No. 15/143,603, filed on May 1, 2016 entitled "Combined Electrophysiological Mapping and Cardiac Ablation Methods, Systems, Components and Devices" to Stroebel et al. (hereafter "the '603 application to Stroebel").

FIELD OF THE INVENTION

Various embodiments disclosed and described herein relate generally to systems and methods for cardiac electrophysiology imaging and measurements. More particularly, the various embodiments disclosed and described herein relate to systems and methods for noninvasive and/or invasive imaging of cardiac electrical activity using numerical reconstruction of cardiac action potentials.

BACKGROUND

Heart rhythm disorders are of great clinical significance. Imaging of cardiac electrical activity has important value in the investigation of underlying mechanisms of cardiac arrhythmias and their treatment, including interventional and surgical approaches. At the same time, imaging of electrical activity of the heart is challenging because cardiac electrical activity is time dependent and spatially distributed throughout the myocardium.

Conventional electrocardiographic methods, such as conventional 12-lead ECG, vectorcardiography and multichannel body surface ECG mapping techniques can be limited in their ability to provide information regarding regional electrical activity in the myocardium. Recording of local electrograms (EGs) on the epicardial and endocardial surfaces of the heart utilizing specialized recording devices such as intracardiac catheters or numerical reconstruction of the local EGs using body surface mapping data can provide more accurate cardiac electrical activity data.

Cardiac imaging using local electrograms suffers from several disadvantages, however. It is well known that local electrograms have two components—the "near field" reflecting local electrical activity of the myocardium, and the "far field" reflecting electrical activity of the entire myocardium. The presence of the far field component in electrograms complicates electrophysiological analysis, as electrograms do not show directly moments of activation and recovery of the myocardium. To map activation, common approaches include the use of empirical algorithms for electrogram processing (such as −du/dt max). However, such methods are typically not suitable for mapping reentrant arrhythmias (such as atrial and ventricular fibrillation, or polymorphic ventricular tachycardia) because local electrograms are often fractionated. Even greater difficulties can arise in detecting repolarization sequences of the myocardium.

Unlike electrograms, action potentials are signals that reflect intracellular myocardial electrical activity. Action potential signals, if they can be obtained or derived, permit activation and recovery times to be determined. Moreover, action potential signals (or "action potentials") directly reflect cellular ionic currents. Consequently, action potentials permit the locations of cellular substrate of cardiac arrhythmias to be determined. Unfortunately, acquisition and/or derivation of action potential signals has proven to be notoriously difficult.

What is needed are improved methods and means of determining action potentials.

SUMMARY

In a first embodiment, there is provided an electrophysiological mapping system (EMS) configured to reconstruct myocardial surface action potentials (APs) corresponding to a patient's heart. The EMS comprises: (a) a plurality of electrical sensing electrodes configured to acquire cardiac electrical signals from at least portions of at least one of the patient's torso and the patient's heart; (b) a data acquisition device operably connected to the electrical sensing electrodes and configured to condition the cardiac electrical signals provided thereby; (c) an imaging system configured to generate patient geometry data, and (d) at least one non-transitory computer readable medium storing instructions executable by at least one processor configured to perform a method for receiving and processing the cardiac electrical signals and the patient geometry data to reconstruct the APs on a myocardial surface associated with the patient's heart. The method carried out by the at least one non-transitory computer readable medium storing instructions executable by at least one processor comprises: (i) calculating a geometric model of at least one of portions of the patient's torso and portions of the patient's heart; (ii) assigning electrical conductivity coefficients of at least one of the patient's torso and at least portions of the patient's myocardium to the calculated geometric model; (iii) using the cardiac electrical signals, the geometric model, and the electrical conductivity coefficients as inputs, calculating reconstructed electrical potential values and co-normal derivative values associated with the myocardial surface; (iv) using the reconstructed electrical potential values and co-normal derivative values, calculating harmonic function values in a myocardial domain by numerically solving the Neumann problem for the Laplace equation; and (v) using the harmonic function values, the reconstructed electrical potential values, and the electrical conductivity coefficients as inputs, calculating, for at least portions of the myocardial surface, reconstructed action potential values representative of the APs.

The first embodiment may further comprise any one or more of: (a) electrical conductivity coefficients corresponding to myocardial extracellular and intracellular media; (b) action potential values obtained by subtracting the electrical potential values from the harmonic function values, and dividing the results by a coefficient which is ratio of the values of the electrical conductivity coefficients; (c) at least some of the cardiac electrical signals being provided by surface electrodes configured to provide ECGs; (d) at least some of the cardiac electrical signals being provided by electrodes forming a portion of an EP catheter; (e) an EP catheter comprising a balloon and non-contact electrodes configured to float within the patient's blood within the patient's heart; (f) reconstructed action potential values calculated using the geometry of the heart only; (g) reconstructed action potential values calculated numerically using a boundary element method; (h) reconstructed action potential values calculated numerically using a finite element method; (i) the imaging system comprising a CT, MRI or MRT; (j) reconstructed action potential values being calibrated and adjusted according to a determined resting potential of the patient's myocardium.; (k) reconstructing a sequence of cardiac activation and recovery by calculating a gradient on the myocardial surface corresponding to the reconstructed action potential values; (l) identifying regions of myocardial fibrosis in the patient's heart in which magnitudes of the reconstructed action potential values fall below a predetermined threshold.

In a second embodiment, there is provided a method of reconstructing myocardial surface action potentials (APs) corresponding to a patient's heart. The method comprises: (a) acquiring a plurality of cardiac electrical signals from at least portions of at least one of the patient's torso and the patient's heart; (b) acquiring patient geometry data from the patient; (c) calculating a geometric model of at least one of portions of the patient's torso and portions of the patient's heart; (d) assigning electrical conductivity coefficients of at least one of the patient's torso and at least portions of the patient's myocardium to the calculated geometric model; (e) using the cardiac electrical signals, the geometric model, and the electrical conductivity coefficients as inputs, calculating reconstructed electrical potential values and co-normal derivative values associated with the myocardial surface; (f) using the reconstructed electrical potential values and co-normal derivative values, calculating harmonic function values in a myocardial domain by numerically solving the Neumann problem for the Laplace equation, and (g) using the harmonic function values, the reconstructed electrical potential values, and the electrical conductivity coefficients as inputs, calculating, for at least portions of the myocardial surface, reconstructed action potential values representative of the APs.

The second embodiment may further comprise any one or more of: (a) providing at least some of the cardiac electrical signals using surface electrodes configured to provide ECGs; (b) providing at least some of the cardiac electrical signals using electrodes forming a portion of an EP catheter; (c) an EP catheter comprising a balloon and at least some non-contact electrodes configured to float within the patient's blood and heart; (d) calculating reconstructed action potential values using the geometry of the heart only; (e) calculating the reconstructed action potential values numerically using a boundary element method; (f) calculating the reconstructed action potential values numerically using the finite element method; (g) the imaging system comprises a CT, MRI or MRT; (h) calibrating and adjusting the reconstructed action potential values according to a determined resting potential of the patient's myocardium; (i) calculating a sequence of cardiac activation and recovery by calculating a gradient on the myocardial surface corresponding to the reconstructed action potential values, and (j) identifying regions of myocardial fibrosis in the patient's heart in which magnitudes of the reconstructed action potential values fall below a predetermined threshold.

Further embodiments are disclosed herein or will become apparent to those skilled in the art after having read and understood the specification and drawings hereof.

BRIEF DESCRIPTION OF THE DRAWINGS

This patent or application file contains at least one drawing executed in color. Copies of this patent or patent application publication with color drawing(s) will be provided by the Office upon request and payment of the necessary fee. Different aspects of the various embodiments will become apparent from the following specification, drawings and claims in which:

FIGS. 3A through 3E show various devices and components associated with one embodiment of mapping electrode system 100;

The drawings are not necessarily to scale. Like numbers refer to like parts or steps throughout the drawings.

DETAILED DESCRIPTIONS OF SOME EMBODIMENTS

Described herein are various embodiments of systems, devices, components and methods for obtaining action potentials of a patient's heart.

At least portions or components of the EP Solutions 01C System for Non-Invasive Cardiac Electrophysiology Studies (which is based upon and in most aspects the same as the AMYCARD 01 C System for Non-Invasive Cardiac Electrophysiology Studies) may be adapted for use in conjunction with the various embodiments described and disclosed herein. Portions of the EP Solutions 01C System (hereafter "the EP Solutions 01C System") and other relevant components, devices and methods are described in: (a) U.S. Pat. No. 8,388,547 to Revishvili et al. entitled "Method of Noninvasive Electrophysiological Study of the Heart" ("the '547 patent"); (b) U.S. Pat. No. 8,529,461 to Revishvili et al. entitled "Method of Noninvasive Electrophysiological Study of the Heart" ("the '461 patent"), and (c) U.S. Pat. No. 8,660,639 to Revishvili et al. entitled "Method of Noninvasive Electrophysiological Study of the Heart" ("the '639 patent"). The '547 patent, the '461 patent, and the '639 patent are hereby incorporated by reference herein, each in its respective entirety.

Figure 1:
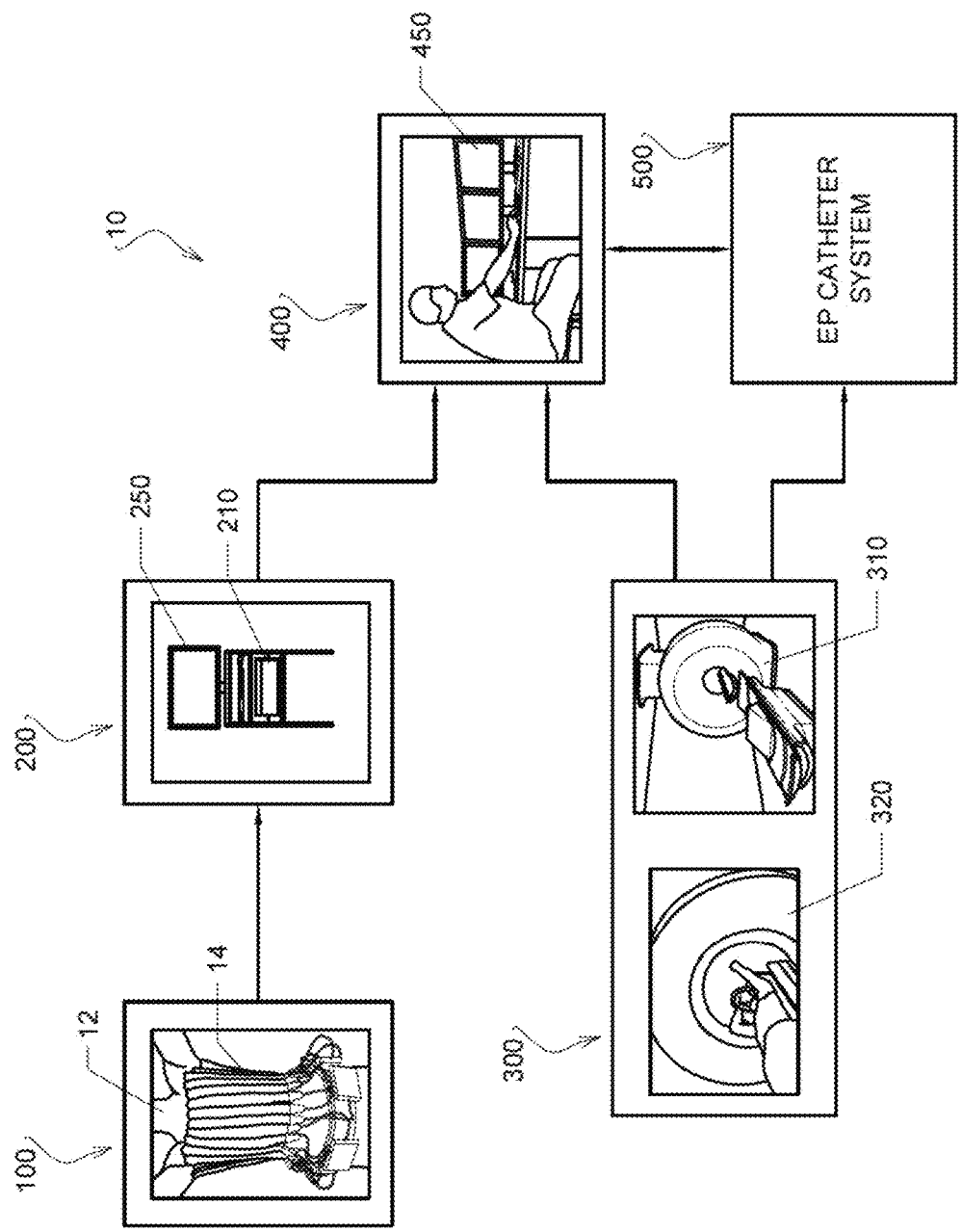
FIG. 1 shows one embodiment of a basic method and system 10 for non-invasive electrophysiological mapping of a patient's heart activity.

Referring now to FIG. 1, there is shown one embodiment of a basic method and system 10 for non-invasive electrophysiological mapping of a patient's heart activity. As shown, electrophysiological mapping system 10 ("EPM 10") comprises four basic sub-systems: (a) mapping electrode system 100 ("MES 100") disposed on patient 12's torso 14; (b) multichannel mapping unit 200 ("MMU 200"), which in one embodiment comprises a data acquisition device 210 and a corresponding first computer or computer workstation 250 for multichannel mapping of the heart; (c) scanner or imaging device 300, which in one embodiment is a computed tomography scanner 310 or an MRI scanner 320 (although other suitable types of medical imaging devices and systems may also be used, such as X-ray fluoroscopy); (d) processing and visualization module 400 ("PVM 400"), which in one embodiment comprises a second computer or computer workstation 450, and, in some embodiments, (e) electrophysiological catheter mapping system 500 ("EP catheter system"), which may comprise a third computer or computer workstation 550. (Note that in some embodiments the first computer 250 of MMU 200, the second computer 450 of PVM 400, and even third computer 550 may be combined into a single computer or computer workstation, may comprise more than three computers or computer workstations, and/or may include computing and processing capability and/or storage provided by a network of local or remote computers, servers, and/or the cloud.)

In one embodiment, MES 100 comprises a plurality of electrical sensing electrodes $E_1 \ldots E_n$ positioned on torso 14 of patient 12 (and in some embodiments on other portions of patient 12's body). Sensing electrodes in MES 100 are configured to sense electrical activity originating in patient 12's body. In addition to electrical sensing electrodes, other types of devices and/or transducers, such as ground electrodes, high intensity focused ultrasound transducers, ultrasound probes, navigation patches, cardioversion patches, and the like (more about which is said below), may be configured to operate in conjunction with, be incorporated into, or form a portion of MES 100 and/or system 10.

In one embodiment, and by way of non-limiting illustrative example, MES 100 comprises one or more of an ECG cable with 12 leads and corresponding electrodes, an ECG cable with 4 leads and corresponding electrodes, a patient cable for ECG-mapping with 8 contacts or electrodes, one or more special ECG-mapping cables (each with, for example, 56 contacts or electrodes), and special disposable or reusable mapping electrodes, each strip of disposable or reusable mapping electrodes having 8 contacts or electrodes. One example of a disposable ECG electrode is Model No. DE-CT manufactured by EP Solutions SA, Rue Galilee 7, CH-1400 Yverdon-les-Bains. Many different permutations and combinations of MES system 100 are contemplated having, for example, reduced, additional or different numbers of electrical sensing and other types of electrodes, sensors and/or transducers.

In one embodiment, MES 100 further comprises or operates in conjunction with one or more catheters and associated electrodes, sensors and/or transducers associated with invasively conducting electrophysiological studies/mapping using EP catheter system 500. EP catheter system 500 may comprise one or more EP catheters comprising floating, basket or other types of electrodes known to those skilled in the art that are configured to measure electrical signals from patient's heart 16.

Figure 2:
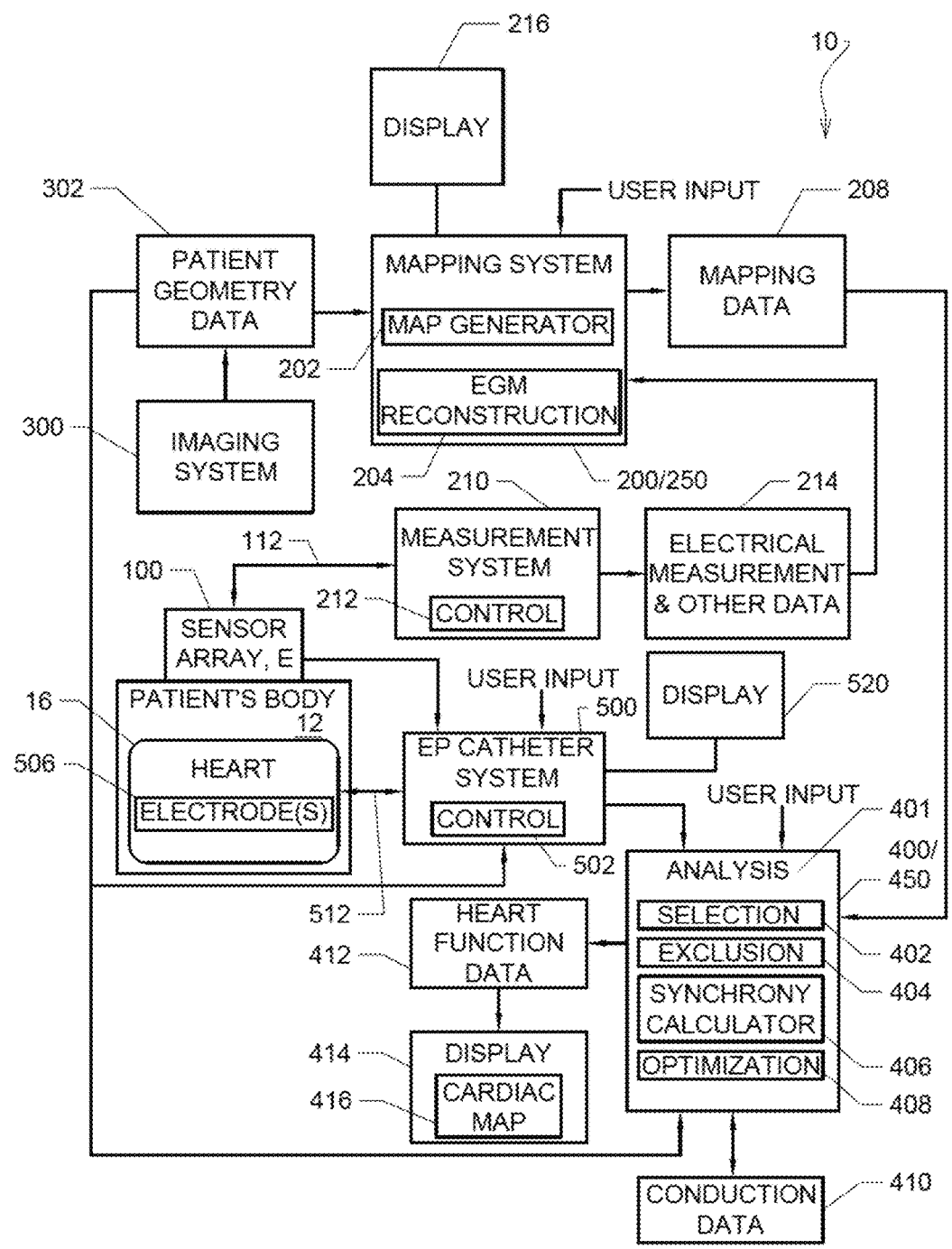
FIG. 2 shows a schematic block diagram of one embodiment of system 10 that can be utilized for assessing the electrophysiological function of a patient's heart.

Scanner or imaging system 300 is used to help identify and determine the precise positions of the various electrodes included in MES 100 that have been placed in various positions and locations on patient 12's body, and is configured to provide patient geometry data 302 (see, for example, FIG. 2). Surface electrodes or position markers located on the patient's torso or in other locations on the patient's body can be configured to act as fiducial markers for imaging system 300.

In some embodiments, or in addition, electrodes, sensors and/or transducers associated with EP catheter system 500 are configured to provide inputs to a navigation or position/location determination system or device so that the spatial position of the EP catheter(s) within or on the heart may be determined. One catheter navigation system is described in U.S. Pat. No. 6,947,788 entitled "Navigable catheter" to Gilboa et al., the entirety of which is hereby incorporated by reference herein, and which describes receiving and transmitting coils disposed in a catheter, and which permits the position of the catheter in a patient's body to be determined. The frequencies of transmitting and/or receiving coils or antennae in a catheter can be configured to operate outside the range of the frequencies of heart electrical signals to avoid or reduce the possibility of interference therewith (e.g., greater than 500 or 1,000 Hz).

Referring now to FIGS. 1 and 2, ECG data and/or other potential signals are acquired from MES 100 by MMU 200, which in one embodiment comprises a data acquisition device or measurement system 210 that filters and amplifies analog signals provided by MES 100, digitizes such analog signals using one or more analog-to-digital converters ("ADCs") and associated processors or microprocessors, and sends or relays, or otherwise transfers or has transferred, the amplified and digitized signals to first computer or computer workstation 250. In one embodiment, data acquisition device 210 permits multichannel synchronous EKG/ECG and/or other potential signals recording from, by way of example, 240 or more surface electrodes positioned on a patient's skin and torso, as well as multichannel synchronous EKG/ECG and/or other potential signals recording from additional or other electrodes or channels (as described above in connection with MES 100).

In one embodiment, first computer or computer workstation 250 stores or records the amplified and digitized signals provided by data acquisition device 210. Signal digitization and recording functions can also be apportioned or split between data acquisition device 210 and first computer or computer workstation 250. Data from scanner or imaging system 300 and ECG data sensed by MES 100 and acquired and recorded by MMU 200 are then both input into PVM 400. In one embodiment, ECG data from patient 12 are acquired using MES 100 and data acquisition device 210 from unipolar electrodes positioned on patient's torso 14. The precise locations of such electrodes on patient's torso 14 are determined in PVM 400 using patient geometry data 302 provided by scanner or imaging system 300. (In other embodiments, patient geometry data 302 are calculated using input data from imaging system 300, in MMU 200, PVM 400, and/or EP catheter system 500. In still other embodiments, patient geometry data are provided to one or more of any of MMU 200, PVM 400 and EP catheter system 500. ECG data and/or other potential signals data recorded by MMU 200 may be stored on a CD, a USB memory stick, in RAM, on an electronic storage device such as a hard or flash drive, or in another memory device or component, and may then be exported or transferred to PVM 400 using such a storage device. Alternatively, ECG data recorded by MMU 200 may be transferred to PVM, by way of non-limiting illustrative example, using a local area network (LAN), a wide area network (WAN), wireless communication means (e.g., using Bluetooth or the Medical Implant Communication System or MICS), the internet or the cloud, or by suitable computer communication means known to those skilled in the art. In PVM 400, computed tomography of the chest and heart area is carried out, and processing and analysis of multichannel ECG data and computed tomography data are executed.

By way of non-limiting illustrative example, PVM 400 comprises a second computer or computer workstation 450 that comprises a specialized processing and visualization computer or series of interconnected computers or processors, which include pre-loaded and pre-programmed software configured to conduct electrophysiological studies. Second computer or computer workstation 450 typically comprises a keyboard, a mouse, a display 414 (such as a 24" or 25" LCD monitor), and a printer. PVM 400 and second computer or computer workstation 450 are configured for advanced mathematical processing of computed tomographic study data combined with multichannel ECG body surface mapping data, which together make it possible to perform computed non-invasive activation mapping of the patient's heart.

In some embodiments, and as mentioned above, MMU 200 and PVM 400 are combined in a single computing platform or computer workstation, and the functionality provided by the combination of MMU 200 and PVM 400 are combined into and provided by such a single computing platform or computer workstation.

Increased computing performance for such a single computing platform can be provided by multiple processors arranged in parallel and increased RAM and ROM EP catheter system 500 may be configured to operate in conjunction with one or more of MES 100, MMU 200, scanner or imaging system 300 and PVM 400, and permits invasive EP mapping or studies of the patient's heart 16, more about which is said below.

Together, MES 100, MMU 200, scanner 300, PVM 400 and EP catheter system 500 comprise EPM 10, and can include employing a technique known as NIEM (Non-Invasive Electrophysiological Mapping), which is an electrophysiological method based on non-invasive reconstruction of cardiac activation patterns sensed by a dense network of surface electrodes attached to the patient's torso. NIEM is employed in EPM 10 to permit non-invasive numerical reconstruction of endocardial and/or epicardial electrograms originating from the patient's ventricles and/or atria. Mathematical algorithms executed by EPM 10 are applied to the acquired unipolar surface ECG data to permit 3D reconstruction of the patient's heart and thorax. In one embodiment, EP catheter system 500 is employed to map electrical activity of patient's heart in conjunction with MMU 200, scanner 300 and/or PVM 400, without the use of signals obtained from MES 100. In another embodiment, MES 100 is employed to map electrical activity of patient's heart in conjunction with MMU 200, scanner 300 and/or PVM 400, without the use of signals obtained from EP catheter system 500. In still another embodiment, data obtained using both MES 100 and EP catheter system 500 are combined and processed using MMU 200, scanner 300 and/or PVM 400.

In one embodiment, EPM 10 reconstructs electrograms using advanced tomographic techniques that eliminate the need to perform invasive surgical procedures on the patient's body, such as described in the '547 patent, the '461 patent, and the '639 patent incorporated by reference herein above. Based on surface electrograms acquired on the patient's torso, time-varying electric field potentials of the patient's heart are calculated using tomographic techniques and algorithms. Actual boundaries of the patient's chest and lung surfaces, and of the patient's epicardial and endocardial heart surfaces, are determined by solving differential equation systems. Continuations of electric field potentials throughout the patient's chest surfaces and back to the patient's epicardial heart surfaces are implemented computationally based on a solution of the Cauchy problem for the Laplace equation in an inhomogeneous medium. When solving the Cauchy problem using the Laplace equation, a model of the chest is employed having tissues that lie within the bounds of large anatomic structures (e.g., the lungs, mediastinum, and/or spine), and that have constant coefficients of electrical conductivity. Heart electric field potentials are assigned harmonic functions in each region, where each region has a constant coefficient of electrical conductivity and satisfies conjugate conditions at the region's borders for electrical potential and current.

FIG. 2 depicts in further detail one embodiment of a system 10 that can be utilized for assessing electrophysiologically the function of a patient's heart 16. System 10 can perform electrophysiological assessment of heart 16 in real time or near-real time as part of a diagnostic procedure and/or mapping procedure. As described above, electrophysiological assessment may be accomplished using either MES 100 or EP catheter system 500, and/or some combination of systems 100 and 500.

EP catheter system 500 provides the capability to acquire electrical signals originating in patient's heart 16 by invasive means. EP catheter system 500 may include control circuitry, a computer and/or a controller 502 that can control the acquisition, processing and/or storage of electrical signals obtained from catheter 512. Control system 502 may be configured to control electrical sensing and stimulation parameters (e.g., current, voltage, impedance, temperature, repetition rate, trigger delay, sensing trigger amplitude) for applying electrical stimulation or for sensing electrical, temperature, impedance or other signals, via the electrode(s) incorporated into catheter 512. One or more sensors (e.g., sensor array of MES 100) and imaging system 300 (and patient geometry data 302) can also communicate sensor, navigational, or positional information to EP catheter system 500, which is located external to the patient's body 12. In one embodiment, the position of EP catheter 512 and its electrodes inside or outside the patient's heart can be determined and tracked via an imaging modality (e.g., any combination of MMU 200, PVM 400 and/or EP catheter system 500 working in combination with scanner or imaging system and patient geometry data 302), direct vision or the like. The location of EP catheter 512 and/or its electrode(s) can be combined to provide corresponding mapping information and data.

Concurrently with, or before or after, acquiring data using EP catheter system 500, MES 100 of system 10 may be utilized to acquire electrophysiological information from the patient. In the example of FIG. 2, MES 100 comprising multiple surface electrodes is utilized to record patient electrophysiological activity. As described above, additional electrophysiological data may be acquired using electrical sensing/navigational/positional electrodes, coils or sensors incorporated into EP catheter system 500.

Alternatively or additionally, in other embodiments, MES 100 and/or EP catheter system 500 can comprise one or more invasive sensors, such as EP catheter 512 having a plurality of electrodes. EP catheter 512 can be inserted into the patient's body 12 and into heart 16 for mapping electrical activity for an endocardial surface, such as the wall of a heart chamber. In one embodiment, EP catheter 512 can be a non-contact mapping catheter or a contact mapping catheter. In another embodiment, MES 100 can comprise an arrangement of sensing electrodes disposed on devices such as patches, which are placed on or near a patient's heart epicardially. These patches can be utilized during open chest and minimally invasive procedures to record electrical activity.

In each of such example approaches for acquiring patient electrical information, including by invasive or non-invasive means, or by a combination of invasive and non-invasive means, MES 100 and/or EP catheter system 500 provides the sensed electrical information to a corresponding measurement system such as measurement system or data acquisition device 210. The measurement system (e.g., data acquisition device 210) can include appropriate controls and signal acquisition and processing circuitry 212 for providing corresponding measurement or sensor data 214 that describes electrical activity detected by the sensors in MES 100 and/or EP catheter system 500. The measurement data 212 can include analog or digital information.

Data acquisition device or measurement system 210 can also be configured to control the data acquisition process for measuring electrical activity and providing the measurement data. The measurement data 214 can be acquired concurrently with, or in addition to, the acquisition of data from EP catheter system 500, such as to detect electrical activity of the heart 16 that occurs in response to applying a stimulation pulse to the patient's heart 16 using EP catheter 512. For instance, appropriate time stamps can be utilized for indexing the temporal relationship between the respective measurement data 214 and measurement parameters to facilitate the evaluation and analysis thereof.

MMU 200/250 is programmed to combine the measurement data 214 corresponding to electrical activity of heart 16 with patient geometry data 302 derived from scanner/imaging device 300 by applying an appropriate algorithm to provide corresponding electro-anatomical mapping data 208. Mapping data 208 can represent electrical activity of the heart 16, such as corresponding to a plurality of reconstructed electrograms distributed over a cardiac envelope for the patient's heart (e.g., an epicardial envelope). Mapping data 208 may comprise cardiac electrical signals in the form of potential signals. As one example, mapping data 208 can correspond to electrograms for an epicardial or endocardial surface of the patient's heart 16, such as based on electrical data that is acquired non-invasively via sensors distributed on the body surface or invasively with sensors distributed on or near the epicardial or endocardial envelope. Alternatively, mapping data 208 can be reconstructed for an endocardial surface of a patient's heart such as a portion of chambers of the patient's heart (e.g., left and right ventricles, or left and right atria), such as based on electrical activity that is recorded invasively using EP catheter 512 or similar devices or recorded non-invasively via body surface sensors. The mapping data can represent electrical activity for other cardiac envelopes. The particular methods employed by the MMU 200/250 for reconstructing the electrogram data or other potential signals can vary depending upon the approach utilized for acquiring the measurement data 214. In addition, and as described further herein, the functionality of MMU 200/250 can be combined with any one or more of PVM 400/450, EP catheter system 500, and scanner or imaging system 300 to provide the data processing, analysis and display of electrophysiological and other data that have been or are being acquired from the patient.

In one example, MMU 200 generates mapping data 208 to represent activation times computed for each of the plurality of points on the surface of or inside the heart from electrograms over a selected cardiac interval (e.g., a selected beat). Since data acquisition device 210, and in some embodiments EP catheter system 500 can measure electrical activity of the heart concurrently or additionally, the resulting electrogram maps and activation maps (e.g., mapping data 208) thus can also represent concurrent data for the heart for analysis to quantify an indication of synchrony. The interval for which the activation times are computed can be selected based on user input. Additionally or alternatively, the selected intervals can be synchronized with the acquisition of electrical signals by the EP catheter system 500.

In the example of FIG. 2, MMU 200 (which includes a mapping system) may comprise map generator 202 that constructs electro-anatomical mapping data by combining measurement data 214 with patient geometry data 302 through an algorithm that reconstructs the electrical activity of the patient's heart 16 onto a representation (e.g., a three-dimensional representation) of the patient's heart 16.

MMU 200 can also include an electrogram reconstruction engine 204 that processes the electrical activity to produce corresponding electrogram data for each of a plurality of identifiable points on the appropriate cardiac envelope (e.g., an epicardial or endocardial surface) of the patient's heart.

As an example, patient geometry data 302 may be in the form of graphical representation of the patient's torso, such as image data acquired from the patient using scanner/imaging device 300. Such image processing can include extraction and segmentation of anatomical features, including one or more organs and other structures, from a digital image set. Additionally, a location for each of the electrodes in sensor array 100 and/or disposed at or near the distal end of EP catheter 512 can be included in the patient geometry data 302, such as by acquiring the image while the electrodes are disposed on or in the patient and identifying the electrode locations in a coordinate system through appropriate extraction and segmentation. The resulting segmented image data can be converted into a two-dimensional or three-dimensional graphical representation that includes a region of interest for the patient.

Alternatively, patient geometry data can correspond to a mathematical model, such as a generic model of a human torso or a model that has been constructed based on image data acquired for the patient's heart 16. Appropriate anatomical or other landmarks, including locations for the electrodes in sensor array 100 and/or EP catheter 512 can be identified in the patient geometry data 302 to facilitate registration of the electrical measurement data 214 and performing an inverse method thereon. The identification of such landmarks can be done manually (e.g., by a person via image editing software) or automatically (e.g., via image processing techniques).

By way of further example, the patient geometry data 302 can be acquired using nearly any imaging modality based on which a corresponding representation can be constructed. Such imaging may be performed concurrently with recording the electrical activity that is utilized to generate the patient measurement data 302 or the imaging can be performed separately (e.g., before the measurement data are acquired).

System 10 further includes PVM 400/450 that is configured and programmed to assess heart function and provide heart function data or visualizations based on the mapping data 208. As described herein, heart function data 412 may be in the form of an index or indices, or may be provided in the form of a two-dimensional or three-dimensional visual representation of the patient's heart's electrical activity. Additionally, and in some embodiments, PVM 400/450 can be configured to communicate with EP catheter system 500 and data acquisition device 210 so as to synchronize and control measurement of electrical activity via sensor array 100 and/or EP catheter system 500. PVM 400 can be configured to compute a plurality of indices or parameters according to different electrical measurement parameters (e.g., locations of sensing electrodes, and/or electrical stimulation parameters) based on the mapping data 208. PVM 400 may also be configured to compute heart histogram data, or to determine a desired (e.g., optimum) set of electrical signal measurement parameters for achieving desired diagnostic results.

In the example of FIG. 2, PVM 400/450 may be configured and programmed to include a selection function 402, an exclusion function 404, a synchrony calculator 406 and an optimization component 408. The selection function 402 can be programmed to select an interval of a heart beat for which the analysis and heart function data will be calculated. The selection function 402 can be automated, such as synchronized to measurement of electrical signals using EP catheter 512 via EP catheter system 500. Alternatively, the selection function 402 can be manual or semiautomatic to permit selection of one or more cardiac intervals.

Exclusion/Inclusion function 404 may be programmed to identify and exclude, or to include, certain areas of the patient's heart from analysis, such as scar or scar formation areas, or certain chambers or other portions of the patient's heart 16. The exclusion or inclusion can be performed based on electrical information, imaging data (e.g., from patient geometry data 302) or both. Exclusion/Inclusion function 404 can be automatic, based on evaluation of the electrical and/or imaging data, or it can be manual or semiautomatic. Each area (if any) identified for exclusion or inclusion can be co-registered with mapping data 208, such that the identified areas are not utilized, or are utilized, as the case may be as part of the calculations for assessing heart function. Alternatively, exclusion/Inclusion function 404 can be utilized to remove or include results.

Synchrony calculator 406 can be programmed to compute one or more indications of synchrony (e.g., in the form of an index) that provides an assessment of heart function as heart function data. For instance, synchrony calculator 188 can be programmed to perform one or more calculations such as computing a heart global synchrony index (GSI), an intraventricular conduction index (ICI), a segmental synchrony index (SSI), and/or a late activation index relating to heart function data 412. Synchrony calculator 406 can further be configured to compute one or more quantitative indications of synchrony based on heart conduction data 412.

Optimization component 408 can be programmed to determine or help determine one or more electrode measurement locations in the patient's heart 16. This may involve positioning one or more stimulation and/or sensing electrodes at test sites and evaluating the synchrony determined by synchrony calculator 406, or by analyzing the electrophysiological results provided by PVM 400/450. Electrodes 506 of EP catheter 512 can be positioned at the location(s) indicated by optimization component 408 based on such an evaluation.

Additionally or alternatively, optimization component 408 can be utilized to determine or help determine one or more electrode measurement parameters, such as analog or digital filter settings (e.g., notch filter settings), amplifier settings, and/or which electrodes of EP catheter 512 should or should not be used to sense electrical signals, etc. Those skilled in the art will understand appreciate various approaches that can be utilized to vary the location and/or other electrode measurement parameters to achieve a desired diagnostic result.

Heart function data 412 can be utilized to present an indication of heart function on display 414, which can be configured to display text and/or two- or three-dimensional graphics. For instance, the indication of heart function for each set of parameters can be provided as a graphical element that is superimposed onto a cardiac map visualized on display 414 or another display. It is to be understood and appreciated that the determination of the heart function data 412 can be performed in real time or near-real time such that the representation of the heart function on the cardiac map can provide real time guidance and information to facilitate the location and other parameters of the sensors in MES 100 and/or EP catheter 512. The sensor/electrode measurement parameters can also be provided on display 412 or another display such as display 520.

FIGS. 3A through 3E show various devices and components associated with one embodiment of MES or sensor array 100.

FIG. 3A shows a front view of patient 12 having strips of electrodes affixed to flat patient cables 106, where flat patient cables 106 are attached or adhered to patient's torso 14, for example by means of a biocompatible adhesive disposed on the lower surfaces of cables 106, where the adhesive is configured to permit easy removal of cables 106 from patient's torso 14 after the electrophysiological mapping procedure has been completed. In one embodiment, flat patient cables 106 (or disposable electrode strips 104—see FIG. 3B) comprise 8 electrodes $E_1$ through $E_8$ each, and six flat patient cables 106 or disposable electrode strips 104 attached to each ECG mapping cable 102 by means of mapping cable electrode connectors 107.

FIG. 3B shows one embodiment of a disposable electrode strip 104, which comprises 8 electrodes $E_1$ through $E_8$, and also comprises on its lower surface a biocompatible adhesive that permits easy removal of electrode strip 104 from patient's torso 14 after the electrophysiological mapping procedure has been completed. Disposable electrode strip 104 may also comprise mapping cable electrode connectors 107, or electrical connections may be established directly to each of electrodes $E_1$ through $E_8$ by means of separate electrical connections.

FIG. 3C shows one embodiment of a flat patient cable 106, which comprises 8 electrodes $E_1$ through $E_8$, and also comprises on its lower surface a biocompatible adhesive that permits easy removal of electrode strip 106 from patient's torso 14 after the electrophysiological mapping procedure has been completed. Flat patient cable 106 may also comprise mapping cable electrode connectors 107, or electrical connections may be established directly to each of electrodes $E_1$ through $E_8$ by means of separate electrical connections.

FIG. 3D shows one embodiment of an ECG mapping cable 102, which is configured to permit operable electrical connection thereto of seven separate disposable electrode strips 104 or seven flat patient cables 106 via mapping cable electrode connectors 107a through 107g. Mapping cable data acquisition module connectors 109 of ECG mapping cable 102 are configured for attachment to corresponding electrical connectors disposed in data acquisition device 210.

FIG. 3E shows one embodiment of an ECG mapping cable 102 operably connected to seven separate disposable electrode strips 104 or seven flat patient cables 106, each containing 8 electrodes $E_1$ through $E_8$ via mapping cable electrode connectors 107a through 107g.

Referring now to FIGS. 3A through 3E, it will be seen that measurements and sensing of a patient's body surface potentials may be carried out using various electrode configurations. In one embodiment, patient cables 107 with 8 channels each are employed for such measurements and sensing. Patient cables 107 may be attached with snaps to disposable electrode strips with 8 electrodes each see FIGS. 3B and 3C). In one embodiment, up to 7 patient cables may be connected to each of 4 ECG mapping cables 102. Such a configuration provides up to 224 electrodes E. See, for example, FIG. 32A, which does not show 2 additional mapping cables 102 and corresponding patient cables 107 and flat patient cables 106 or disposable electrode strips 104 and, which are applied to patient's torso 14 for multichannel ECG recording.

In addition, and by way of non-limiting illustrative example, additional electrodes and electrode cables may also be affixed to patient's torso 14 to record, for example, surface electrode channels N, R, L, F, V1, V2, V3, V4, V5 and V6, as is well known in the art, and which are used to produce standard 12-lead ECG surface electrode recordings (namely, 6 extremity leads and 6 precordial leads representing extremity lead I (from the right to the left arm), lead II (from the right arm to the left leg), lead III (from the left arm to the left leg), AVL (points to the left arm), AVR (points to the right arm), and AVF (points to the feet) and precordial, or chest leads, V1,V2,V3,V4,V5 and V6 to observe the depolarization wave in the frontal plane.

Figure 4C:
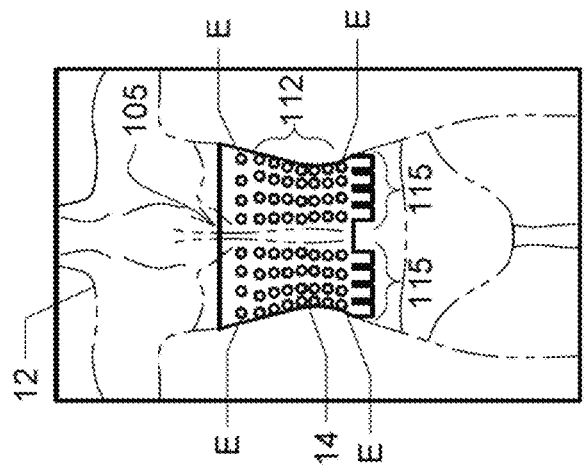
FIGS. 4A through 4C show embodiments of electrophysiological mapping sensor patches.
Figure 4B:
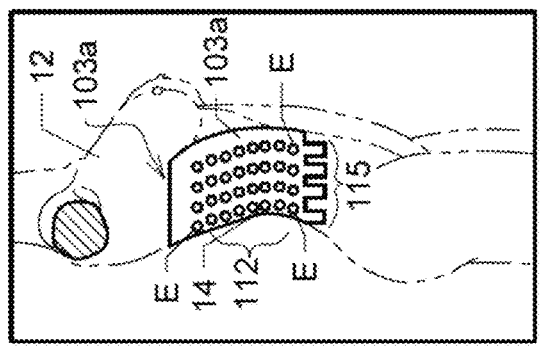
Figure 4A:
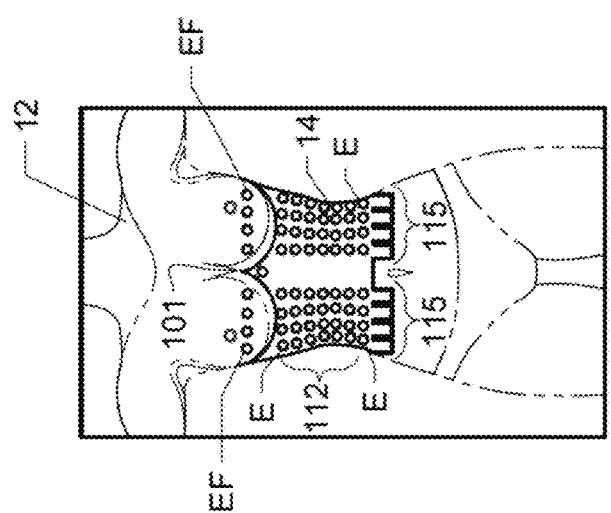

Referring now to FIGS. 4A though 4C, there are shown some embodiments of customizable patches 101, 103 and 105 that can be used to simplify and speed up accurate placement of ECG electrodes on patient's torso 14. Some embodiments of patches 101, 103 and 105 permit body surface ECG signal acquisition to be performed quickly and easily, and also to be combined quickly and easily with non-invasive mapping and navigation tools. As will become apparent to those skilled in the art upon having read and understood the present specification and claims, patches 101, 103 105 increase the efficiency and reduce the time required to carry out electrophysiological studies and mapping, increase patient comfort, are easily adaptable to changes in patient morphology, reduce ECG sensor noise, and may be combined easily with at least some other medical sensing and treatment procedures. The '610 application to Cailler further describes and discloses details concerning patches 101, 103 and 105, the entirety of which is hereby incorporated by reference herein.

Continuing to refer to FIGS. 4A through 4C, there are shown, respectively, embodiments of customizable electrophysiological mapping sensor front patch 101, one embodiment of customizable electrophysiological mapping sensor side patch 103a, and one embodiment of customizable electrophysiological mapping sensor back patch 105 mounted on, adhered or otherwise affixed to torso 14 of patient 12. As shown in FIGS. 4A through 4C, each of patches 101, 103a and 105 comprises a plurality of sensing electrodes E, which in one embodiment are unipolar electrodes integrated into a fabric or other flexible material(s) from which each of patches 101, 103a and 105 is formed (more about which is said below). Rather than attach a plurality of individual electrode strips 104 or patient cables 106 to patient's torso 14, it will be seen that patches 101, 103a (and 103b—not shown in FIGS. 4A through 4C, but configured similarly to patch 103a to sense ECG signals on the side opposite patch 103a of the patient's torso 14), and 105 are considerably less labor intensive and time consuming to place on patient 10. In FIGS. 4A through 4C, proximal electrical connections 115 are configured for attachment to corresponding ECG mapping cable connectors 107, or to any other suitable electrical connector configured to convey electrical signals generated by sensing electrodes E to data acquisition device 210.

Figure 5A:
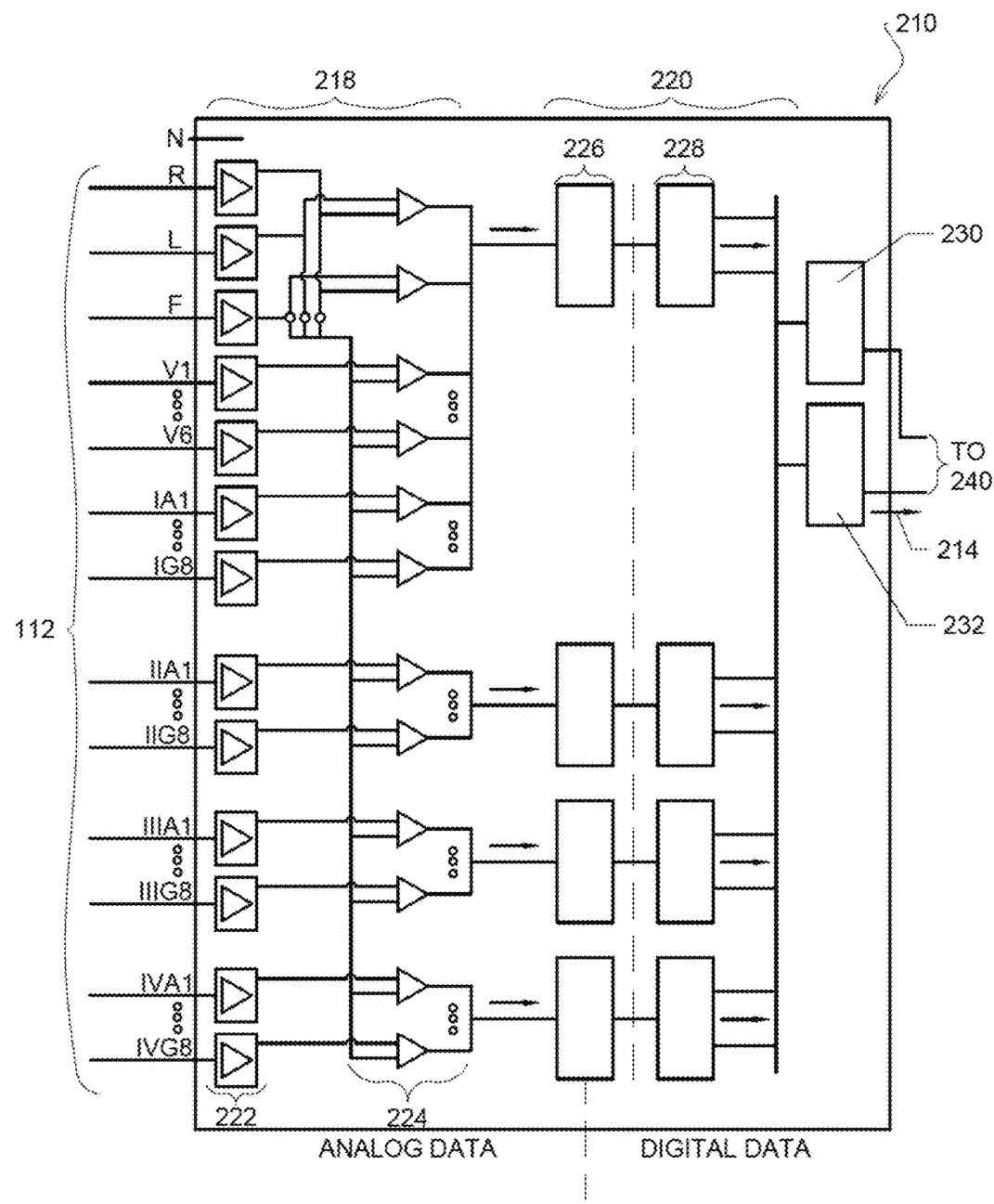
FIG. 5A shows one embodiment of a data acquisition device or measurement system 210 of system 10.
Figure 5B:
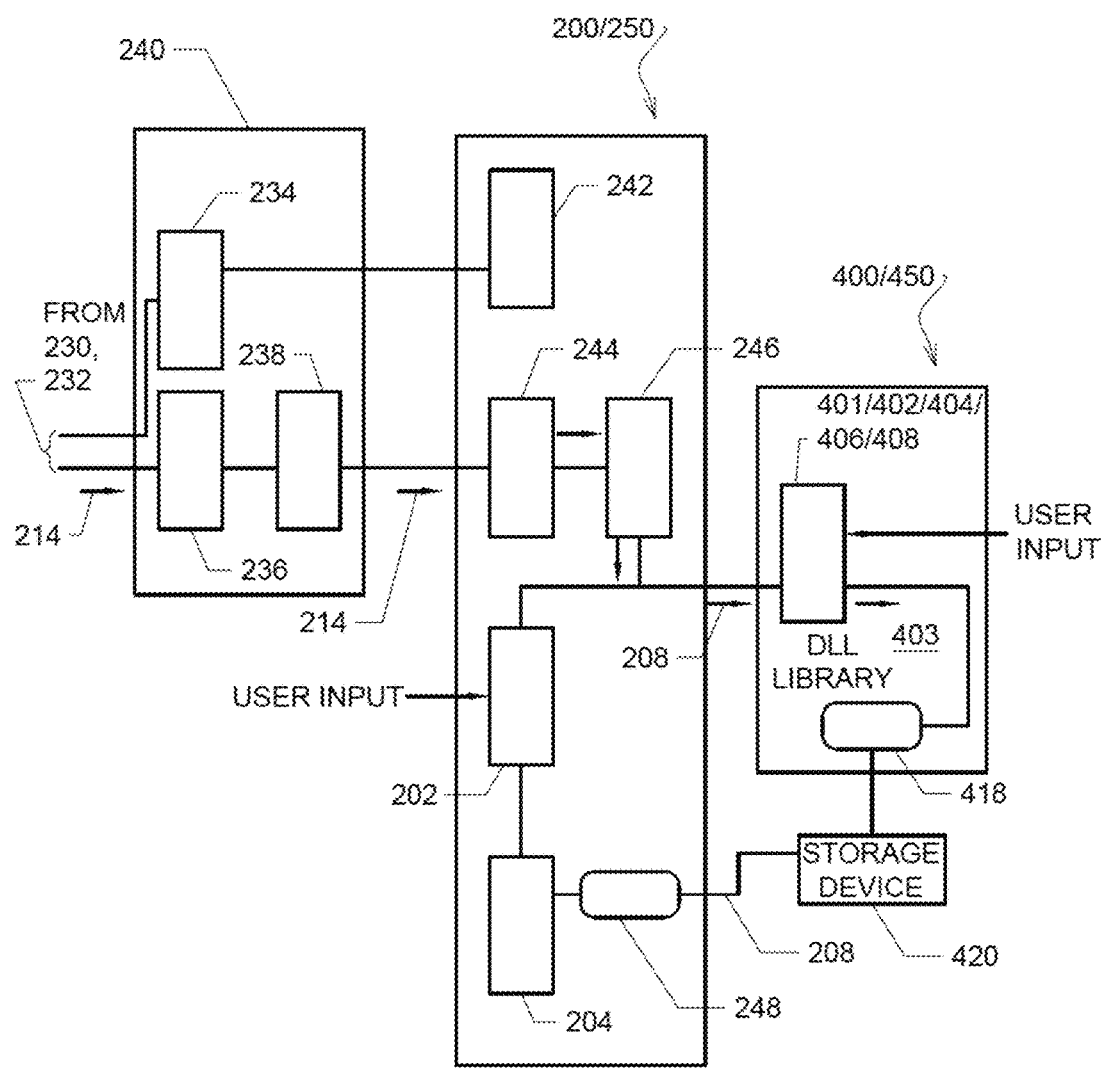
FIG. 5B shows one embodiment of portions of interface cable box 240, MMU 200/250 and PVM 400/450.

FIGS. 5A and 5B show one embodiment of selected portions of system 10, including measurement system or data acquisition device 210, interface cable box 250 disposed between data acquisition device 210 and MMU 200/250, and PVM 400/450. Data acquisition device 210 is configured to interface with MMU 200 through interface cable box 215. For noninvasive cardiac mapping, and according to the various embodiments described and disclosed herein, computed tomography or magnetic resonance imaging and positional data of the patient are required as inputs to MMU 200/250, along with amplified, filtered and digitized ECG data provided by data acquisition device 210 through interface cable box 240. As described above, PVM 400 is configured to receive and process the tomographic images and data processed and generated by MMU 200.

FIG. 5A illustrates one embodiment of data acquisition device 210, which is configured to amplify, filter and convert into a digital format the analog signals 112 sensed by the various surface electrodes attached to the patient's torso 14 and provided by MES/sensor array 100, and to send such digital signals to the MMU 200/250 via interface cable box 240. In turn, MMU 200/250 is configured to interface with PVM 400/450, which generates and displays noninvasive cardiac mapping results.

As further shown in FIG. 5A, and in one embodiment, each of the analog electrode signals 112 acquired from the patient's torso 14 (except that of the neutral electrode) is input into data acquisition device 210 through one of the repeaters/matching amplifiers 222. Analog signals 112 corresponding to the ECG limb electrodes R, L and F are then routed into two of differential amplifiers 224 to produce ECG lead I and ECG lead II signals, respectively. Further, each of the 224 analog signals of the ECG mapping cables and each of the analog signals of the precordial electrodes are led through separate differential amplifiers 224 (having, for example, a common mode rejection ratio >105 dB @ 50 Hz) which employs a reference signal produced from the other electrode signals). Through the neutral electrode N, a signal is applied to the patient's torso 14 body to counteract or diminish common mode noise in the acquired ECG signals.

Once amplified, the collected analog ECG signals are converted into digital signals with four 24-bit analog-to-digital converters 226, each being configured to convert, by way of non-limiting example, up to 64 channels of analog input signals 112 into digital signals at a sampling rate of, for example, 1 kHz (although other sample rates are contemplated). The digital signals are then processed by four micro-controllers, controllers, processors, microprocessors and/or CPUs 228, which send the measurement data or digital signals 214 organized into a suitable digital format to interface cable box 240 using, for example, an RS-232 serial communication standard for transmission of data. To protect the electrical circuits of data acquisition device 210 and those of the electrodes operably connected thereto from harmful currents, DC-DC converters 230 and 234 in combination with galvanic isolation modules 232 and 236 may be employed on both ends of interface cable box 240 to operably connect data acquisition device 210 to interface cable box 250.

MMU 200/250 receives the digital signals 214 provided by the data acquisition device 210 through the interface cable box 240 through, by way of non-limiting example, an integrated RS-232-to-USB interface module, a universal serial bus (USB) cable, or a flash drive. MMU 200/250 collects the data provided by data acquisition device 210 through USB driver 244 and organizes the incoming binary ECG data into packets using a computer algorithm stored in a suitable non-transitory computer readable medium of MMU 200/250 configured, by way of non-limiting example, as a dynamic-link library (DLL) 246. The data packets are then processed in DLL 246 in conjunction with suitable operator interface algorithms loaded in operator interface module 202, and may then be displayed on a graphical output device 216 of MMU 200/250. The data may be further processed in MMU 200/250 using a suitable data review algorithm loaded in data review module 204, which allows a user to select desired time portions of ECG data included in measurement data 214, and to store such portions in a suitable ECG data format. The selected and formatted data (e.g., mapping data 208) may be written or transferred to a suitable memory or storage device (e.g., RAM, a USB flash drive, etc.) via a USB driver 248 or other suitable means (e.g., Ethernet or network connection). Alternatively, MMU 200/250 is configured to transfer mapping data or data packets 208 directly to PVM 400/450 by means of one or more network interfaces that use, for example, the Transmission Control Protocol and the Internet Protocol (TCP/IP).

A second DLL 403 may be included in PVM 400/450, and employs computer algorithms configured to receive mapping data 208, and to process and analyze the mapping data 208.

Note that the systems, devices, components and methods described herein relating to FIGS. 5A and 5B may also be applied to EP catheter system 500, as those skilled in the art will understand.

Figure 6:
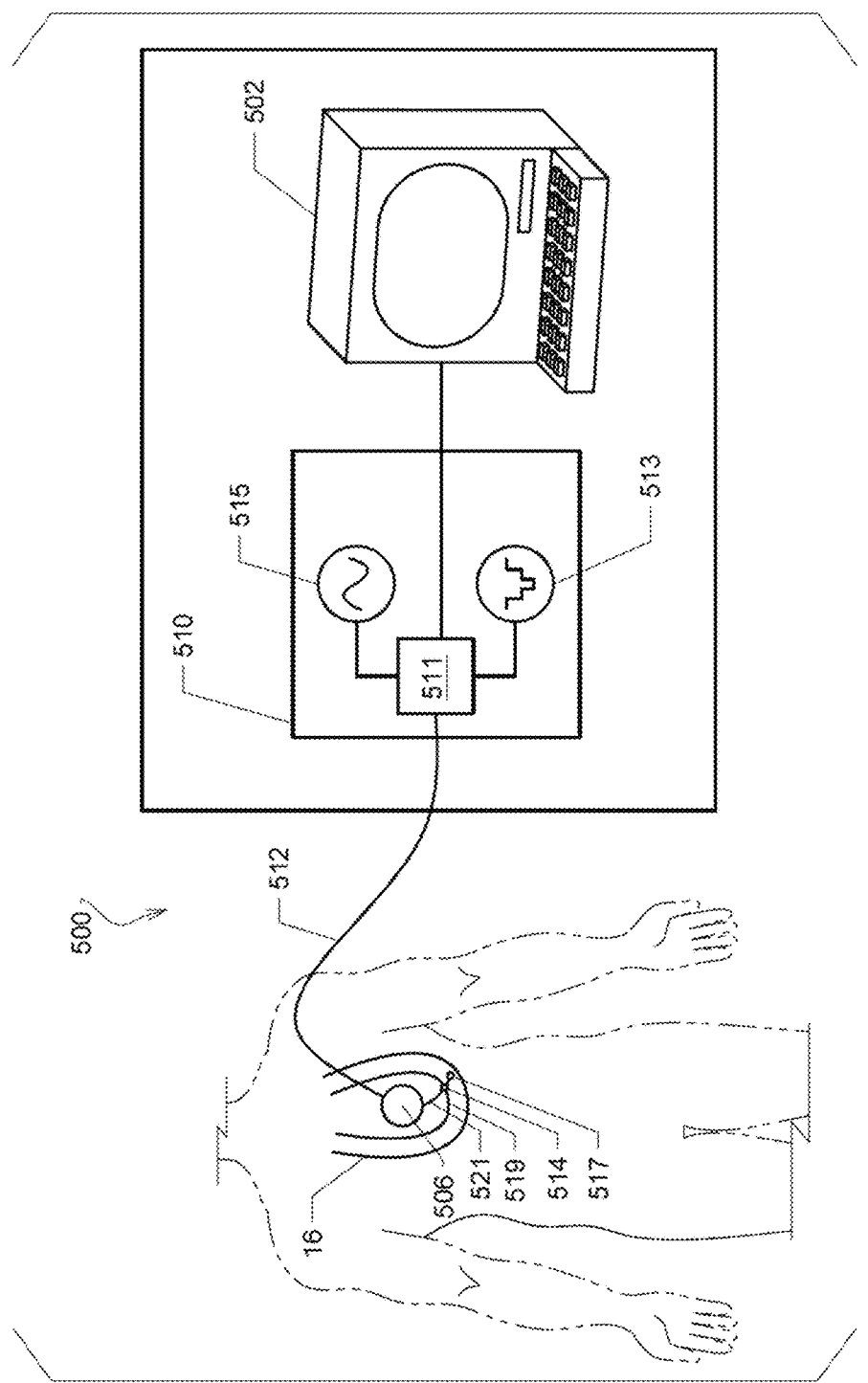
FIG. 6 shows one embodiment of portions of EP catheter system 500.

FIG. 6 shows one embodiment of portions of EP catheter system 500 coupled to a patient's heart 16. EP catheter 512 is inserted into a heart chamber and reference electrode 514 touches the endocardial surface 519. However, any of a variety of catheter constructions may be employed. In one embodiment, electrode array 506 comprises a plurality of sensing and/or stimulation electrodes, which are operably coupled to amplifier and control module 502. In one embodiment, reference catheter 521 is a coaxial extension of the EP catheter 512. Reference catheter 521 includes a surface electrode site 514 and a subsurface electrode site 517, both of which are coupled to amplifier and control module 502. It should be understood that the electrode sites 514 and 517 can be located directly on EP catheter 512. Electrode array 506 may be expanded into a known geometric shape, preferably spherical or elliptical. A balloon or the like may be incorporated into electrode array 506 to exclude blood from the interior of electrode array 506. A spherical shape of the electrode array 506 and exclusion of blood therefrom are not required, but can materially reduce the complexity of calculations required to generate EP mapping displays.

Reference electrodes 514 and 517 and/or the reference catheter 521 serve several purposes. First they stabilize and maintain electrode array 506 at a known distance from a reference point on the endocardial surface 519 for calibration of shape and volume calculations. Secondly, surface electrode 514 can be used to calibrate electrical activity measurements of the endocardial surface 519 provided by electrode array 506.

Amplifier and control module 502 includes switching assembly 511, which is a multiplexer configured to sequentially couple the various electrode sites to the voltage acquisition apparatus 513, and to signal generator apparatus 515. These devices are under the control of a computer 505 included in system 500. Voltage acquisition apparatus 513 is preferably an analog-to-digital (A/D) converter. Signal generator 515 may also be included to generate low current pulses for determining the volume and shape of the endocardial chamber using impedance plethysmography, and for determining the location of reference catheter 521.

Computer 505 is preferably of the "workstation" class to provide sufficient processing power to operate in real or near-real time. Computer 505 operates under the control of software configured to permit EP measurements from EP catheter 512 to be acquired. See U.S. Pat. No. 5,297,549 to Beatty et al. entitled "Endocardial Mapping System," the entirety of which is hereby incorporated by reference herein, for further illustrative examples and details concerning one embodiment of EP catheter system 500. As those skilled in the art will understand, many other types and configurations of EP catheter system 500 may be employed, including those employing Swan-Ganz systems, devices or components.

Figure 7:
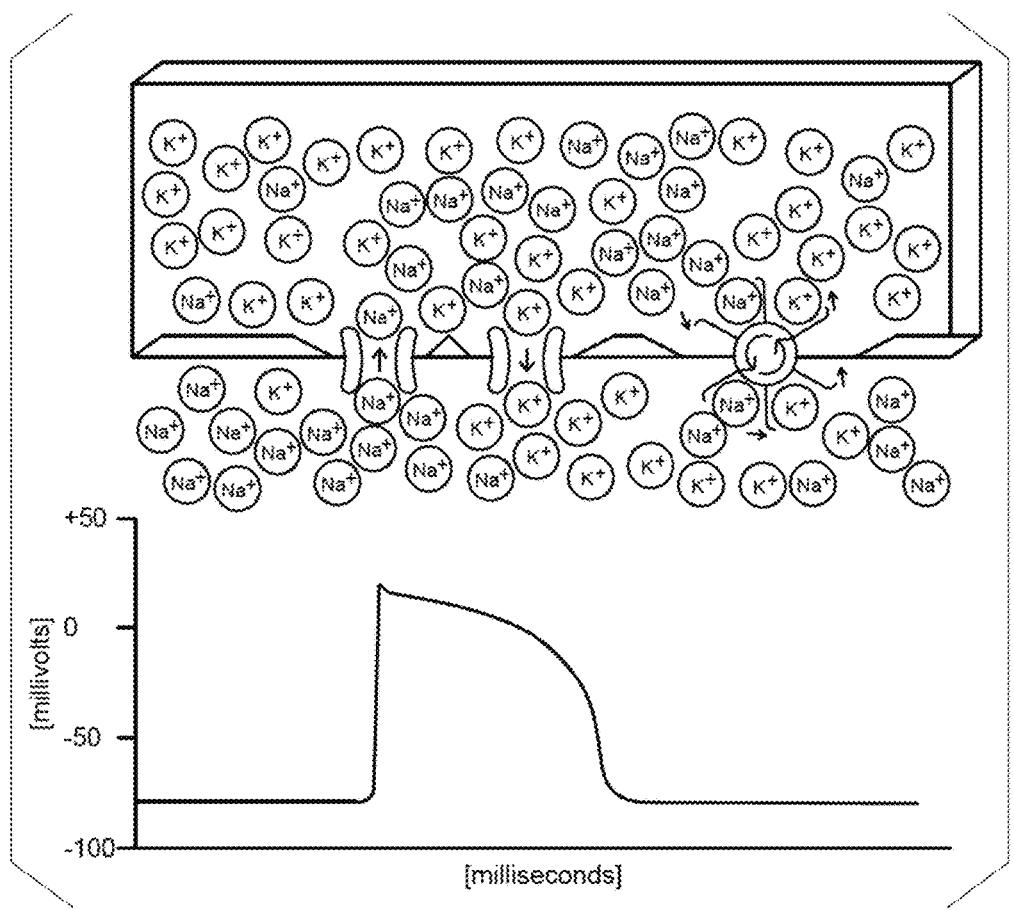
FIGS. 7 and 8 illustrate some basic concepts of cardiac electrophysiology.
Figure 8:
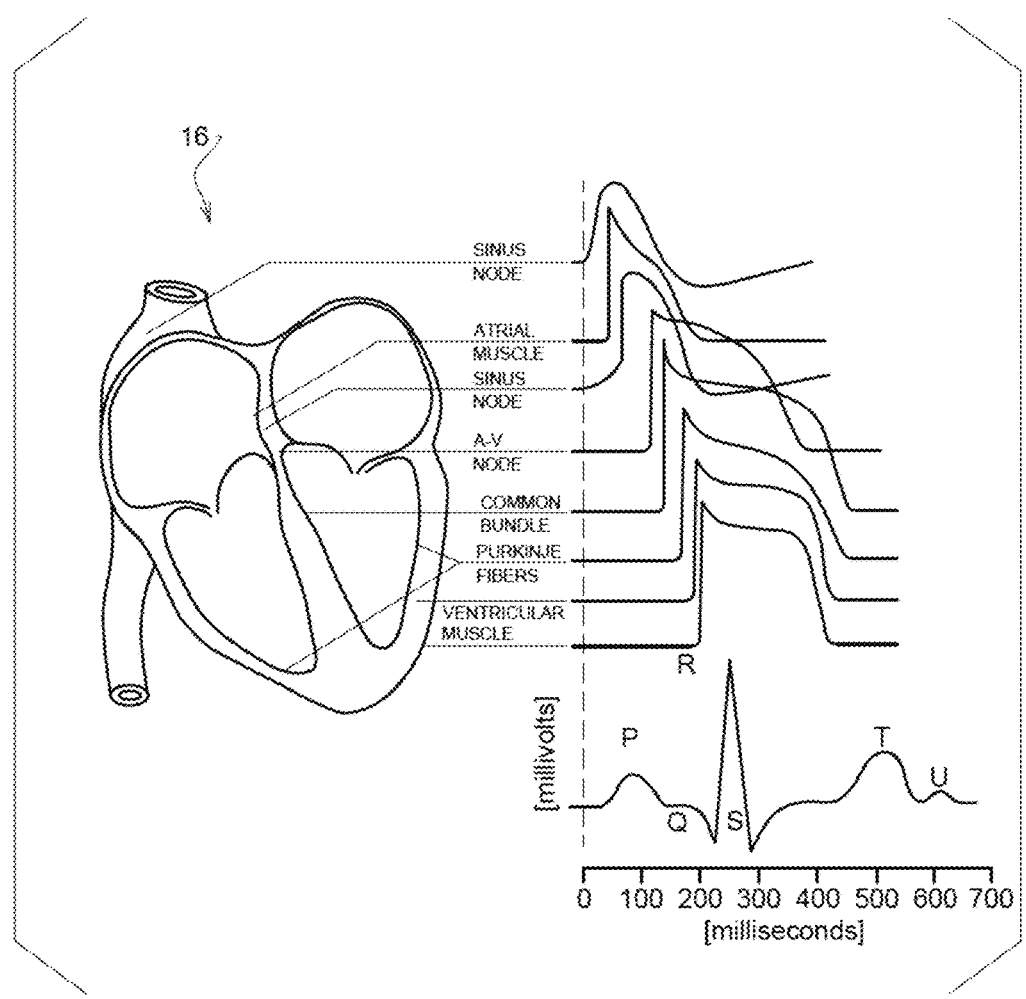

Referring now to FIGS. 7 and 8, the action potential (AP) is a basic concept in cardiac electrophysiology. The AP is a time varying membrane electric potential, which is also referred to in the literature as membrane voltage or transmembrane voltage. The AP is the electrical potential between the interior and the exterior of cardiomyocytes, and its behavior over time is related to electrical activation of the cell caused by ion mechanisms (see FIG. 7). While ion pump and exchange mechanisms maintain the ionic balance of the cell, the AP exhibits a negative resting membrane potential. Upon depolarization, an inflow of sodium ions takes place, distorting the balance and causing an approximate upstroke of 100 mV in the AP. Potassium ions outflow and various other physiological or pathophysiological effects then cause repolarization to a negative membrane potential.

As shown in FIG. 8, AP shapes vary depending on location in heart 16, where different locations have different properties regarding ion channel behaviors. When the myocardium is electrically activated, the spatial gradient between APs causes a local (near field) change in the extracellular electrical potentials, as well as a change in the far field. The resulting cumulative electrical potentials can be measured as ECGs on the body surface or as endocardial ECGs or electrograms on the heart surface.

Unlike electrograms, the AP is a signal that originates only from myocardial electrical activity at the point of registration. The AP allows determining activation and recovery times without any constrictions. Moreover, action potentials directly reflect cellular ionic currents. Therefore, APs permit the cellular substrates from which cardiac arrhythmias arise to be identified.

The cellular AP can be measured directly as electrical potential difference between the interior and the exterior of a single myocardial cell using a special technique with microelectrodes [Polder H. R et al., 2005]. This method cannot be applied for AP mapping on macroscopic scale. In this regard some methods of evaluation of average AP on relatively large areas of the myocardium were developed including recording of monophasic action potentials, optical mapping and numerical reconstruction of AP using mathematical models of cardiac electrical activity.

Monophasic action potential (MAP) is a bipolar electrogram recorded by a bipolar catheter with short distance between electrodes in conditions when the catheter is installed perpendicularly to the cardiac surface and a non-polarizable electrode is pressed against the endocardium or epicardium [Franz M. R., 1999]. The shape of the MAP signal in most cases is similar to AP shape, so AP recording can be used for estimation of AP [Ino T. et al., 1998]. The special intracardiac catheters (so called Franz catheters) designed for MAP recording are available for use in human during cardiac interventional procedures [Franz, 1987], [Lau M. et al.], [Corvi Y. J. et al.].

However, MAP recording for estimation of AP has several disadvantages. The MAP signal quality is sensitive to position of the electrode; also, MAP does not reflect the absolute amplitude or upstroke velocity of cellular AP [Franz M. R., 1999].

Cardiac optical imaging of AP is based on utilizing fast-response voltage sensitive dyes; these bind on to the lipid molecules on a cell membrane and will shift their spectral properties in response to a change in membrane potential. Fluorescent emissions of the potentiometric dyes are detected by special video cameras and transformed to signals that then provide the estimation of AP [Loew L. M., 1996], [Efimov I. R. et al, 2004], [Liang-Chia Chen et al., 2012], [Pertsov A. M., 2012].

The optical mapping technique provides the estimation of AP with high accuracy and time and spatial resolution. However, the optical mapping methodology has some significant limitations. First, optical mapping of AP is suitable for ex vivo heart preparations only. Translation of optical mapping to clinical practice is a promising but extremely challenging problem. Even under ex vivo conditions high-precision optical mapping requires a motionless heart. This condition may be achieved by pharmacological agents that cause electro-mechanical dissociation, but application of these agents can lead to non-physiological experimental conditions. Endocardial optical mapping requires complex endoscopic equipment. In case of epicardial mapping some parts of the cardiac surface may be unavailable for optical measurements due the epicardial fat.

An alternative way of obtaining cardiac electrophysiological information is noninvasive electrocardiographic imaging. This method is based on numerical reconstruction of cardiac electrical activity by body surface ECG mapping using personalized heart and torso geometrical relationships. The electrical activity of the heart can be reconstructed in terms of cardiac surface electric potentials (i.e., in the form of local unipolar electrograms) [C. Ramanatan et al., 2004] or in the form of activation or recovery time imaging [Van Dam P. M. et al., 2012] [Van Dam P. M. et al. 2014], [Berger T. et al, 2006].

The problem of reconstruction of epicardial and endocardial potentials distributions by body surface potentials is an ill-posed problem, meaning that a small error in the initial data can result in much larger errors in the solution. The numerical solving of the ill-posed problem requires application of regularization algorithms. Several regularization methods have been proposed including Tikhonov regularization of 0 and 1 order in L2 and L1 norm [Ghosh S., 2009], truncated singular value decomposition, Twomey regularization, Kalman filter approach, iterative methods, hybrid (multiconstraints) and other approaches [Y. Rudy, 2004, 2006, 2009].

In general, some of these methods (Tikhonov 1 order, iterative approaches) allow obtaining local unipolar electrograms with acceptable mean square error, but reconstructed electrograms are substantially smoothed and have a phase distortion. These errors complicate reconstruction of sequences of activation and recovery of the heart by numerically obtained electrograms.

A number of authors have suggested methods of numerical reconstruction of AP based on body surface ECG mapping. These methods use the so-called bi-domain model of cardiac electrical activity (Geselowitz, D. B., & Miller III, W. T. (1983). A bidomain model for anisotropic cardiac muscle. *Annals of Biomedical Engineering*, 11(3-4), 191-206), which allows establishing the relationship between cardiac AP and body surface ECGs.

Ben He and his co-authors presented methods of noninvasive imaging of cardiac electrical activity in terms of a quantity that is proportional to the 3D gradient of AP; this quantity was named equivalent current density [Bin He, 2003, 20014]. This approach has a significant disadvantage: the problem of reconstruction of the AP or the AP gradient inside the myocardial wall has no unique solution. Different cardiac sources in terms of AP or AP gradient distributions inside the myocardial wall may result in the same body surface potentials. Thus, an attempt of AP reconstruction can lead to physiologically meaningless solutions. In order to overcome this problem some physiological constraints for AP were used in form of Tikhonov and other types of regularization, see e.g. [W. Schulze at al.], [D. Farina et al.] and other.

However, the necessity of setting strong physiological constraints is a significant limitation of the method. The heart can have pathologically changed sites (for example, the sites of myocardial ischemia, myocardial fibrosis or scars, zones with atypical expression of ionic channels of cardiomyocytes) where the AP properties are sharply abnormal and assumptions for constraints may not apply. Note that in such cases cardiac electrophysiological diagnostic has important clinical value.

One purpose of the embodiments disclosed herein is to overcome the above-described limitations of numerical reconstruction of the AP.

Set forth below are numbered selected references relating to the issues described above.

SELECTED REFERENCES

1. Polder H. R., Weskamp M., Linz K., Meyer R. Voltage-Clamp and Patch-Clamp Technique. Practical Methods in Cardiovascular Research/Dhein S., Mohr F., Delmar M. Springer Berlin Heidelberg, New York, 2005.
2. Franz M. R. Current status of monophasic action potential recording: theories, measurements and interpretations. Cardiovascular Research 41 (1999) 25-40.
3. Ino T, Karagueuzian H S, Hong K, Meesmann M, Mandel W J, Peter T. Relation of monophasic action potential recorded with contact electrode to underlying transmembrane action potential properties in isolated cardiac tissues: a systematic microelectrode validation study. Cardiovasc Res. 1998. 22:255-264.
4. Franz M. R. Apparatus and method for recording monophasic action potentials from an in vivo heart. U.S. Pat. No. 4,682,603 (Jul. 28, 1987).
5. Lau M. et al. Mono-phasic action potential electrogram recording catheter, and method US 20110028820 A1
6. Corvi Y. J. et al. Multi-array monophasic action potential medical device. WO2012121882 A1; PCT/US2012/026042
7. Loew L. M. Potentiometric dyes: Imaging electrical activity of cell membranes. Pure and Applied Chemistry, 68(7):1405-1409, 1996.
8. Efimov I. R., Nikolski V. P., Salama G. Optical Imaging of the Heart. Circ Res. 2004; 94:21-33.
9. Liang-Chia Chen et al. Stroboscopic optical image mapping system US 20120292529A1, 2012.
10. Pertsov A. M. et al. Composition, method, system, and kit for optical electrophysiology. U.S. Pat. No. 8,155,730 B2, 2012.
11. Van Dam P. M., van Oosterom A. Inverse imaging of electrical activity of a heart muscle. U.S. Pat. No. 8,838,203 B2; 2014.
12. Van Dam P. M. et al. Non-Invasive Imaging of Cardiac Activation and Recovery. Annals of Biomedical Engineering, Vol. 37, No. 9, 200, pp. 1739-1756.
13. C. Ramanathan et al. A Noninvasive Imaging Modality for Cardiac Electrophysiology and Arrhythmia" Nature Medicine 2004; 10: 422-428.
14. Berger T., Fischer G., Pfeifer B., Modre R., Hanser F., Trieb T., Roithinger F. X., Markus Stuehlinger M., Pachinger O., Tilg B., Hintringer F. Single-Beat Noninvasive Imaging of Cardiac Electrophysiology of Ventricular Pre-Excitation. J Am Coll Cardiol. 2006; 48(10):2045-2052.
15. Yoram Rudy et al. System and methods for noninvasive electrocardiographic imaging (ECGI) using generalized minimum residual (GMRes). US 20030120163; 2004.
16. Yoram Rudy et al. System and method for noninvasive electrocardiographic imaging (ECGI). US 20090053102; 2006.
17. Yoram Rudy et al. Systems and methods for on-site and real-time electrocardiographic imaging (ECGI). US 20110190649; 2009.
18. Ghosh S., Rudy Y. Application of L1-norm regularization to epicardial potential solution of the inverse electrocardiography problem. Annals of Biomedical Engineering, 37:902-912, 2009.
19. Bin He. et al., "Noninvasive Imaging of Cardiac Transmembrane Potentials Within Three-Dimensional Myocardium by Means of a Realistic Geometry Anisotropic Heart Model"; IEEE Transactions on Biomedical Engineering; 2003; pp. 1190-1202; vol. 50; No. 10.
20. Bin He et al. Systems and Methods for Noninvasive Spectral-Spatiotemporal Imaging of Cardiac Electrical Activity. US 20140323848; 2014.
21. W. Schulze, D. Farina, Y. Jiang, O. Dössel A Kalman Filter with Integrated Tikhonov-Regularization to Solve the Inverse Problem of Electrocardiography. World Congress on Medical Physics and Biomedical Engineering, Sep. 7-12, 2009, Munich, Germany.
22. Farina D., Jiang Y., Skipa O., Dössel O., Kaltwasser C., and Bauer W. R. The use of the simulation results as a priori information to solve inverse problem of ECG for a patient. Computers in Cardiology, 32:571-574, 2005

Figure 9:
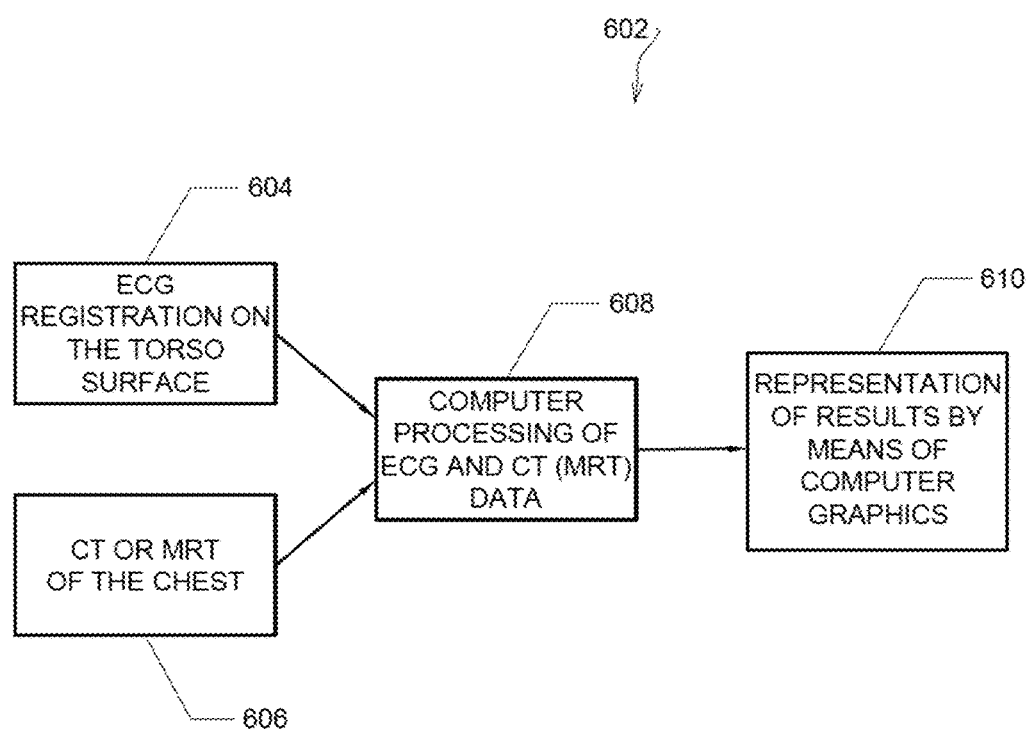
FIG. 9 illustrates a general schematic view of portions of some embodiments of the methods described and disclosed herein.

FIG. 9 illustrates a general schematic view of portions of some embodiments of the methods described and disclosed herein. Method 602 includes: (1) Step 604 (registration of surface electrodes attached to the patient's torso and configured to acquire ECG therefrom); (2) Step 606 (acquisition of CT (computed tomography) data and/or MRT magnetic resonance tomography)/MRI (magnetic resonance imaging) data and ECG electrode position data from the patient's torso); (3) Step 608 (data processing of surface ECG data and of CT data and/or MRT/MRI data) using computing techniques), and (4) Step 610 (visual representation(s) of the obtained electrophysiological information by means of computer graphics processing).

Theoretical descriptions of the electrophysiological processes of the heart are carried out in terms of action potentials. Noninvasive imaging in action potentials terms allows the use of theoretically known regularities of myocardial excitation to improve the accuracy of solving of the inverse electrocardiography problem. It has been shown that the problem of action potential reconstruction at the myocardial surface has a unique solution up to an arbitrary additive constant.

Thus, action potential reconstruction may be carried out in two stages: (a) reconstruction of spatial distributions of action potentials in each time frame, and (b) bringing spatial distributions of action potentials to a single baseline and reconstruction of action potentials as time signals. Disclosed and described herein are methods of noninvasive reconstruction of action potentials on the myocardial surface.

Figure 10:
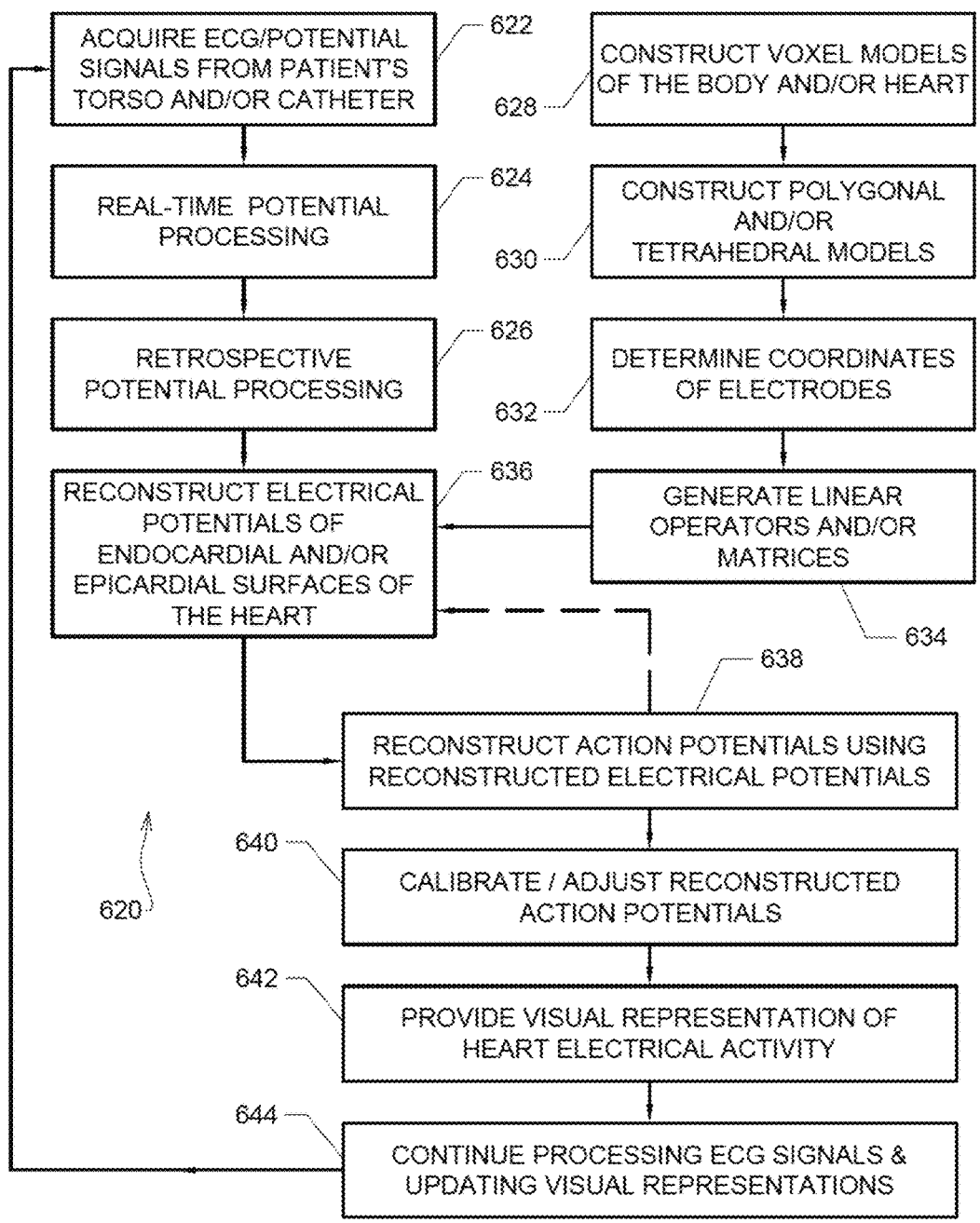
FIG. 10 illustrates a schematic view of one embodiment of the main stages of computer processing of the cardiac electrical signals acquired from the patient's body 12, torso 14 and/or heart 16.

FIG. 10 illustrates a further schematic view of one embodiment of the main stages of computer processing of cardiac electrical signals acquired from the patient's body 12, torso 14 and/or heart 16. Step 622 comprises acquisition of ECG or other potential signals from the patient's torso and/or heart using a mapping unit system 200 and/or an EP mapping system 500. Step 622 may be combined with multi-channel electrode registration generated using CT and/or MRT/MRI data. Step 624 comprises real-time or near-real-time processing of the acquired potential signals. Step 626 comprises retrospective processing of ECG signals. Step 628 comprises constructing voxel models of the torso, heart and its compartments using, by way of non-limiting example, CT or MRT/MRI derived data. Step 630 comprises constructing polygonal or other surfaces or volume models of the torso, heart and its compartments, and may be carried out, by way of example, using boundary element or finite element modelling (FEM) techniques. In one embodiment, step 630 comprises assigning electrical conductivity coefficients of the human torso and/or at least portions of the patient's myocardium to the calculated geometric model, where the geometric model may comprise several models, e.g. models of the torso and heart. Step 632 comprises manual and/or (semi-) automatic determination of the spatial coordinates of surface electrodes on the torso surface, also using, for example, CT and/or MRT/MRI derived data. Step 634 is an optional step that comprises generation of linear operators and/or matrices from the models created in Step 630 and/or from the electrode coordinates determined in Step 632. The linear operators and/or matrices may be produced in Step 634 for use in Step 636 and/or Step 638, but they may as well be generated in Step 634 and/or Step 636 from these models and/or electrode coordinates. It is, however, preferred to perform such procedures in step 634 to prevent delays in the processing of acquired potential signals. Step 636 comprises computational reconstruction of the electrical field potential on the heart's epicardial and/or endocardial surface(s). In one embodiment, step 636 comprises using the cardiac electrical signals from step 624 and/or step 626, the geometric model from step 630, and the electrical conductivity coefficients from step 630 as inputs, calculating reconstructed electrical potential values associated with the myocardial surface.

Figure 14A:
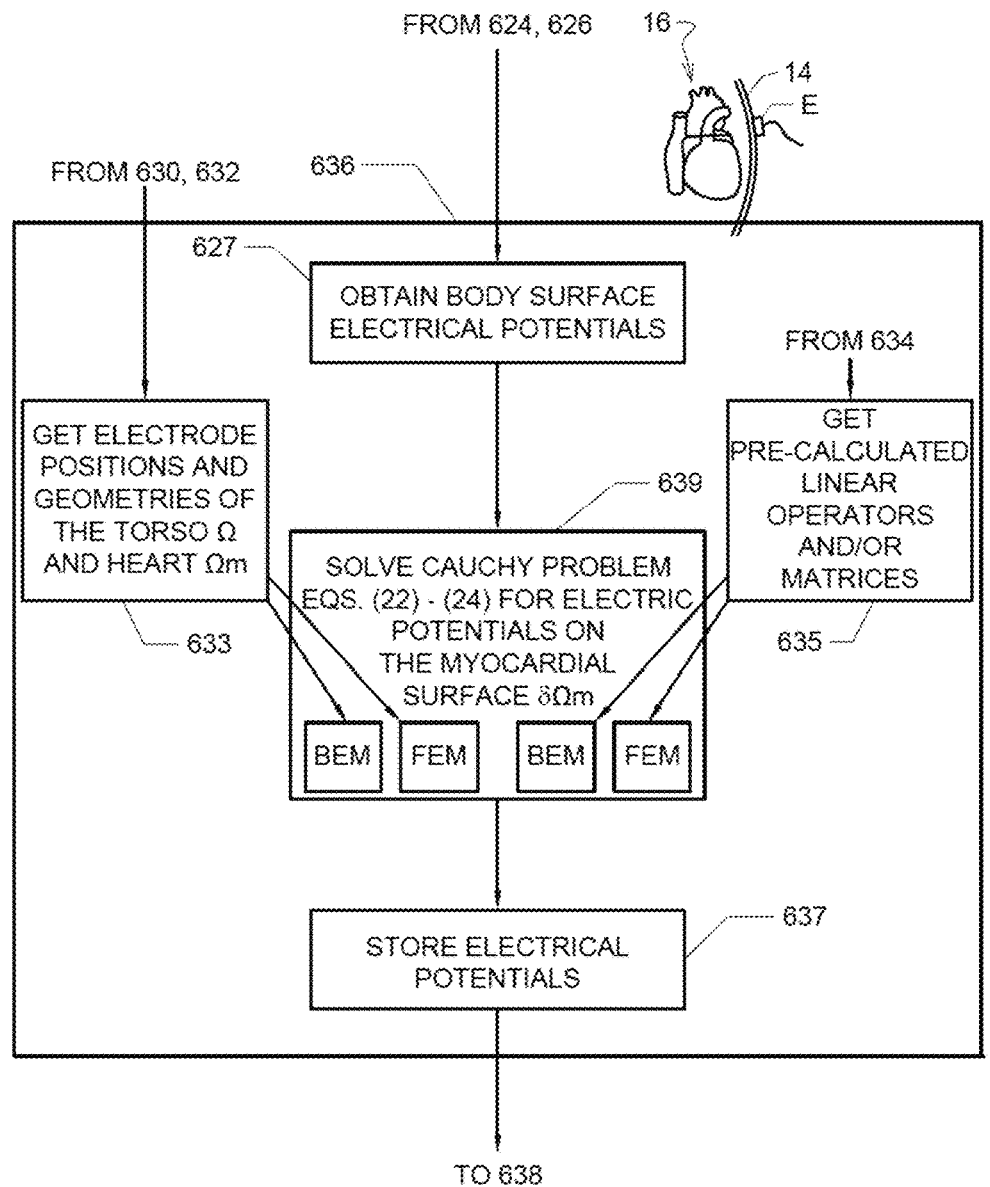
FIGS. 14(a) through 15(c) illustrate some embodiments of the methods disclosed and described herein.
Figure 14B:
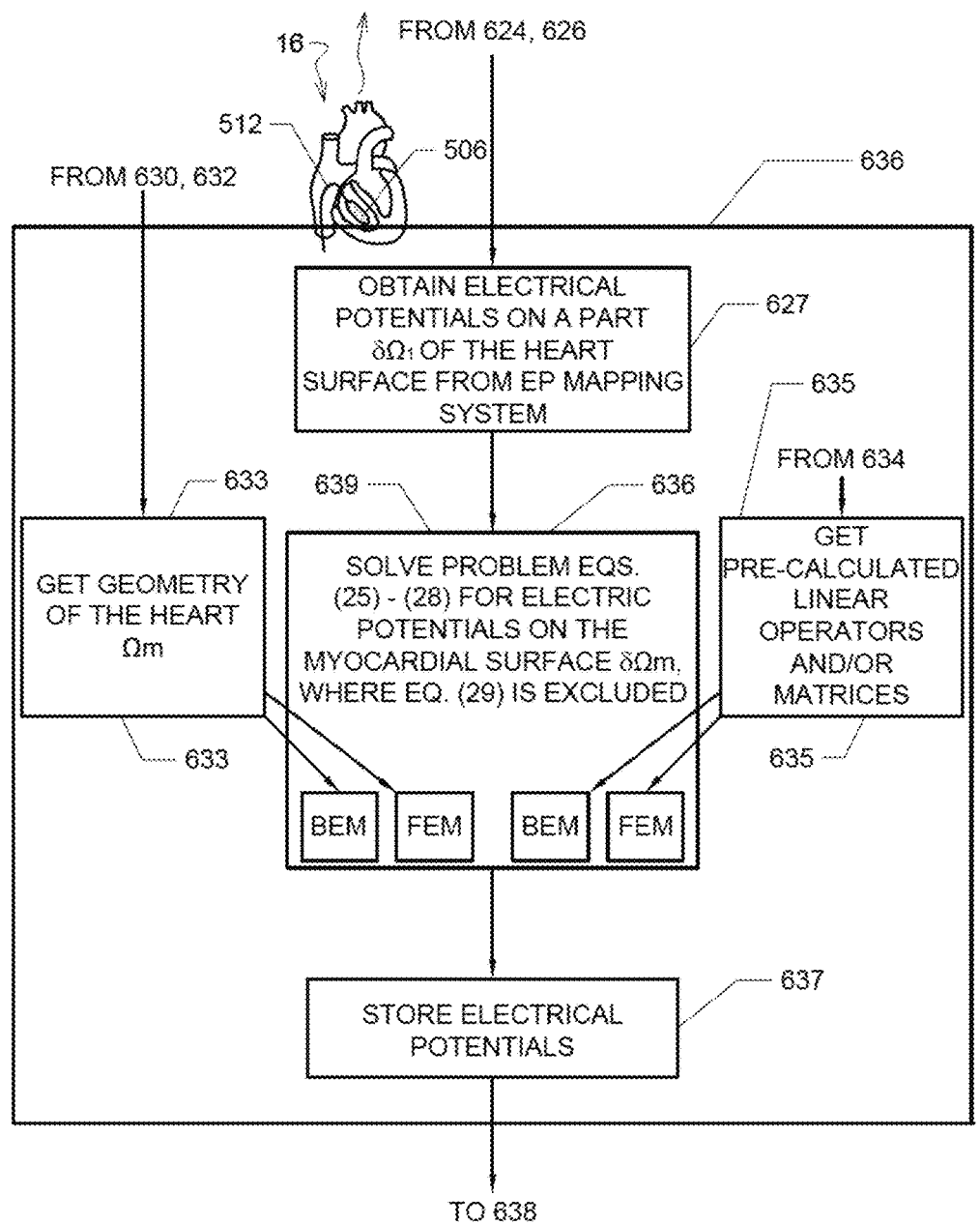
Figure 14C:
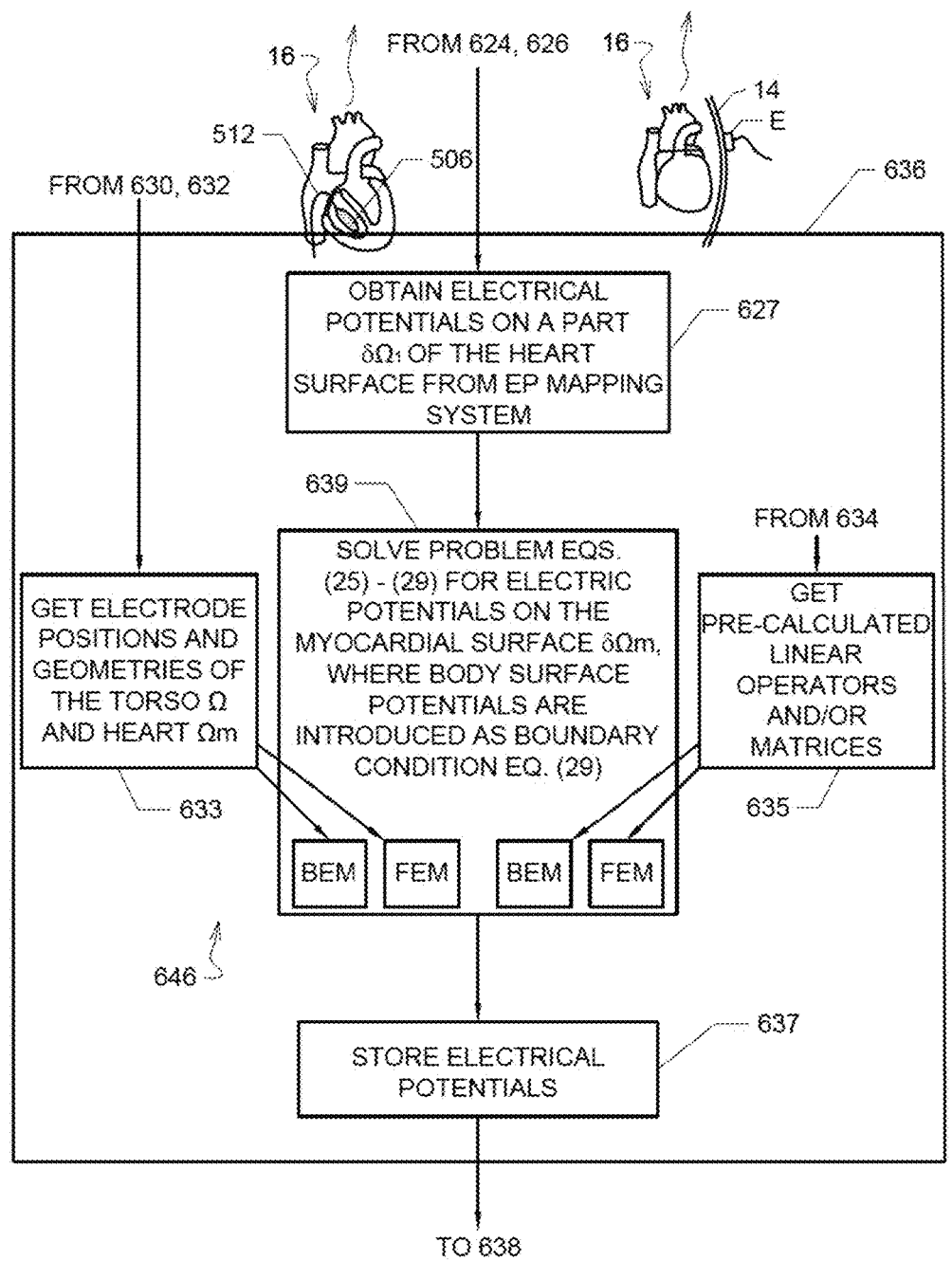

By way of non-limiting example, three embodiments of step 636 are shown in FIGS. 14(*a*), 14(*b*) and 14(*c*). In one embodiment shown in FIG. 14(*a*), step 622 comprises the acquisition of body surface electrical potential signals from the patient's torso, and electrical potentials are reconstructed on the myocardial surface, comprising its endo- and epicardial surface. A second embodiment is shown in FIG. 14(*b*), where step 622 comprises the acquisition of electrical potential signals from a portion of the patient's heart surface and electrical potentials are reconstructed on the myocardial surface, comprising its endo- and epicardial surfaces. A third embodiment is shown in FIG. 14(*c*), where step 622 comprises the acquisition of electrical potential signals from both the patient's body surface/torso and from a portion of the patient's heart surface, and electrical potentials are reconstructed on the myocardial surface, comprising its endo- and epicardial surface (FIG. 14(*c*)).

Figure 15A:
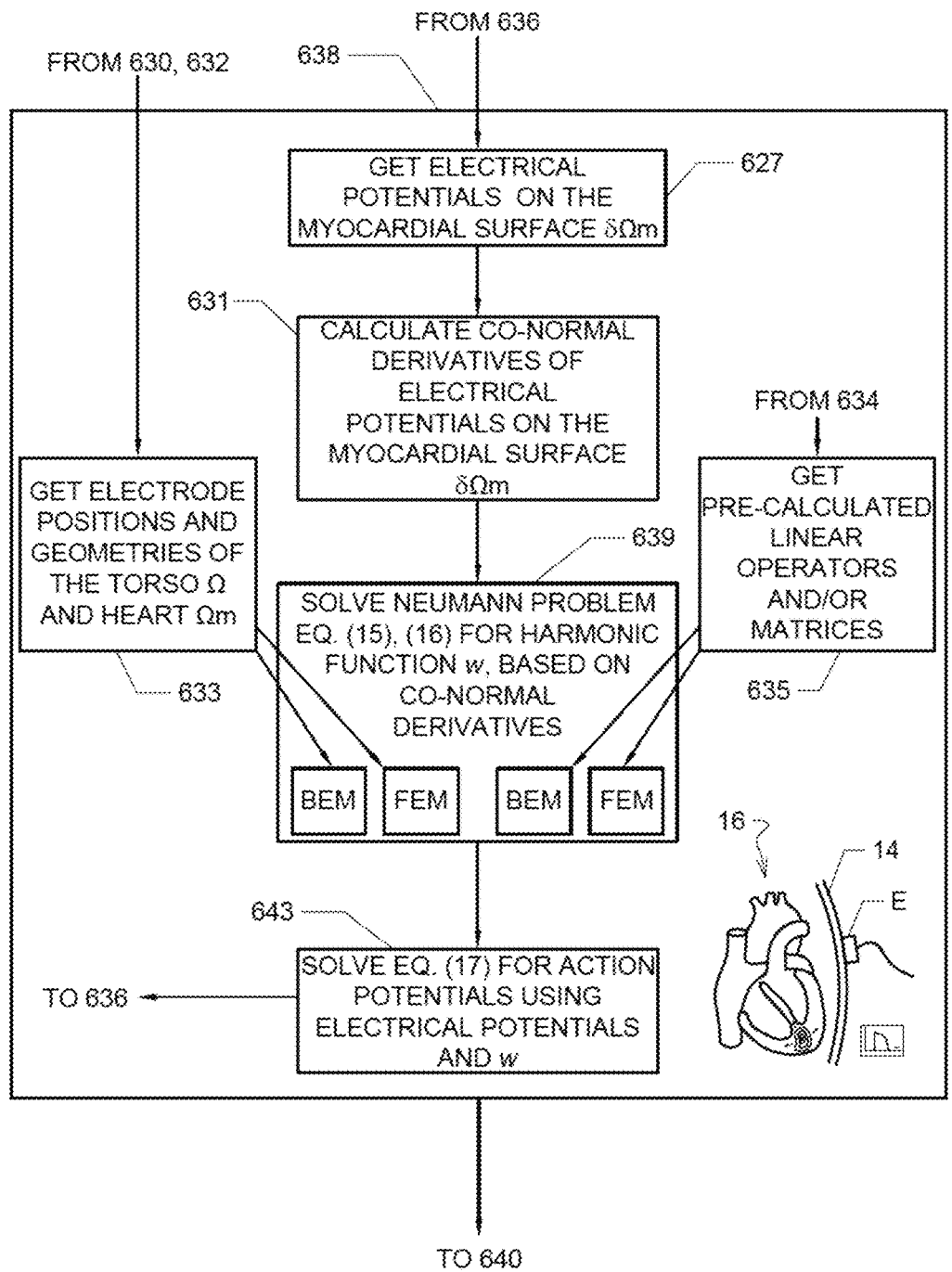
Figure 15B:
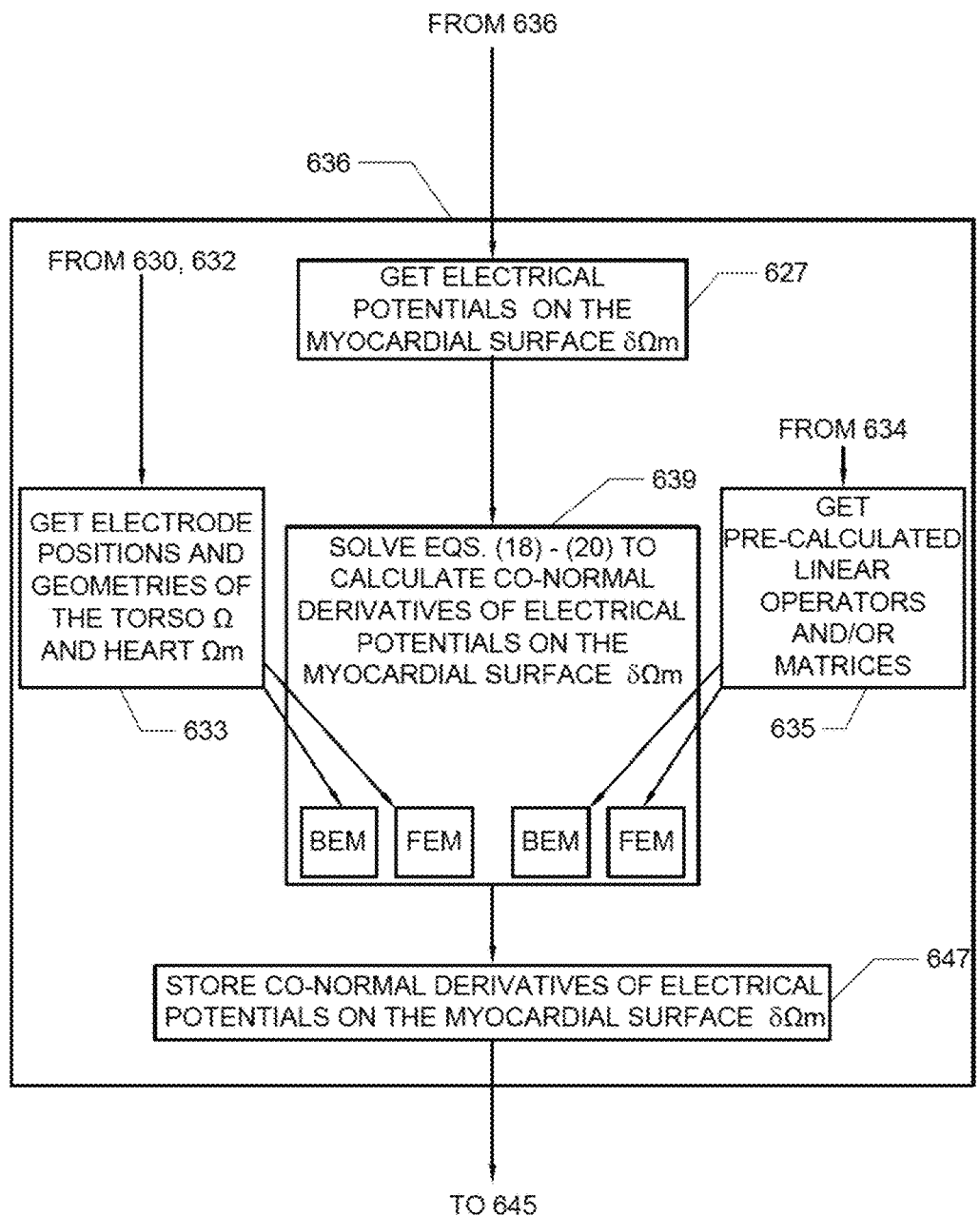
Figure 15C:
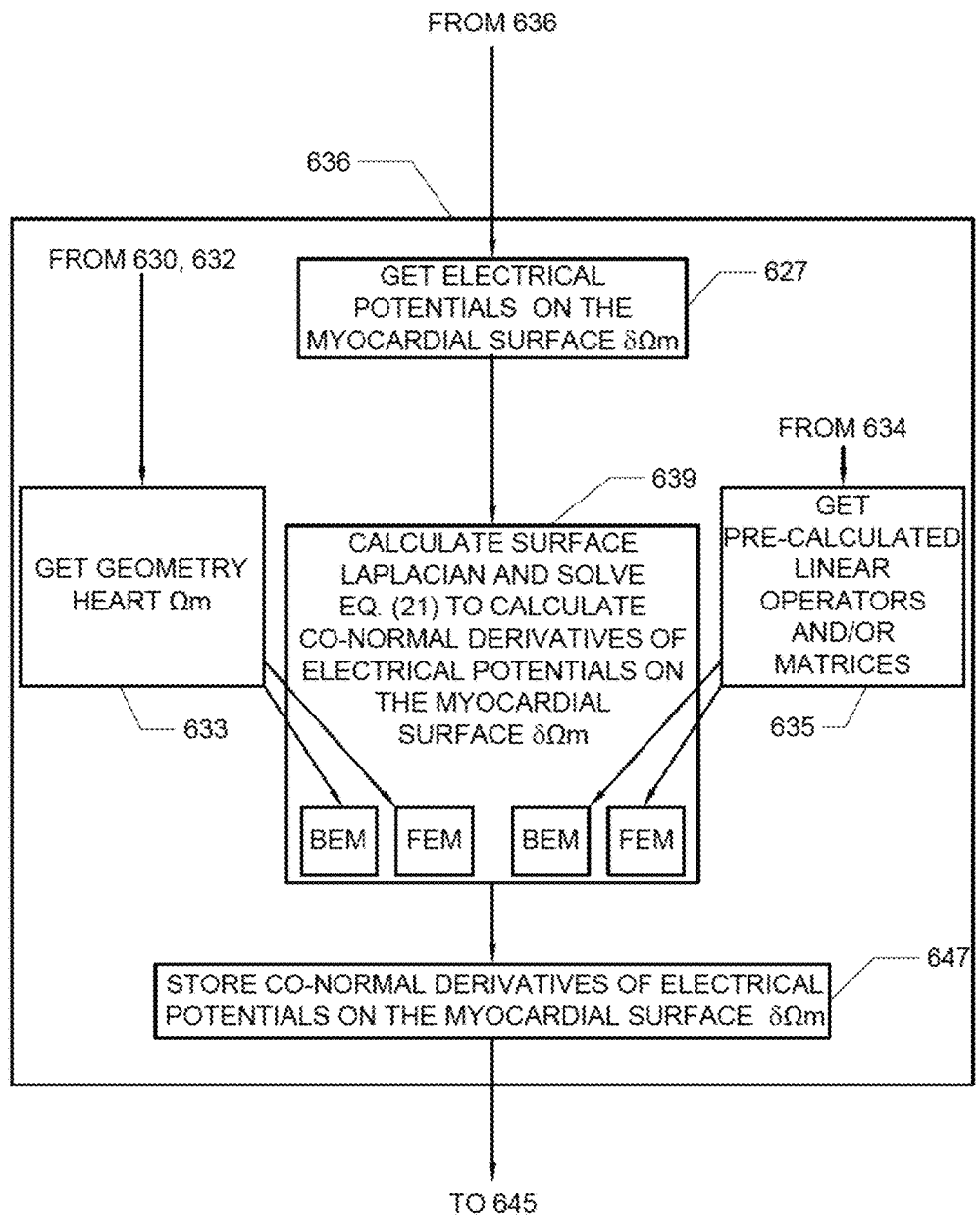

Referring again to FIG. 10, the reconstruction of electrical potentials on the myocardial surface in step 636 is followed by the reconstruction of Action Potentials in step 638. In one embodiment, and as illustrated in FIG. 15(*a*), step 638 comprises step 631 which is the calculation of co-normal derivatives of electrical potentials on the myocardial surface from the previously reconstructed electrical potentials of step 636. In such an embodiment, step 638 further comprises step 639 which requires the co-normal derivatives of electrical potentials on the myocardial surface as calculated in step 631. Based on such calculated co-normal derivatives, in step 639 the Neumann problem of Equations (15) and (16) (shown below) for a harmonic function w is solved, which requires the linear operators and/or matrices that were previously generated in step 634. Alternatively or in addition, some or all of these linear operators and/or matrices may be calculated in step 633, which requires the models created in step 630 and/or the electrode coordinates determined in step 632. Continuing to refer to the embodiment shown in FIG. 15(*a*), the electrical potentials obtained in step 627 and the harmonic function w obtained in step 639 are then used in step 643 to solve Eq. (17) and calculate action potentials on the myocardial surface.

Continuing to refer to FIG. 10, according to one embodiment the reconstruction of action potentials in step 638 may be followed by the reconstruction of electrical potentials in step 636 and again in step 638. In another variant of the latter embodiment, steps 636 and 638 may be performed repetitively in multiple iterations before steps 640, 642 and/or 644 are performed. In yet another embodiment, steps 640, 642 and/or 644 follow directly after execution of steps 636 and 638 (i.e., step 636 is not performed immediately after step 638). In one embodiment, step 638 may be followed by step 640, which is illustrated in FIG. 16(*a*) and FIG. 16(*b*), where a correction or adjustment of the reconstructed action potentials is carried out and is followed by step 642. In other embodiments, step 640 may be skipped and step 642 may follow step 638 immediately.

Referring now to FIGS. 17(*a*), 17(*b*) and 17(*c*), and by way of non-limiting example, an embodiment of step 642 is shown where one or more visual representations of the heart electrical activity are provided in terms of isochronal maps of the activation and/or repolarization/recovery times of action potentials, e.g., in a retrospectively selected heartbeat.

Referring again to FIG. 10, the visual representation of heart electrical activity at step 642 may optionally be followed by step 622 to continue processing ECG and/or other potential signals to update the visual representation(s) carried out in step 642.

By way of non-limiting example, two embodiments of step 629 are illustrated in FIGS. 15(*b*) and 15(*c*). In FIG. 15(*b*), geometries of torso 14 and of heart 16 are required in steps 633 and 635. In FIG. 15(*c*), only heart geometry is required in steps 633 and 635.

Each of the foregoing steps 622, 624, 626, 636, 628, 630 and 632 is described in detail in the aforementioned '547, '461 and '639 patents for the acquisition and processing of electrical potentials from the patient's body 12 or torso 14, and are also partially described above with respect to step 636 of FIG. 14(*a*). Some of the above steps are also described in further detail in U.S. Pat. No. 7,016,719 to Rudy et al. entitled "System and method for noninvasive electrocardiographic imaging (ECGI) using generalized minimum residual (GMRES)" (hereafter "the '719 patent"), the entirety of which is hereby incorporated by reference herein. In addition, certain aspects of the steps described and disclosed herein are described in at least some of the following publications and portions of publications, namely:

22. Revishvili, et al., "Electrophysiological Diagnostics and Interventional Treatment of Complex Cardiac Arrhythmias with Use of the System of Three-Dimensional Electro-Anatomical Mapping," pp. 32-37 (2003);
23. Titomir, et al., "Noninvasive Electrocardiotopography," pp. 97-111 (2003);
24. Shakin, "Computational Electrocardiography," Nauka, pp. 64-65 (1981);
25. Golnik, et al., "Construction and Application of Preprocessor for Generation, Performance Control, and Optimization of Triangulation Grids of Contact Systems," pp. 1-25 (2004);
26. Titomir, et al., "Mathematical Modeling of the Cardiac Bioelectric Generator," Nauka, pp. 329-331 (1999);
27. Lacroute, "Fast Volume Rendering Using a Shear-Warp Factorization of the Viewing Transformation," Computer Systems Laboratory, Depts. of Electrical Engineering and Computer Science, Stanford University, pp. 29-43 (1995);
28. Lorensen, et al., "Marching Cubes: A High Resolution 3D Surface Construction Algorithm," Computer Graphics, vol. 21, No. 4, pp. 163-169 (1987);
29. Saad, "Iterative Methods for Sparse Linear Systems," Second Edition with Corrections, pp. 2-21, 157-172 (July 2000);
30. Rudy, et al., "The Inverse Problem in Electrocardiography: Solutions in Terms of Epicardial Potentials," Crit Rev Biomed Eng., pp. 215-268 (1988); Abstract.

31. Berger, et al., "Single-Beat Noninvasive Imaging of Cardiac Electrophysiology of Ventricular Pre-Excitation," Journal of the American College of Cardiology, pp. 2045-2052 (2006).
32. Lo, "Volume Discretization into Tetrahedra—II. 3D Triangulation by Advancing Front Approach," Computers & Structures, vol. 39, Issue 5, pp. 501-511 (1991);
33. Rassineux, "3D Mesh Adaption. Optimization of Tetrahedral Meshes by Advancing Front Technique," Computer Methods in Applied Mechanics and Engineering 141, pp. 335-354 (1997);
34. Yoshida, "Applications of Fast Multipole Method to Boundary Integral Equation Method," Dept. of Global Environment Eng., Kyoto Univ., Japan, pp. 84-86 (March 2001);
35. Kazhdan, et al., "Poisson Surface Reconstruction," Eurographics Symposium on Geometry Processing (2006);
36. Schilling, et al., "Endocardial Mapping of Atrial Fibrillation in the Human Right Atrium Using a Noncontact Catheter," European Heart Journal, pp. 550-564 (2000);
37. Ramanathan, et al., "Noninvasive Electrocardiographic Imaging for Cardiac Electrophysiology and Arrhythmia," Nature Medicine, pp. 1-7 (2004), and
38. MacLeod, et al., "Recent Progress in Inverse Problems in Electrocardiology," Nora Eccles Harrison Cardiovascular Research and Training Institute, University of Utah, pp. 1-20, 1998.

Continuing to refer to FIG. 10, in Step 624 real-time or near-real-time processing of the acquired potential signals is carried out, which may be combined with multi-channel ECG electrode registration from the patient's torso generated using CT and/or MRT/MRI data. According to one embodiment, in the course of real-time or near-real-time ECG mapping, surface ECG signals that have been acquired from the patient's torso 14 in Step 622 may be displayed on a computer monitor or display to a user and/or health care provider. The user controls the quality of ECG signals from each of the leads; if necessary, a programmed suppression of power-line, muscle noise and of isoline- or DC-drift is applied. Automatic control and editing of the quality of acquired ECG signals may also be carried out based on spectral and mutual-correlation analyses of ECG signals. Results obtained in Step 624 are digitized and filtered values of the ECG signals, and may include, by way of example, signals from 224 or 240 unipolar leads located on the patient's torso and 12 standard leads. In one embodiment, ECG signals are acquired from the patient for up to 1, 2, 3, 4 or 5 minutes.

Still referring to FIG. 10, in Step 626 "retrospective processing" of potential signals occurs. In one embodiment, the user and/or health care provider looks through the acquired ECG signals and selects one or several cardio-cycles for subsequent processing. Further, a reduction of ECG signals to their isoline may be implemented: to this end, in one of the ECG signals the user selects a time interval tau, within which an ECG signal coincides with an isoline (for example, this interval may belong to a cardiac signal segment PQ). Correction of ECG signals is implemented according to the formula: $U0(t)=U(t)-u0$, where $U0(t)$ is the selected and corrected ECG-signal, $U(t)$ is an initial ECG signal, and $u0$ is an averaged value of the initial ECG signal within a time interval tau. Afterwards, the user selects a time interval of interest in the cardiac cycle for subsequent calculations.

In Step 628 of FIG. 10, voxel models of the torso and heart are constructed using a voxel graphics editor. Using the aforementioned CT or MRT/MRI or other electrode, sensor or transducer spatial position/location data of the patient's torso 14 and heart 16, a voxel rendering of anatomical structures of the torso 14 is provided. To this end, and in one embodiment, a "shear-warp factorization" of the viewing transformation algorithm, which belongs to a group of scanline-order volume rendering methods, may be used. In one embodiment, the voxel rendering method applied comprises three main steps. In a first step, volume data are transformed by a shear matrix in the corresponding object space, each parallel slice of volume data after transformation being passed through a filter configured to diminish distortions in the volume data. In a second step, an intermediate 2D image within the same shear space is formed from a combined set of filtered and sheared slices using direct-order superposition. In a third step, the intermediate 2D image obtained is transformed into a normal image space using a shear matrix and is then passed through a filter to form the final image. See, for example, Philippe Lacroute, "Fast Volume Rendering Using a Shear-Warp Factorization of the Viewing Transformation," Ph.D. dissertation, Technical Report CSL-TR-95-678, Stanford University, 1995.

Figure 11A:
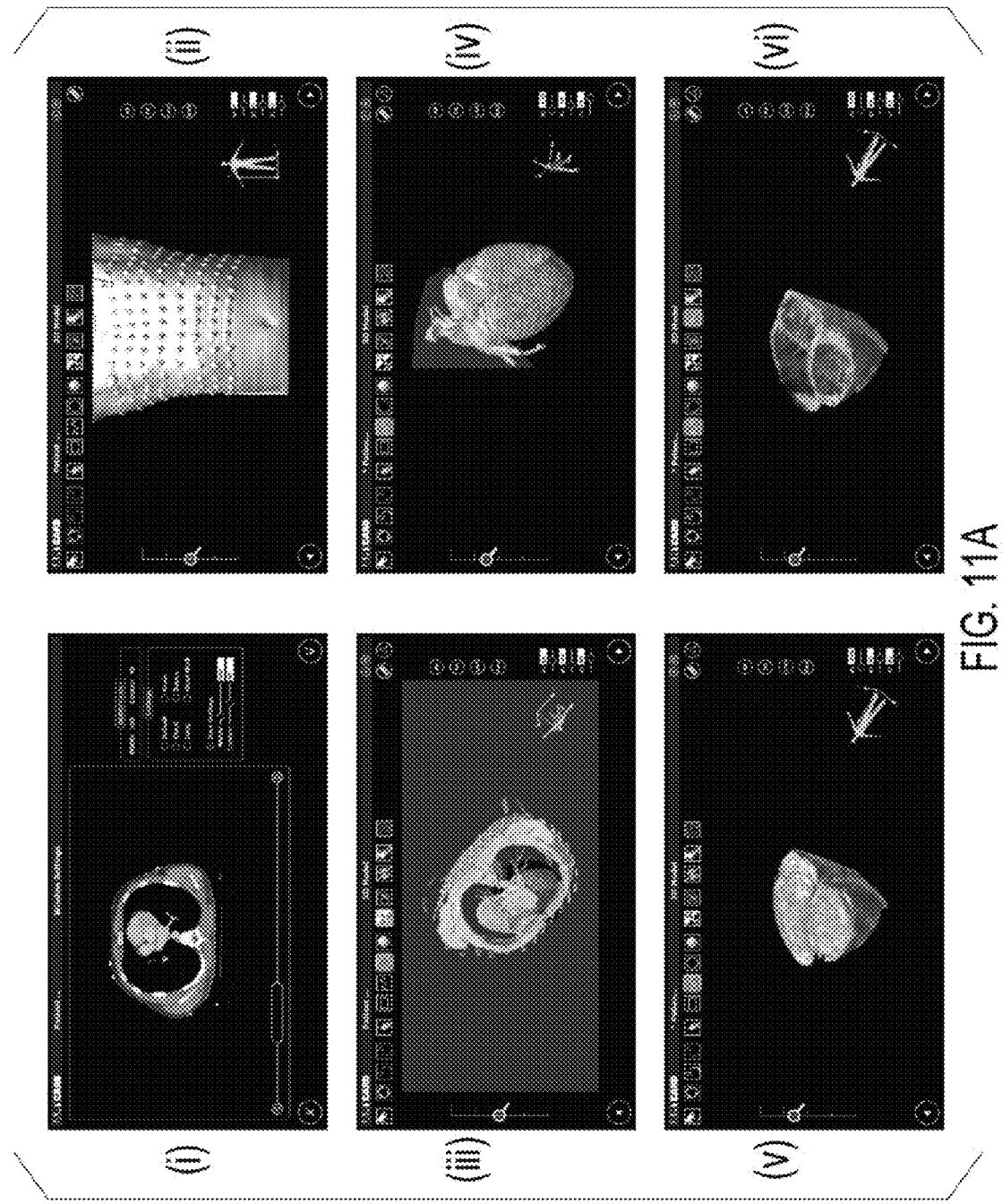
FIGS. 11(a) through 11(c) illustrate constructing a voxel model, constructing polygonal models, and determining coordinates of electrodes.

Referring to FIG. 11(a) now, by way of non-limiting example, voxel models of the torso and heart may be constructed with a voxel graphics editor in Step 628 in the following sequence: Tomographic images of the torso (a) may be loaded and then visualized as three-dimensional voxel model of the torso (b). Extracardial tissues may then be removed with a voxel-based selection and segmentation tool of the voxel graphics editor (c), or alternatively, with an automatic voxel-based filtering algorithm. Subsequently, remaining extracardial tissues may be manually removed with another voxel-based segmentation tool (d) in the editor. Then, an epi- and endocardial voxel model may be semi-automatically derived from the edited voxel image (e), and the resulting epi- and endocardial voxel model may be visualized (f).

Referring again to FIG. 10, in Step 630 polygonal surfaces (or triangulation grids) and/or tetrahedral models and/or any other kind of suitable geometric models of at least one of portions of the patient's torso and portions of the patient's heart of the torso and/or heart may be calculated on the basis of the patient geometry data calculated and provided in Step 628. In one embodiment, such patient geometry data may comprise voxel models of at least one of portions of the patient's torso and portions of the patient's heart. In one embodiment, and based on the obtained voxel models, polygonal surfaces consisting of united plane triangles are automatically constructed. The Initial data employed in such a construction are representative of a three-dimensional scalar field of densities provided in a voxel presentation or format (i.e., a three-dimensional right-angled grid, in which nodes values of the conditional densities of torso tissues are provided). Constructing triangulation grids of the torso and heart is accomplished by constructing polygonal surfaces, which may be repeated surfaces of the structures provided by the three-dimensional scalar density field. Other types of modelling techniques may be used in Step 630, such as finite element models.

In one embodiment, a procedure for constructing polygonal surfaces includes the following steps: filtering initial voxel models to reduce or diminish undesired noise; constructing a triangular surface on the basis of a "marching cubes" algorithm and "exhaustion method" (also known in the literature as an "advancing front" algorithm); smoothing the resulting grid of surface values (i.e., constructing a polygonal surface close to the initially-derived polygonal surface but differing from it by having lower values of angles between the normal vectors of adjacent triangles; and rarefying and quality-improving the smoothed grid of surface values of the polygonal grid (i.e., constructing a polygonal surface with a lower number of larger triangles, which are close to equilateral triangles). A "marching cubes" algorithm permits the construction of a polygonal representation of isosurfaces given by a three-dimensional scalar field of densities. For further details regarding such steps, see, for example, the '547 '461, '639 and '719 patents. See also, for example: (a) W. Lorensen, H. Cline, "Marching Cubes: A High Resolution 3D Surface Construction Algorithm," Computer Graphics, 21(4): 163-169, July 1987); (b) Lo, S. H., "Volume Discretization into Tetrahedra, II. 3D Triangulation by Advancing Front Approach," Computers and Structures, Pergamon, Vol. 39, No. 5, p. p. 501-511, 1991; (c) Rassineux, A. "Generation and Optimization of Tetrahedral Meshes by Advancing Front Technique/International Journal for Numerical Methods in Engineering," Wiley, Vol. 41, p.p. 651-674, 1998; (d) Gol'nik, E. R., Vdovichenko, A. A., Uspekhov, A. A., "Construction and Application of a Preprocessor of Generation, Quality Control, and Optimization of Triangulation Grids of Contact Systems," Information Technologies, 2004, No. 4, p. 2-10.

Figure 11B:
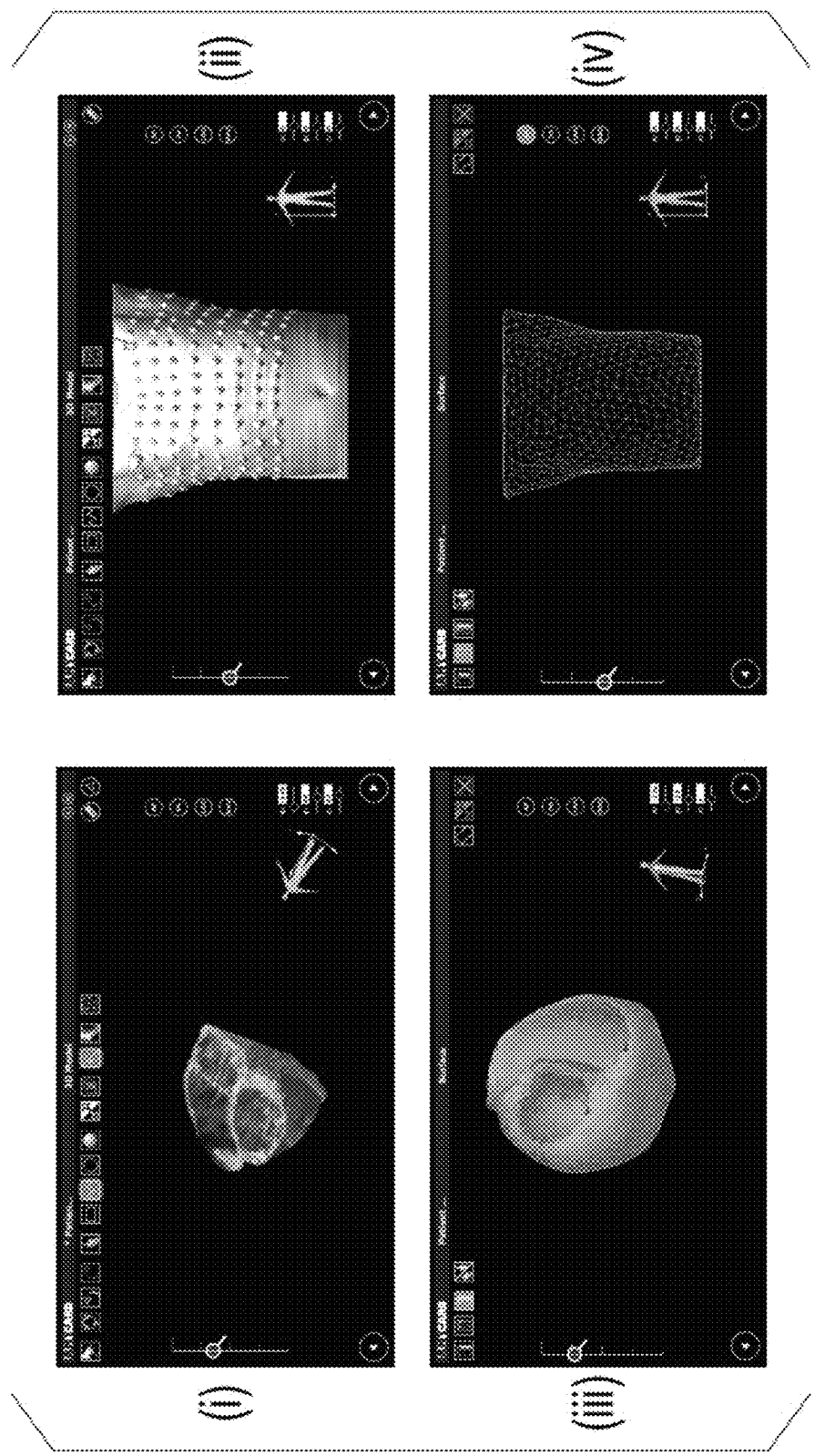

Referring now to FIG. 11(b), in one embodiment the voxel models of the heart (a) and torso (b), as calculated and provided in Step 628, may be displayed on a graphical user interface, and the results of the triangulation of the heart (c) and/or those of the torso (d) as calculated and provided in Step 630 may be displayed in the end of the said step on a graphical user interface.

Referring again to FIG. 10, in Step 632, and according to one embodiment, automatic determination of the spatial three-dimensional coordinates of the ECG electrodes attached to the patient's torso is carried out using the previously acquired CT or MRT/MRI data of the patient's torso. Initial tomography data are digitally filtered using a predetermined density threshold such that only those tomography data are retained that correspond to the density levels of the various surface ECG electrodes. On the basis of a new voxel model computed using the filtered tomography data, a multi-electrode triangulation grid is constructed using the "marching cubes" method. For each electrode location in the triangulation grid, the coordinates of its geometrical center are calculated as an arithmetical mean of the coordinates of its corresponding nodes. For each region, the Euclidean distance from its geometrical center to the nearest point of the surface of the torso is calculated. Regions with the Euclidean distances exceeding a predetermined threshold are rejected. Geometric centers of the remaining regions are assumed to be the Cartesian coordinates of electrodes in three-dimensional space. In accordance with such an ECG electrode spatial positioning and determination scheme, the spatial coordinates are calculated and assigned to each ECG electrode. During this step, the user and/or health care provider may have the option to correct the positions each of electrode in an interactive mode.

Figure 11C:
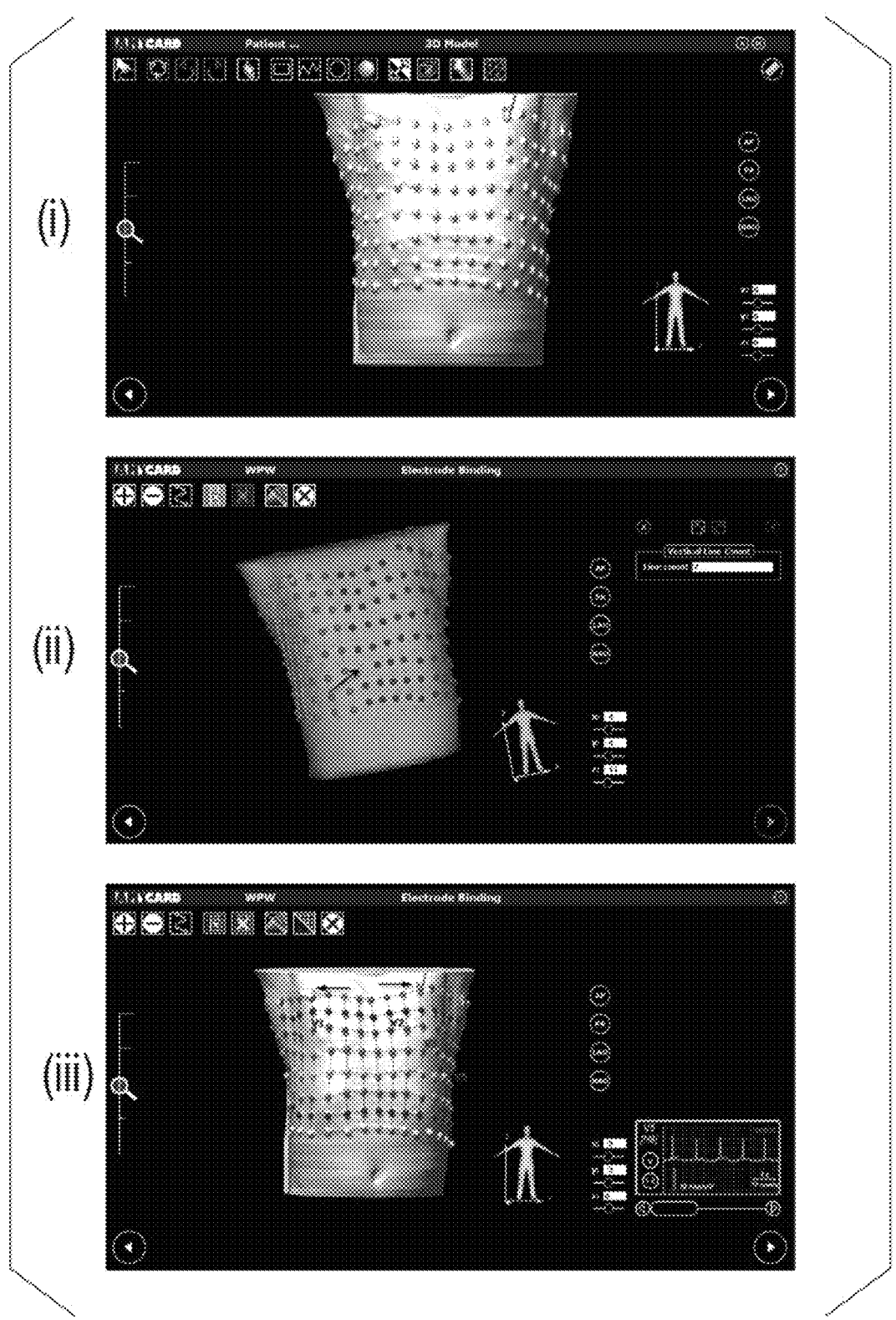

Referring now to FIG. 11(c), in one embodiment of Step 632 the voxel model of the torso is shown (a) in a graphical user interface on a computer screen. Automatic determination of electrode positions is then performed as described in the previous paragraphs, followed by semi-automatic channel assignment using a purpose-specific tool in a graphical user interface (b), and then followed by visualizing the resulting channel assignments to the electrodes on the graphical interface (c).

In some embodiments, a method may include noninvasive reconstruction of the heart's electrical field potential at internal points of the torso based on measured values of the electric field potential on the torso surface by numerically solving the inverse problem of electrocardiography for an electrically homogenous model of the torso by a boundary element method on the basis of an iteration algorithm (as, for example, described in the '660 patent). Solution of the inverse problem of electrocardiography may comprise a harmonic continuation of the potential u(x) from the surface. See, for example, Brebbia, C. A., Telles, J. C. F., & Wrobel, L. (2012). *Boundary element techniques: theory and applications in engineering*. Springer Science & Business Media. The external surface of the heart and surfaces bounding the torso may be approximated by a boundary-element grid, i.e., a polygonal surface comprising plane triangles, which are split into boundary elements. The potential u(s) and its normal derivative q(s) may be represented in the form of decomposition according to a system of linearly independent finite basis functions, where coefficients of decomposition $u_i$ and $q_i$ are values of the potential u(s) and its normal derivative q(s) in nodes of a boundary-element grid. As a result, a number of vectors are formed. The direct boundary element method may employ Green's third (main) formula, which connects values of the potential and its normal derivative at boundary surfaces with values of the potential within the computational domain. Use of Green's third formula for points laying on surfaces yields a system of Fredholm integral equations, which may be written in the form of a system of two matrix-vector equations with two unknown vectors $u_h$ and $q_h$ after boundary-element discretization of functions u(s) and q(s). An iteration algorithm is then employed, which may involve applying the Morozov principle and the Tikhonov regularization method. In one embodiment, the total number of triangle elements in a grid for the torso and heart is about 2252. To model the standard electric field of the heart, a quadruple source can be placed in a geometric center of the heart. The construction of isopotential maps is thus carried out by surface interpolation of values of ECG signals at each discrete moment in time with using radial basis functions. Further details concerning Step 620 described above are set forth in the '547 '461, '639 and '719 patents, as well as in some of the publications referenced herein.

In Step 622 of FIG. 10, the electric field of the heart's surface is computed, and in one embodiment an algorithm and method similar to that disclosed in the '719 patent is employed, which involves application of a generalized minimum residual (GMRES) algorithm. The parameters of the GMRES algorithm, of a model for the torso 14 and heart 16, and of a standard electric field may be the same as those described above in connection with the '719 patent, and are also discussed in detail in the 547, '461 and '639 patents (as well as in some of the publication referenced herein). See also, Saad, Y. "Iterative Methods for Sparse Linear Systems," (2nd ed.), SIAM, Philadelphia (2003).

Using the foregoing techniques and methods, it will now be seen that various types of visual representations of the electrical activity of the patient's heart can be provided by the above-described non-invasive external electrophysiological mapping system or EMS 10. In one embodiment, EMS 10 comprises: (a) a plurality of electrical sensing electrodes E configured to acquire cardiac electrical signals from at least portions of at least one of the patient's torso 14 and the patient's heart 16; (b) data acquisition device 210 operably connected to the electrical sensing electrodes and configured to condition the cardiac electrical signals provided thereby; (c) scanner or imaging system 300 configured to generate patient geometry data, and (d) at least one non-transitory computer readable medium storing instructions executable by at least one processor configured to perform a method for receiving and processing the cardiac electrical signals and the patient geometry data in, for example, MMU 200 and first computer or computer workstation 250, PVM 400 and second computer or computer workstation 450, and/or in another suitable computing platform, whether local or remote, thereby to reconstruct the APs on a myocardial surface associated with the patient's heart and to provide on a display or monitor a real-time or near-real-time voxel-model-derived visual representation or image of the reconstructed APs and/or of the electrical activity of the patient's heart. The visual representations or images of the electrical activity of the patient's heart, endocardium, epicardium, or myocardium provided by EMS 10 can include epicardial or endocardial electrograms of a patient's heart, isopotential, isochronal maps of a model of a patient's heart, and/or dynamic or electrical wavefront propagation maps of a patient's heart, or other types of visualizations or images that can be generated by EMS 10. As described in further detail below, such visual representations of the electrical activity of a patient's heart may be provided in combination with EP mapping procedures carried out using EP catheter system 500, which may be configured to operate in conjunction with EMS 10.

Figure 12:
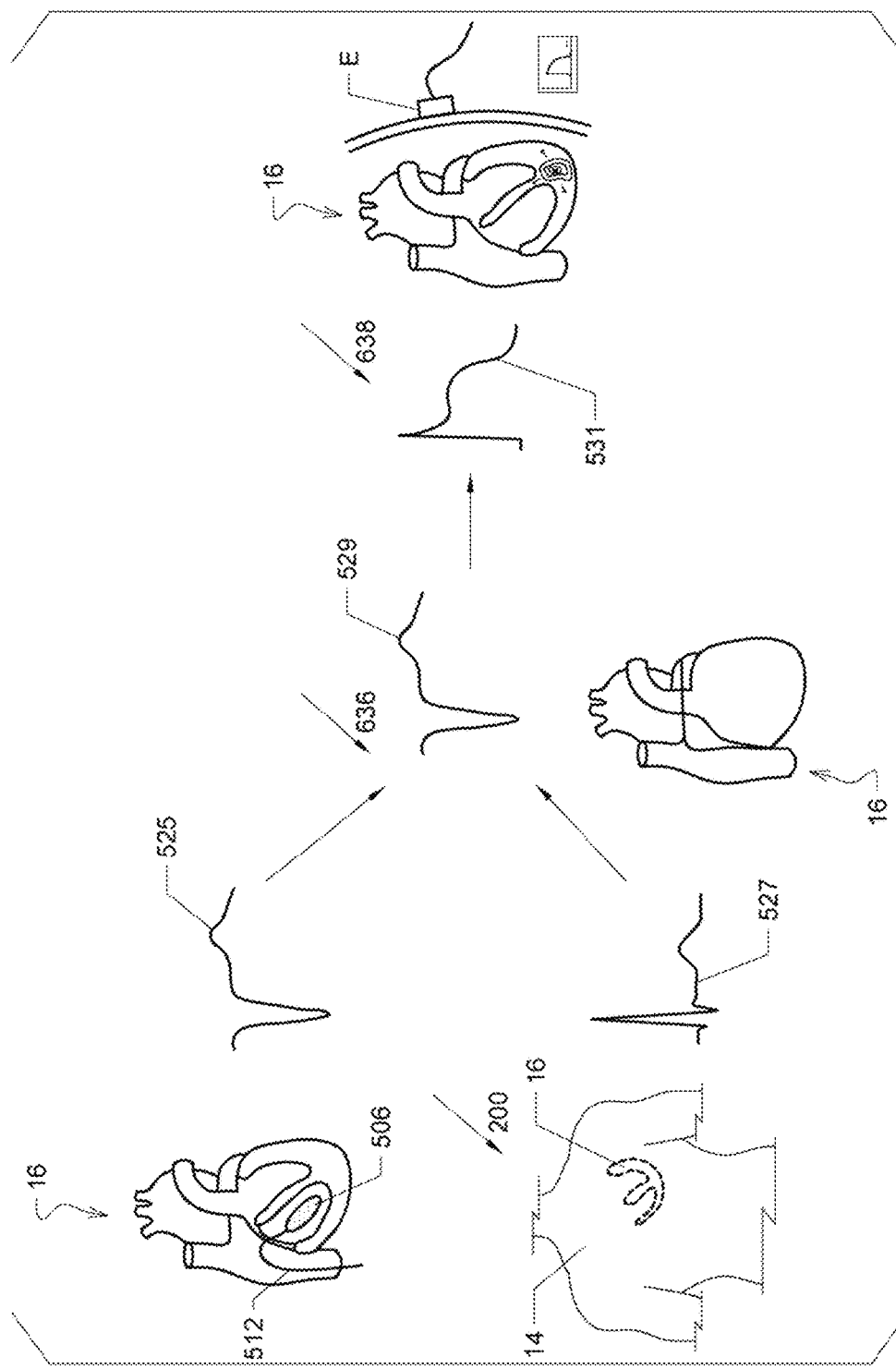
FIG. 12 shows illustrative representations of biophysical electrical signals that may be acquired and generated in the processing pipelines of some embodiments.

By way of non-limiting example, FIG. 12 shows illustrative representations of biophysical electrical signals that may be acquired and generated in the processing pipelines of FIGS. 10, 14(a), 14(b), 14(c), 15(a), 15(b) and 15(c). At the core of these figures are steps 636 and 638 of FIG. 10. In step 636, electrical potentials on the myocardial surface 529 are reconstructed from electrical potentials 525 on the surface of the heart 16 and/or from electrical potentials 527 on the surface of the torso 14 (ECG). In step 638, action potentials 531 are obtained from the previously reconstructed electrical potentials 529.

In the following paragraphs, a detailed description of the embodiments that illustrated in FIGS. 14(a), 14(b), 14(c), 15(a), 15(b) and 15(c) is provided, including descriptions of the mathematical frameworks that underlie these embodiments, or that may be used to realize such embodiments.

Mathematical Descriptions

Figure 13A:
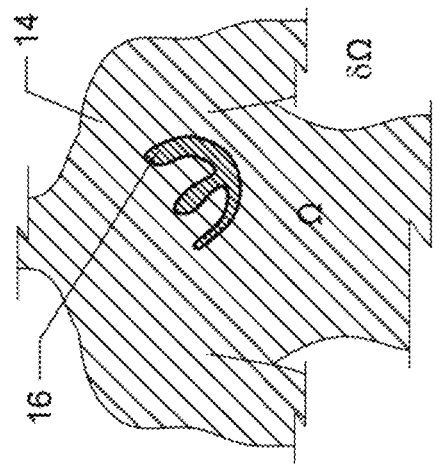
FIGS. 13(a) through 13(c) illustrate schematically representations of domains corresponding to the patient's torso 14 and heart 16 during different phases of data processing.
Figure 13B:
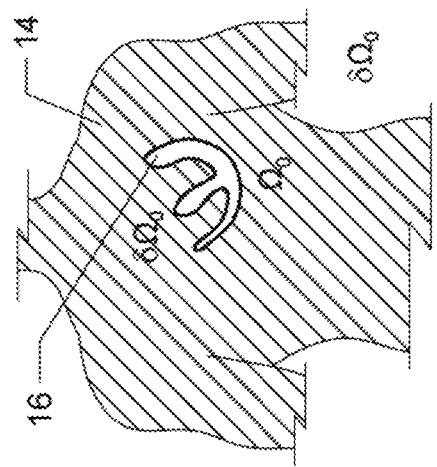
Figure 13C:
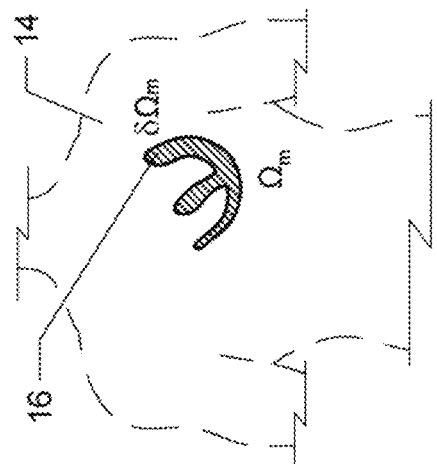

Referring now to FIGS. 13(a), 13(b) and 13(c), there are illustrated schematically representations of domains corresponding to the patient's torso 14 and heart 16 during different phases of data processing. The following definitions apply in the below description: Let $\Omega \subset R^3$ be a total domain of the human torso 14 and $\partial\Omega$ be its sufficiently smooth boundary; let $\Omega_m \subset \Omega$ be a domain of the myocardium 16 and $\partial\Omega_m$ be its sufficiently smooth boundary; let $\Omega_b = \Omega \backslash \Omega_m$ be a human torso domain without myocardium and $\partial\Omega_b$ be its sufficiently smooth boundary. Then, the boundary $\partial\Omega_b$ of the torso domain $\Omega_b$ consists of two disjoint parts: $\partial\Omega_b = \partial\Omega \cup \partial\Omega_m$.

According to the conventional bidomain model, the electrical activity of the heart is governed by the following equations and boundary conditions:

$$\nabla(\sigma_i(x) \cdot \nabla v(x,t)) + \nabla \cdot (\sigma_e(x)\nabla v(x,t)) = \chi\left(C_m \frac{\partial v(x,t)}{\partial t} + J_{ion}(x,t)\right), \quad (1)$$

$x \in \overline{\Omega}_m,$ $t \in [0, T]$ $$\nabla(\sigma_i \cdot \nabla v(x,t)) + \nabla((\sigma_i + \sigma_e) \cdot \nabla u_e(x,t)) = 0, x \in \overline{\Omega}_m, t \in [0,T] \quad (2)$$

$$v(x,t) = u_i(x,t) - u_e(x,t), x \in \overline{\Omega}_m, t \in [0,T] \quad (3)$$

$$\nabla(\sigma_b(x,t) \cdot \nabla u_b(x,t)) = 0, x \in \overline{\Omega}_b, t \in [0,T] \quad (4)$$

$$u_e(x,t) = u_b(x,t), x \in \partial\Omega_m, t \in [0,T] \quad (5)$$

$$n \cdot (\sigma_e(x) \cdot \nabla u_e(x,t)) = n \cdot (\sigma_b(x) \cdot \nabla u_b(x,t)), x \in \partial\Omega_m, t \in [0,T] \quad (6)$$

$$n \cdot (\sigma_i(x) \cdot \nabla v_i(x,t)) + n \cdot (\sigma_e(x) \cdot \nabla u_i(x,t)) = 0, x \in \partial\Omega_m, t \in [0,T] \quad (7)$$

$$n \cdot (\sigma_b(x) \cdot \nabla u_b(x,t)) = 0, x \in \partial\Omega, t = [0,T] \quad (8)$$

where $u_i$ is the intracellular electrical potential, $u_i$ is the extracellular electrical potential, v is the action potential (AP), $\chi$ is the membrane surface area per unit volume (of tissue), $C_m$ is the electrical capacitance of the cellular membrane per unit area, $J_{ion}$ is the ionic current over the membrane per unit area, $\sigma_i$, $\sigma_e$, $\sigma_b$ are the known intra-end extracellular and body tissues conductivity tensor matrices respectively, which may be assigned in step 630 and/or in step 636 and/or step 638 in FIG. 10 as electrical conductivity coefficients of at least one of the human torso and at least portions of the patient's myocardium to the geometric model calculated in step 630. Further, $x = (x_1, x_2, x_3)^T \in R^3$, t is a time, [0,T] is a time period, n is the unit co-normal vector to the surface, $\nabla$ is the del operator:

$$\nabla \equiv \left(\frac{\partial}{\partial x_1}, \frac{\partial}{\partial x_2}, \frac{\partial}{\partial x_3}\right)^T$$

We can reconstruct the AP in a given time moment $t_0$, so that we use only Eqs. (2) through (8). By way of non-limiting example, the basic idea of the disclosed embodiments of numerical reconstruction of the AP is the assumption that intracellular and extracellular electrical conductivity are isotropic. Given this assumption, the electrical conductivity values $\sigma_i$ and $\sigma_i$ not tensors, but scalars. Using this assumption, we can rewrite the expressions in Eq. (2) as follows:

$$\Delta(\sigma_i \cdot v(x)) + \Delta((\sigma_i + \sigma_e)) = 0, x \in \overline{\Omega}_m),$$

or $$\Delta(\sigma \cdot v(x) + u_e(x)) = 0, x \in \overline{\Omega}_m, \quad (9)$$

where $$\sigma = \frac{\sigma_i}{\sigma_i + \sigma_e}$$

and $\Delta$ is the Laplacian operator:

$$\nabla \equiv \left(\frac{\partial^2}{\partial x_1^2} + \frac{\partial}{\partial x_2^2}, \frac{\partial}{\partial x_3^2}\right)$$

Let us introduce a new function w(x), $x \in \overline{\Omega}_m$ such that $w(x)=\sigma \cdot v(x)+u_e(x)$. Using this function we can rewrite Eq. (9) as: $\Delta w(x)=0$, $x \in \overline{\Omega}_m$. Using boundary conditions expressed in Eqs. (6) and (7), we can represent the co-normal derivative of $w(x)$ on $\partial \Omega_m$ as follows:

$$n \cdot \nabla w(x) = \frac{\sigma_e}{\sigma_b}(1-\sigma) \cdot n \cdot \nabla u_b(x),$$
$$x \in \partial \Omega_m$$

Now, we can represent Eqs. (2) and (8) in the following form:

$$\Delta w = 0, x \in \overline{\Omega}_m, \quad (10)$$

$$n \cdot \nabla w(x) = \frac{\sigma_e}{\sigma_b}(1-\sigma) \cdot n \cdot \nabla u_b(x), x \in \partial \Omega_m \quad (11)$$

$$w(x) = \sigma \cdot v(x) + u_e(x) \quad (12)$$

$$\nabla(\sigma_b(x) \cdot \nabla u_b(x)) = 0, x \in \overline{\Omega}_b, \quad (13)$$

$$n \cdot (\sigma_b(x) \cdot \nabla u_b(x)) = 0, x \in \partial \Omega \quad (14)$$

The function w is a harmonic function, where w is governed by Laplace equation Eq. (10) in the domain $\Omega_m$ and by the Neumann boundary condition Eq. (11) on the surface $\partial \Omega_m$. Referring to FIG. 15(*a*), if co-normal derivatives $n \cdot \nabla u_b$ are known on the surface $\partial \Omega_m$ from preceding step 631 the function w can be found as a solution of the Neumann problem using the following Laplace equation:

$$\Delta w = 0, x \in \overline{\Omega}_m, \quad (15)$$

$$n \cdot \nabla w(x) = \frac{\sigma_e}{\sigma_b}(1-\sigma) \cdot n \cdot \nabla u_b(x), x \in \partial \Omega_m, \quad (16)$$

the solution of which is calculated in Step 639 of FIG. 15(*a*). Note that the solution of the Neumann problem is unique up to an additive constant. If the geometry of the myocardial domain is known, the Neumann problem for Laplace equations (15), (16) can be solved numerically using any conventional approach such as the finite element method (FEM) or the boundary element method (BEM). In the embodiment of FIG. 15(*a*), any of these methods can be used, based on pre-calculated linear operators and/or matrices (Step 635) and/or based on linear operators/matrices that are calculated from the heart geometry as obtained in step 633 as part of the reconstruction of action potentials Step 638. Note that no electrode positions and geometries of the torso may be required in steps 633 or 635). In one embodiment, Step 639 of FIG. 15(*a*) comprises using reconstructed electrical potential values and co-normal derivative values, and calculating harmonic function values in a myocardial domain by numerically solving the Neumann problem for the Laplace equation.

Next, in Step 643 of FIG. 15(*a*), we obtain the AP on the myocardial surface $\partial \Omega_m$ using the known values of $u_e$ from Step 627 and w from Step 639 by the formula following from Eq. (12):

$$v(x) = \frac{w(x) - u_e(x)}{\sigma} + const, x \in \partial \Omega_m \quad (17)$$

In one embodiment, Step 643 of FIG. 15(*a*) comprises using the harmonic function values of Step 639 of FIG. 15(*a*), the reconstructed electrical potential values of step 636 of FIG. 14(*a*), 14(*b*) or 14(*c*), and electrical conductivity coefficients as inputs, calculating, for at least portions of the myocardial surface, reconstructed action potential values representative of the APs.

Obtaining Co-Normal Derivatives of Electrical Potentials on the Myocardial Surface To compute the AP on the myocardial surface as described above and in FIG. 15(*a*), we need to know the values of electrical potentials and the values of their co-normal derivatives on the myocardial surface. If we have calculated the electrical potentials on the myocardial surface in step 636 and loaded them in step 627, we can obtain their co-normal derivatives using the following methodologies, which represent step 631 in FIG. 15(*a*), and which are further illustrated in FIGS. 15(*b*) and 15(*c*).

1. Known Torso Geometry and Heart and Torso Geometrical Relationships (See FIG. 15(*b*)).

Let us consider the function $u_e$, which is governed by the Laplace equation for inhomogeneous media (Eq. (14)) in the domain $\Omega_b$, and by the zero Neumann boundary condition (Eq. (16)) on the surface $\partial \Omega_m$. If the electrical potential $u_b$ is known on the surface $\partial \Omega_m$, its co-normal derivative $n \cdot \nabla u_b$ on $\partial \Omega_m$ can be found in step 645 as a solution of the following mixed boundary value problem:

$$\nabla(\sigma_b(x) \cdot \nabla u_b(x))=0, x \in \overline{\Omega}_b, \quad (18)$$

$$u_b(x)=f(x), x \in \partial \Omega_m, \quad (19)$$

$$n \cdot (\sigma_b(x) \cdot \nabla u_b(x))=0, x \in \partial \Omega, \quad (20)$$

where $f(x)$ is a known function.

If the geometry of the body domain $\Omega_b$ is known, the Neumann problem for Laplace equation Eqs. (15) and (16) can be solved numerically using any conventional approach such as the FEM or BEM, both of which are represented in FIG. 15(*b*) as variants of the illustrated embodiment, where the required linear operators and/or matrices can either be loaded from memory in Step 635, or where these operators and/or matrices can be calculated from the geometries of the torso and heart in step 633 (i.e., as part of the calculation of co-normal derivatives in step 631). The BEM solution of this problem is described below.

2. Unknown Torso Surface Geometry (See FIG. 15(*c*)).

Under the conditions established by Eqs. (10) through (14), the co-normal derivative of the cardiac electrical potential on the myocardial surface is a proportional to the surface Laplacian of the electrical potential as follows:

$$n \cdot \nabla u_b(x) = -4\Delta_s u_b(x), s \in \partial \Omega m, \quad (21)$$

where $\nabla_s$ is a surface Laplacian (i.e., Laplace-Beltrami operator on the myocardial surface). The surface Laplacian is defined as:

$$\Delta_s \equiv -\sum_{i,j} \frac{1}{\sqrt{g}} \frac{\partial}{\partial x_i}\left(g^{i,j}\sqrt{g}\frac{\partial}{\partial x_j}\right), i=1,2,$$

where $x_1$, $x_2$ are the local coordinates on a smooth 2D surface, and $g^{ij}$ are the components of the inverse of the metric tensor of the surface, $g = \det g^{ij}$.

An approximate calculation of the surface Laplacian values can be performed in step 649 after loading the triangular mesh of the respective surface in step 633 of FIG. 15(*c*), or it can be calculated, by way of non-limiting example, in step 634 of FIG. 10 using various numerical algorithms.

Thus, APs can be reconstructed from electrical potentials as follows:

1. Obtain the co-normal derivative of the electrical potential (step 631 in FIG. 15(*a*), two embodiments of which are illustrated in FIGS. 15(*b*), 15(*c*));
2. Obtain function w as a solution of the Neumann problem for the Laplace equations (15) and (16) (step 639 in FIG. 15(*a*)), and
3. Calculate APs using Eq. (17) (Step 643 in FIG. 15(*a*)).

In one embodiment of step 631, where the co-normal derivatives of electrical potentials on the myocardial surface are calculated, step 631 comprises using the cardiac electrical signals from step 624 and/or step 626, the geometric model from step 630, and the electrical conductivity coefficients from step 630 as inputs, and calculating reconstructed co-normal derivative values associated with the myocardial surface.

Referring now to FIG. 14(*a*), there is shown a method where cardiac surface electrical potentials are reconstructed based on measured body surface electrical potentials by solving the inverse problem of electrocardiography in terms of electrical potentials. Using Eqs. (13) and (14), the inverse problem of electrocardiography in terms of electrical potentials may be formulated as follows:

$$\nabla(\sigma_b(x)\cdot\nabla u_b(x))=0, x\in\overline{\Omega}_b, \tag{22}$$

$$n\cdot(\sigma_b(x)\cdot\nabla u_b(x))=0, x\in\partial\Omega \tag{23}$$

$$u(x)=f(x), x\in\partial\Omega, \tag{24}$$

where $f(x)$ is the measured body surface electrical potentials.

The problem posed by Eqs. (22) through (24) is solved in step 639 of FIG. 14(*a*). The Cauchy problem for elliptic equations is set forth in Eq. (22), which has a unique solution. Eq. (22) is ill-posed, however, and its numerical solution therefore requires the use of regularization algorithms.

Referring now to FIG. 14(*b*), one embodiment includes a method of AP reconstruction, where cardiac surface electrical potentials are measured via multi-electrode catheters on a part of the endocardial or epicardial surface of the heart.

In the case where cardiac surface electrical potentials are measured or reconstructed on the entire myocardial surface (as in Eqs. (22) through (24) and FIG. 14(*a*)), the reconstruction of APs includes the following steps illustrated in FIG. 15(*a*):

1. Step 631: Calculating the co-normal derivatives of electrical potentials on the myocardial surface using Eq. (21).
2. Step 639: Computing the function w by numerical solution in accordance with Eqs. (15) and (16) using FEM or BEM.
3. Step 643: Calculating the AP using Eq. (17).

Referring now to FIG. 14(*c*), when electrical potentials are measured on the body surface and on a portion of the endocardial and/or epicardial surfaces of the heart $\partial\Omega_1$, the method of reconstructing electrical potentials on the myocardial surface (step 639 in FIG. 14(*c*), which is part of step 636 in FIGS. 10 and 12) includes the following steps:

1. Calculating the co-normal derivative of the electrical potential on the myocardial surface using Eq. (21) on the portion of the cardiac surface where electrical potentials have been measured.
2. Obtaining the electrical potentials on that portion of the cardiac surface where electrical potentials were not measured by numerically solving the following problem:

$$\nabla(\sigma_b(x)\cdot\nabla u_b(x))=0, x\in\overline{\Omega}_b, \tag{25}$$

$$n\cdot(\sigma_b(x)\cdot\nabla u_b(x))=q, x\in\partial\Omega_1, \tag{26}$$

$$u(X)=f_1(X), x\in\partial\Omega_1 \tag{27}$$

$$n\cdot(\sigma_b(x)\cdot\nabla u_b(x))=0, x\in\partial\Omega \tag{28}$$

$$u(x)=\zeta(x), x\in\partial\Omega \tag{29}$$

where $\partial\Omega_1$ is the part of myocardial surface where the measuring of electrical potentials is available, $f_1$ is the electrical potentials measured on $\partial\Omega_1$, $g_1$ is the values of the co-normal derivative of the electrical potentials on $\partial\Omega_1$, calculated using $f_1$, $f$ is the measured body surface electrical potentials.

In general, this problem is also ill-posed and requires utilizing of regularization method for its solving. However, as in case of the embodiment shown in FIG. 14(*c*), electrical potentials recorded on a part of the heart increase significantly the accuracy of reconstruction of cardiac electrical activity.

Referring now to FIG. 14(*b*), when surface electrical potentials are measured on a portion of the endocardial and/or epicardial surface of the heart $\partial\Omega_1$, but if no such measurements are available from the body surface, in one embodiment the method of reconstructing electrical potentials on the myocardial surface (Step 639 in FIG. 14(*b*), which is part of Step 636 in FIGS. 10 and 12) includes the following steps:

1. Calculating the co-normal derivative of the electrical potential on the myocardial surface using Eq. (21) for the portion of the cardiac surface where electrical potentials have been measured.
2. Obtaining the electrical potentials on that portion of the cardiac surface where electrical potentials were not measured by numerically solving Eqs. (25)-(28), excluding the boundary condition (Eq. (29)).

Referring now to FIG. 15(*b*), which describes the calculation of co-normal derivatives of electrical potentials on the myocardial surface from electrical potentials on the myocardial surface, in one embodiment of step 645 the method includes solving the inverse problem of electrocardiography in terms of electrical potentials (see Eqs. 18 through 20), where relationships between cardiac surface electrical potentials and the normal derivatives of electrical potentials on the cardiac surface and body surface potentials are represented in the form of a system of two matrix equations, and where the system of matrix equations is solved using a special iterative procedure.

This method employs the assumption that the body electrical conductivity coefficient σ b is constant. In this case, Eq. (18) is a Laplace equation and the problem of Eqs. (22) through (24) may be rewritten as:

$$\Delta u_b=0, x\in\Omega_b, \tag{30}$$

$$n\cdot(\sigma_b(x)\cdot\nabla u_b(x))=0, x\in\partial\Omega \tag{31}$$

$$u(x)=f(x), x\in\partial\Omega, \tag{32}$$

Continuing to refer to the embodiment of step 645 in FIG. 15(*b*), to solve this problem (and by way of non-limiting example), we use the direct version of a BEM. This method is based on using Green's third identity:

$$\int_{\partial\Omega_b} n \cdot \nabla G(x,y) \cdot u_b(y) \, ds + 2\pi u_b - \int_{\partial\Omega_b} G(x,y) \cdot n \cdot \nabla u_b(y) \, ds = 0; \, x, y \in \partial\Omega_b \quad (32)$$

where $G(x,y)$ is a fundamental solution of the Laplace equation, and where:

$$G(x,y) = \frac{1}{|x-y|},$$

$|x-y| \equiv \sqrt{(x_1-y_1)^2+(x_2-y_2)^2+(x_3-y_3)^2}$ is a Euclidean distance between points x and y.

Writing Eq. (32) for the case where point x belongs to the surface $\Omega_m$ and where point x also belongs to the surface $\Omega$, and considering that the co-normal derivative of the electrical potential on the body surface $\Omega$ is equal to zero, we obtain the following system of linear integral equations:

$$\int_{\partial\Omega_m} n \cdot \nabla G(x,y) \cdot u_b(y) \, ds + \quad (33)$$

$$2\pi u_b(y) - \int_{\partial\Omega_m} G(x,y) n \cdot \nabla u_b(y) \, ds = $$

$$\int_{\partial\Omega} n \cdot \nabla G(x,z) \cdot f(z) \, ds, \, x \in \partial\Omega_m, \, y \in \partial\Omega_m, \, z \in \partial\Omega$$

$$\int_{\partial\Omega_m} n \cdot \nabla G(x,y) \cdot u_b(y) \, ds - \int_{\partial\Omega_m} G(x,y) \cdot n \cdot \nabla u_b(y) \, ds = \quad (34)$$

$$\int_{\partial\Omega} n \cdot \nabla G(x,y) \cdot f(z) \, ds + 2\pi f(z),$$

$$x \in \partial\Omega, \, y \in \partial\Omega_m, \, z = \partial\Omega$$

where the values of integrals in the right parts of the equations are known.

Next, we approximate the system of the linear integral by a system of matrix equations using the collocation or projection version of a BEM in the following form:

$$H_{mm} \cdot u - G_{mm} \cdot q = f_{mb} \quad (35)$$

$$H_{bm} \cdot u - G_{bm} \cdot q = f_{bb} \quad (36)$$

where $H_{mm}$, $H_{bm}$, $G_{mm}$, $G_{bm}$ are matrices and u, q, $f_{mb}$, $f_{bb}$ are vectors of corresponding dimensions obtained as BEM approximations of the respective integral operators, sought-for functions and known right-hand side functions.

In the embodiment of step 645 in FIG. 15(*b*), we use the following iterative procedure for solving the system of Eqs. (35) and (36):

$$q^{(0)} = q_0 \quad (37)$$

$$H_{mm} \cdot u^{(2i)} = G_{mm} \cdot q^{(2i-1)} + f_{mb} \quad (38)$$

$$G_{bm} \cdot q^{(2i+1)} = H_{bm} \cdot u^{(2i)} - f_{bb} \quad (39)$$

The matrix $H_{mm}$ is a well-conditioned matrix, and thus conventional approaches (such as LU-decomposition or QR decomposition) can be applied to solve Eq. (38). In contrast, $G_{bm}$ is an ill-conditioned matrix, so numerical solution of Eq. (39) requires the application of regularization methods.

By way of non-limiting example, the regularization technique of the embodiment of step 645 shown in FIG. 15(*b*) includes preconditioning the matrix equation and using a Tikhonov-type regularization method. Preconditioning allows the condition number of the matrix equation to be reduced. The method may be expressed by a preconditioned matrix equation:

$$P^{-1} \cdot G_{bm} \cdot q^{(2i+1)} = P^{-1}(H_{bm} \cdot u^{(2i)} - f_{bb})$$

instead of the original Eq. (39), where P is a well-conditioned matrix such that $P^{-1}G_{bm} \approx E$; E is the identity matrix. In one embodiment and by way of non-limiting example, the preconditioning matrix can be created by means of a truncated singular value decomposition of the matrix $G_{bm}$.

Let us consider the application of a Tikhonov-type regularization method, as in the above-described embodiment. To this end, we rewrite preconditioning Eq. (39) as:

$$M \cdot q = \varphi, \quad (40)$$

where $M = P^{-1} G_{bm}$, $q = q^{(2i+1)}$, $\varphi = P^{-1}(H_{bm} \cdot u^{(2i)} - f_{bb})$ Tikhonov-type regularization approaches can be introduced where the function $\|Mq-\varphi\|_{L2} + J(q)$ is formulated, where $J(q)$ is the Tikhonov stabilizing functional, and where the following optimization problem is solved:

$$q = \arg\min \|Mq-\varphi\|_{L2} + J(q), \text{ subject to } A_p \cdot q \leq 0, p=1,2, \quad (41)$$

where $A_p$ are matrices, used for establishing of optional inequality constraints.

By way of non-limiting example, one embodiment of step 645 in FIG. 15(*b*) may include using constraints established on the basis of the relationship between the AP and electrical potentials and/or further properties of the AP. In one embodiment, these constraints are used to introduce a priori information as part of solving equation Eq. (40) for the iterative procedure described in Eqs. (37) through (39) in the form of inequalities, and may help solve the inverse problem of electrocardiography with more accuracy.

By way of non-limiting example, the embodiment of step 645 shown in FIG. 15(*b*) may include the use of a priori information in accordance with the known electrophysiological fact that the action potential magnitude cannot exceed a predetermined value:

$$v_{rest} \leq v(t) \leq v_{max}, \text{ or}$$

$$v_{rest} + v(t) \leq 0 \quad (43)$$

$$v(t) - v_{max} \leq 0 \quad (44)$$

where $v_{rest} \approx -85$ mV is the resting potential, and $v_{max} \approx 30$ mV is the maximal value of the AP. Using this constraint, the optimization problem of Eq. (41) can be represented as:

$$q = \arg\min \|Mq-\varphi\|_{L2} + J(q), \text{ subject to } v_{rest} + A \cdot q \leq 0, Aq - v_{max} \leq 0, \quad (45)$$

where A is the matrix projecting the co-normal derivative of the electrical potential on the heart surface to the AP.

Continuing to refer to step 645 in FIG. 15(*b*), in another embodiment simplest form of stabilizing functional $J(q)$ is employed in Eq. (41):

$$J_1(q) = \alpha_1 \cdot \|Eq\|_{L2}, \quad (46)$$

where E is the identity matrix, and $\alpha_1 > 0$ is the regularization parameter. In this case the optimization problem represented by Eq. (40) (without inequality constraints) can be reduced to the matrix equation:

$$(M^T M + \alpha \cdot E) \cdot q = M^T \varphi. \quad (47)$$

By way of non-limiting example, in ne embodiment of step 645 in FIG. 15(*b*) may include using constraints established on the basis of the relationship between the AP and electrical potentials and/or further properties of the AP. In one embodiment, these constraints are used to introduce a priori information in Eq. (40) for the iterative procedures described by Eqs. (37) through (39) in form of a function, and may help to solve the inverse problem of electrocardiography with more accuracy.

The stabilizing functional J (q) may assume the following form:

$$J_2(q) = \alpha_2 \cdot \|v\|_{L1} = \alpha_2 \cdot \|A \cdot q\|_{L1}, \tag{48}$$

where A is the matrix projecting the co-normal derivative of electrical potentials on the heart surface to AP, $\alpha_1 > 0$ is the regularization parameter, and $\|\ldots\|_{L1}$ is the $L_1$ vector norm.

Some embodiments include using a priori information regarding the AP, and employ a rule that the module of the time derivative of the AP is proportional to the module of the AP gradient:

$$\frac{\partial v(x,t)}{\partial t} \approx k \cdot |\nabla v(x,t)|, x \in \partial\Omega_m \tag{49}$$

Using the simplest finite difference approximation of the AP time derivative, in one embodiment, and by way of non-limiting example, we can represent Eq. (49) as:

$$\frac{v(x,t_i) - v(x,t_{i-1})}{h} = k \cdot |\nabla v(x,t_{i-1})|$$

Thus, we can predict the current value of the AP by its value at time moment $t_{i-1}$ by the formula:

$$v(x,t_i) \approx v(x,t_{i-1}) + k \cdot \|\nabla v(x,t_{i-1})\| \cdot h \tag{50}$$

where $t_i$ and $t_{i-1}$ are the current and previous discrete time moments, $h = |t_i - t_{i-1}|$, k is a known coefficient depending on the conduction velocity of myocardial excitation.

Next, in one embodiment, we can obtain an a priori estimation of the co-normal derivative of electrical potentials on the myocardial surface using the following formula:

$$\bar{q} = A^{-1} v$$

In one embodiment, the gradient of the AP on the myocardial surface can be represented as a vector, one component of which is the co-normal derivative of the AP; the other two of which are the myocardial surface gradient. The normal derivative of the AP can be derived from the co-normal derivative of the electrical potential using the boundary conditions set forth in Eqs. (6) and (7); the surface gradient can be calculated numerically on a triangular cardiac surface mesh using, for example, the method described by Jyh-Yang Wu, Mei-Hsiu Chi and Sheng-Gwo Chen in "A local tangential lifting differential method for triangular meshes," 2010, vol. 80, issue 12, pages 2386-2402.

Further, in another embodiment of step 645 in FIG. 15(*b*), we can obtain an a priori estimation of the co-normal derivative of electrical potentials on the myocardial surface using the following formula:

$$\bar{q} = A^{-1} v$$

In one embodiment, by way of non-limiting example, the predicted value of the AP can be used as a priori information using Twomey regularization methods or Kalman filter approaches. Twomey regularization methods involve presenting the stabilization functional as an L2 norm of the difference between the a priori and the a posteriori estimation of the AP, which is multiplied by the weighting factor $\alpha_3$:

$$J_3(q) = \alpha_3 \cdot \|q - \bar{q}\|_{L2}, \tag{51}$$

where q is the predicted value of the AP.

In an embodiment that employs a Kalman filter approach, the calculations may be as follows (although other calculations using Kalman filtering may also be used):

$$q = \hat{q} + [(p)^{-1} + A^T(R)^{-1}A]^{-1} A^T(R)^{-1}(\varphi - A\hat{q}) \tag{52}$$

$$P_k = [(P)^{-1} + A^T(R)^{-1}A]^{-1}, \tag{53}$$

where P is the a posteriori error covariance matrix, and R is the covariance matrix of the data noise, which can be estimated from the body surface ECG.

Continuing to refer to step 645 in FIG. 15(*b*), the optimization problem of Eq. (41) (with stabilization functional $J_1$ and/or $J_3$ with constraints in the form of linear inequalities) can be reduced to a matrix equation. In one embodiment, the optimization problem of Eq. (41) includes constraints in form of linear inequalities and/or a solution stabilization functional $J_3$, which may be solved using conventional ways such as, by way of non-limiting example, a sequential quadratic programming approach.

By way of non-limiting example, in the aforementioned embodiments of step 645 in FIG. 15(*b*), the matrix A (which is related to the co-normal derivative of electrical potentials with action potentials) can be obtained by BEM as follows. First, we find the matrix of the Neumann-Dirichlet transformation, i.e., the matrix D that projects the co-normal derivatives of electrical potentials onto the myocardial surface, and the electrical the potentials onto the myocardial surface.

The boundary integral equations Eq. (33) and (34) can be represented in matrix form using BEM techniques is as follows:

$$H_{mm} \cdot u_m - G_{mn} \cdot q_m = H_{mb} u_b \tag{54}$$

$$H_{bm} \cdot u_m - G_{bm} \cdot q_m = H_{bb} u_b \tag{55}$$

where $H_{mm}$, $H_{bm}$, $G_{mm}$, $G_{bm}$ are matrices obtained as BEM approximations of the respective integral operators, and $u_m$, $u_b$, $q_m$ are vectors of corresponding dimensions obtained as BEM approximations of electrical potentials on the myocardial surface, and of electrical potentials on the body surface and as co-normal derivatives of electrical potentials on the myocardial surface.

Next, we express $u_b$ from Eq. (55) and substitute it into Eq. (54):

$$(H_{bb})^{-1}[H_{bm} \cdot u_m - G_{bm} \cdot q_m] = u_b$$

$$H_{mm} \cdot u_m - G_{mm} \cdot q_m = H_{mb} \cdot (H_{bb})^{-1}[H_{mb} \cdot u_m - G_{bm} \cdot q_m]$$

$$H_{mm} \cdot u_m - H_{mb} \cdot (H_{bb})^{-1} H_{mb} \cdot u_m = G_{mm} \cdot q_m - H_{mb} \cdot (H_{bb})^{-1} G_{bm} \cdot q_m$$

Thus, we obtain:

$$[H_{mm} - H_{mb} \cdot (H_{bb})^{-1} H_{mb}] \cdot u_m = [G_{mm} - H_{mb} \cdot (Hhd\ bb)^{-1} G_{bm}] \cdot q_m$$

$$u_m [H_{mm} - H_{mb} \cdot (H_{bb})^{-1} H_{mb}]^{-1} \cdot [G_{mm} - H_{mb} \cdot (Hhd\ bb)^{-1} G_{bm}] \cdot q_m$$

or $$u_m = D \cdot q_m \tag{56}$$

$$q_m = A^{-1} \cdot u_m \tag{57}$$

where $$D = [H_{mm} - H_{mb} \cdot (H_{bb})^{-1} H_{mb}]^{-1} \cdot [G_{mm} - H_{mb} \cdot (Hhd\ bb)^{-1} G_{bm}] \quad (58)$$

Next, and continuing to refer to the aforementioned embodiments of step 645 in FIG. 15(*b*), we find the matrix A, which relates to the co-normal derivatives of electrical potentials with action potentials by BEM representation. Using the third Green identity, the Neumann problem of Eqs. (15) and (16) can be represented in the form of the following boundary integral equation:

$$-\int_{\partial\Omega_m} n \cdot \nabla G(x, y) \cdot w(y) ds + 2\pi u_b(y) - \int_{\partial\Omega_m} G(x, y) \cdot n \cdot \nabla w(y) ds = 0$$

or $$-\int_{\partial\Omega_m} n \cdot \nabla G(x, y) \cdot w(y) ds +$$

$$2\pi u_b(y) - \frac{\sigma_e}{\sigma_b}(1 - \sigma) \int_{\partial\Omega_m} G(x, y) \cdot n \cdot \nabla u_b(y) ds = 0$$

Boundary integral equations Eq. (33) and (34) can be represented in matrix form using BEM techniques as follows:

$$\hat{H}_{mm} \cdot w + \frac{\sigma_e}{\sigma_i}(1 - \sigma) \cdot G_{mm} \cdot q_m = 0$$

where $\hat{H}_{mm}$, $G_{mm}$, are matrices obtained as BEM approximations of the respective integral operators, and w, $q_m$ are vectors of corresponding dimensions obtained as BEM approximations of action potentials on the myocardial surface, and of the co-normal derivatives of electrical potentials on the myocardial surface.

Thus, action potentials can be found using Eq. (17) as follows:

$$v = \frac{\sigma_e}{\sigma_i}(1 - \sigma) \cdot (\hat{H}_{mm})^{-1} G_{mm} \cdot q_m - u_m$$

Using Eq. (56), $$v = \frac{\sigma_e}{\sigma_i}(1 - \sigma) \cdot (\hat{H}_{mm})^{-1} G_{mm} \cdot q_m - D \cdot q_m$$

Thus, $$v = A \cdot q_m, \text{ and} \quad (59)$$

$$q_m = A^{-1} \cdot q_m \quad (60)$$

where $$A = \frac{\sigma_e}{\sigma_i}(1 - \sigma) \cdot (\hat{H}_{mm})^{-1} G_{mm} - D \quad (61)$$

Computer Algorithm Example

There is now described one embodiment of a computer algorithm and corresponding computer pseudo-code that find application in the various methods, systems, devices and components described herein. Table 1 below sets forth an example of representative computer pseudo-code.

Figure 18:
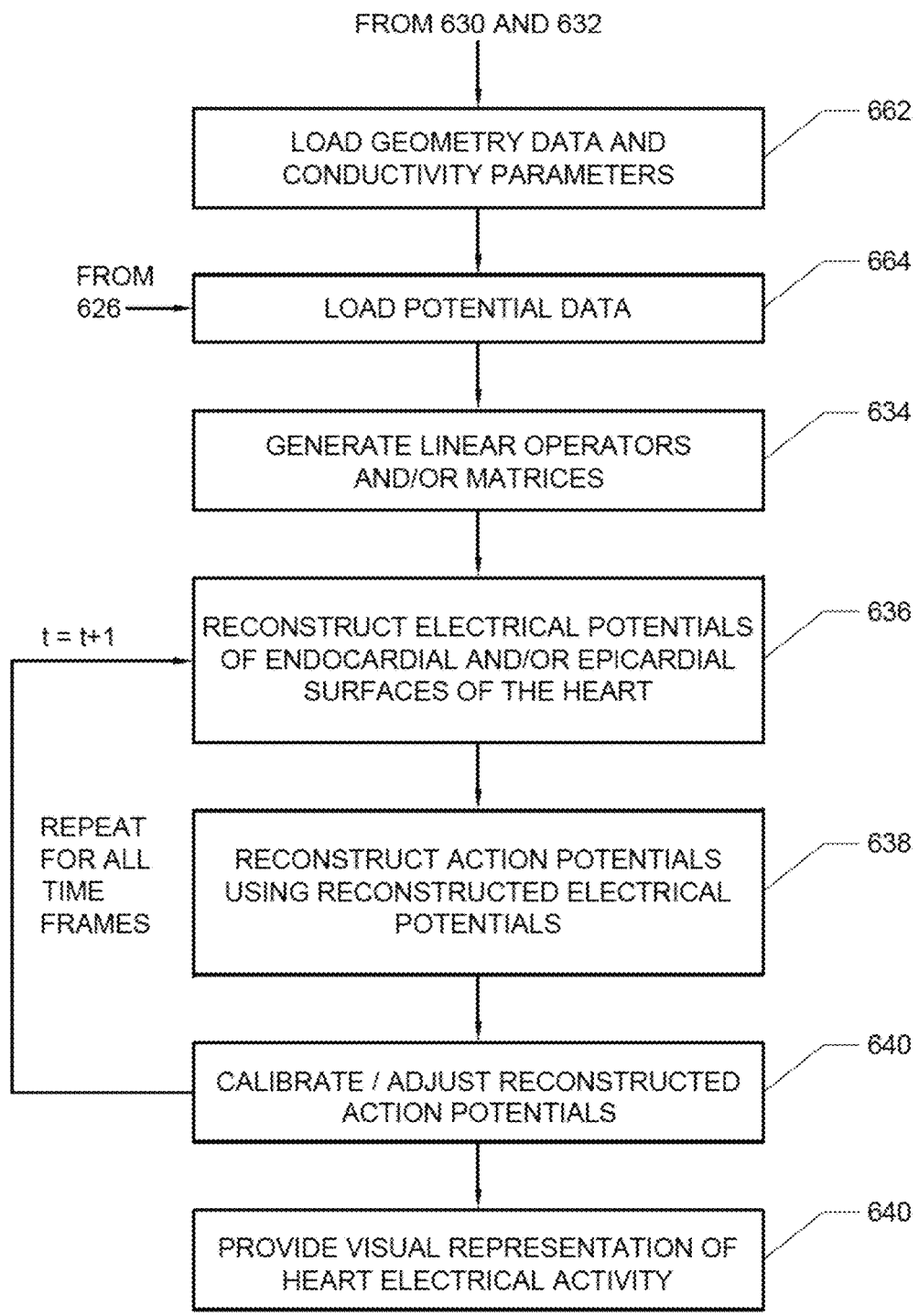
FIG. 18 shows one embodiment of a method associated with the computer algorithm and pseudo-code described in Table 1.

In one embodiment, and with reference to the computer pseudo-code of Table 1 below, steps 634, 636, 638, 640 and 642 of FIG. 10 are carried out by a computer program, which in one embodiment is stored on and executed by the computer of PVM 400/450. As illustrated in FIG. 18, the program initially loads geometry data corresponding to torso 14 and heart 16 from a storage device of the computer that has previously been generated in steps 630 and 632 of FIG. 10. The program then loads conductivity parameters for use in field calculations. Still referring to FIG. 18, the program subsequently loads potential data from the storage device of the computer that has previously been generated in Step 626 of FIG. 10. Next, and continuing to refer to FIG. 18, the program performs step 634 of FIG. 10, in which linear operators are generated from torso and heart geometry data. In particular, the tangential gradient is computed for the mesh nodes of the heart geometry. Matrices are prepared and stored in the computer memory for the inverse solution that reconstructs electrical potentials (which are employed in step 636 of FIG. 10 and FIG. 18) and for the inverse solution that reconstructs action potentials (which are employed in step 638 of FIG. 10 and FIG. 18). Steps 636, 638 and 640 of FIG. 10 are then repetitively performed to generate inverse solutions for all time frames associated with the potential data.

Continuing to refer to Table 1 and FIG. 18, as a first step in the loop, the Cauchy problem of Eqs. (22) through (24) is solved to obtain electrical potentials on the myocardial surface from body surface electrical potentials (which corresponds to step 639 of Step 636, as illustrated in FIG. 14(*a*)). Using the computer program of Table 1, linear operators are employed in an inverse solution that have previously been calculated in step 634, which are accessed in step 635 of Step 636 (see FIG. 14(*a*)).

Next, step 638 of FIG. 10 and FIG. 18 is performed in the continuing loop to reconstruct action potentials using the previously reconstructed electrical potentials, which is illustrated in detail in FIG. 15(*a*). As part of step 638, step 631 is initially performed, where the co-normal derivatives of the previously computed electrical potentials on the myocardial surface are calculated. In step 631, the embodiment of FIG. 15(*b*) is employed, where the inverse problem of Eqs. (18) through (20) in step 645 is solved, and where again linear operators are used in the inverse solution that have been pre-calculated in step 634 (which are accessed in step 635 of step 631; see FIG. 15(*b*)).

Next, and while still in step 638 of the continuing loop of FIG. 18, the Neumann problem represented by step 639 in FIG. 15(*a*) is solved to obtain the harmonic function w, and step 643 is performed to calculate action potentials from w and the previously computed co-normal derivatives of the electrical potentials (see FIG. 15(*a*)). The inverse solution function is executed and then also performs step 640 of FIG. 10 and FIG. 18 to correct the reconstructed action potentials (as illustrated in FIGS. 16(*a*) and 16(*b*)). Again, in the embodiment that is carried out using the computer program of Table 1, and that is illustrated in FIG. 18, linear operators are used in the inverse solution that have been pre-calculated in step 634 (which are accessed in step 635 of step 638; see FIG. 15(*a*)). Finally, the computer program of Table 1 then computes the gradient of the reconstructed action potentials for later use in visual representation of heart electrical activity in step 642.

Continuing to refer to the computer program of Table 1 and FIG. 18, once the loop has been run for all time frames of the potential data in an embodiment where step 640 is repetitively followed by step 636 and step 638 for a previously specified number of iterations, step 642 of FIG. 10 is performed such that a visual representation of heart electrical activity is provided. To this end, a time-dependent feature is calculated to represent the activation of the heart that is generated from the previously stored gradients of the reconstructed action potentials, which are normalized along the mesh nodes for each of the corresponding time frames. Further, in a graphical user interface on a display of PVM 400/450, a visual representation of heart electrical activity is then provided. Time-dependent features and reconstructed action potentials are visualized in conjunction with the heart geometry obtained in step 630, along with the acquired electrical potentials on the body, which together are visualized on the torso geometry obtained in step 630.

TABLE 1

Computer Pseudo-Code Example

```
def solve_ap(cfg):
    # load data
    print('Load data')
    print('---------')
    # load geometry data
    body = io.loadObj('{ }/body.obj'.format(cfg.patient_dir))
    heart = io.loadObj('{ }/heart.obj'.format(cfg.patient_dir))
    # load parameters
    tree = et.parsec('{ }/Parameters.xml'.format(cfg.patient_dir))
    sg_i = float(tree.find(
        'cp:Physiological/cp:IntracellularConductivities', ns).attrib['normal'])
    sg_e = float(tree.find(
        'cp:Physiological/cp:ExtracellularConductivities', ns).attrib['normal'])
    sg_b = float(tree.find('cp:Physiological/cp:BathConductivity', ns).text)
    sg_n = (sg_b - sg_e) / sg_i - 1
    # load potentials data
    ub = io.loadPotentials('{ }/ue/body.rte'.format(cfg.patient_dir))
    nV0 = body.v.shape[0]
    nTri0 = body.tri.shape[0]
    nV1 = heart.v.shape[0]
    nTri1 = heart.tri.shape[0]
    nFrames = ub.shape[1]
    print('Geometry:')
    print('    body: nV = {:d}, nTri = {:d}'.format(nV0, nTri0))
    print('    heart: nV = {:d}, nTri = {:d}'.format(nV1, nTri1))
    print('ECG:')
    print('    nFrames = {:d}'.format(nFrames))
    print('Conductivities:')
    print('    sg_i = {:.1f}, sg_e = {:.1f}, sg_b = {:.1f}'.format(sg_i, sg_e, sg_b))
    print('')
    # prepare linear operators
    body.calcGeometry(ndir = 'out')
    heart.calcGeometry(ndir = 'in')
    heart_G, heart_uv = gt.prepareGradLTL(heart)
    inv_solver = ipecg_tikh_i.Solver(cfg)
    inv_solver.prepareMatrices(body, heart, None)
    ap_solver = ipecg_ap.Solver(cfg)
    ap_solver.prepareMatrices(body, heart, (sg_i, sg_e, sg_b))
    # solve problem
    print('Solve problem')
    print('-------------')
    ue_chy = np.zeros((nV1, nFrames))
    ub_chy_mix = np.zeros((nV0, nFrames))
    qe_chy_mix = np.zeros((nV1, nFrames))
    v_nm = np.zeros((nV1, nFrames))
    v_nm_grad = np.zeros((nV1, nFrames, 3))
    # solve for all time frames of the potentials data
    for i in range(nFrames):
        # solve Cauchy problem
        ue_chy[:, i:i+1] = inv_solver.solve(ub[:, i:i+1])
        # get co-normal derivative
```

TABLE 1-continued

Computer Pseudo-Code Example

```
        (ub_chy_mix[:, i:i+1], qe_chy_mix[:, i:i+1] =
            inv_solver.getMixed(ue_chy[:, i:i+1]))
        # solve Neumann problem, get action potential and fix constant
        v_nm[:, i:i+1] = ap_solver.solve(ub[:, i:i+1], ue_chy[:, i:i+1])
        # compute gradient
        v_nm_grad_t = gt.getGradLTL(heart, heart_G, heart_uv,
            v_nm[:, i:i+1])
        v_nm_grad[:, i] = v_nm_grad_t
    print('Calculate activations')
    v_nm_act = np.zeros((nV1, nFrames))
    for i in range(nFrames):
        v_nm_act[:, i:i+1] = la.seq_norm(v_nm_grad[:, i])
    print('')
    print('Show results')
    print('-------------')
    map_view1 = MapView.QtView(MapView.Model(body, heart, ub,
                               np.hstack((v_nm_act, v_nm))))
    map_view1.show()
def main():
    import config as cfg
    solve_ap(cfg)
if __name__ == '__main__':
    main()
```

Figure 16A:
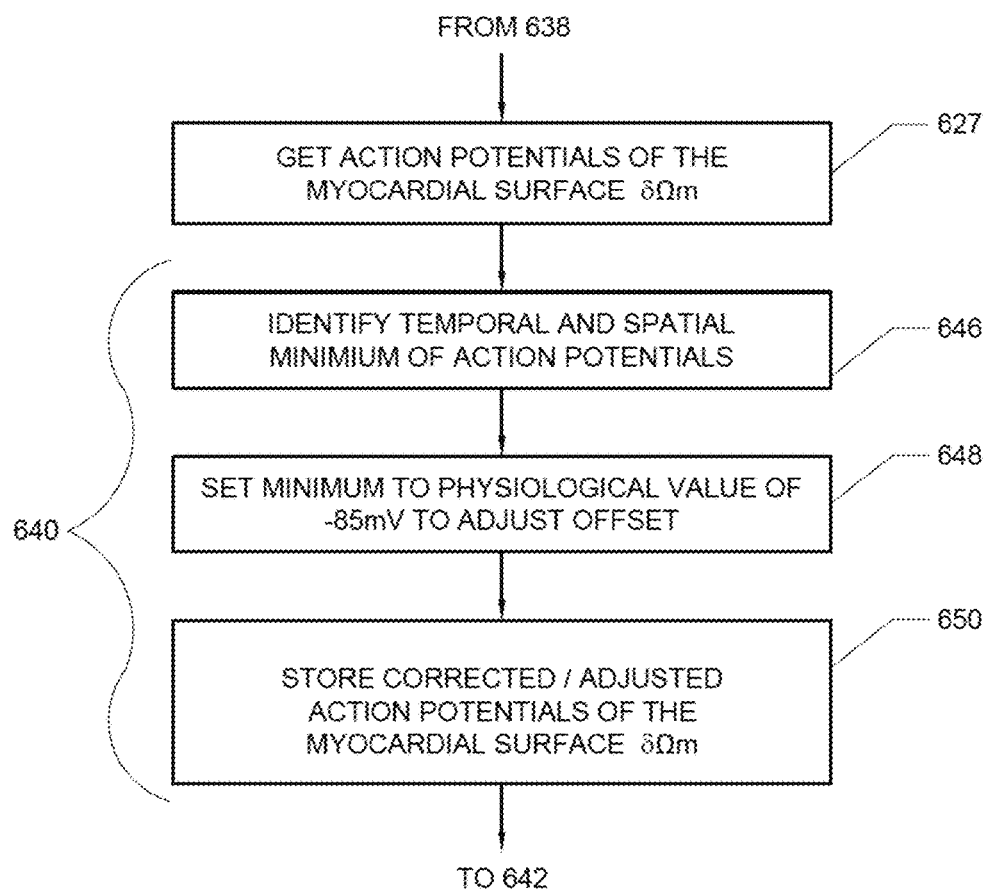
FIGS. 16(a) and 16(b) illustrate one embodiment of corrected and adjusted action potentials.
Figure 16B:
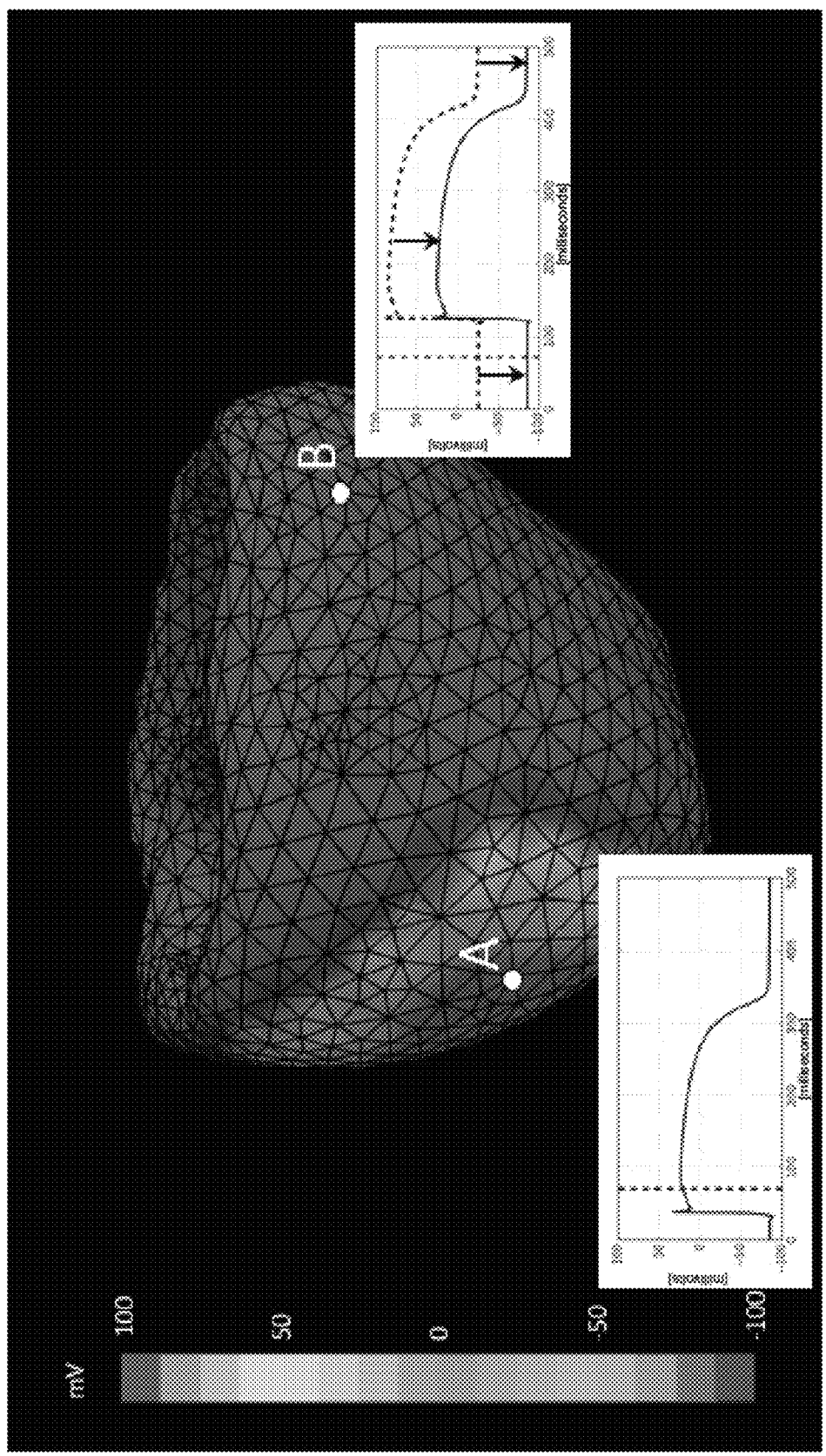

Referring now to FIGS. 16(a) and 16(b), there are shown examples of numerically reconstructed APs containing an arbitrary additive constant. This constant is the same for AP values in all cardiac surface points at a given moment in time, but may differ at different moments in time. To determine the arbitrary additive constant, we use the well-known fact in cardiac cellular electrophysiology that the APs at the all points of an unexcited zone of the myocardium have an identical or near-identical minimal known value, which is called the resting potential.

A method of determining the exact value of the AP without the use of an arbitrary additive constant includes the following steps (see FIGS. 16(a) and 16(b)):

1. Obtaining the AP on the myocardial surface (step 627).

2. Identifying the spatial minimum of the APs in each time frame (step 646).

3. Setting the spatial minimum to a physiological value of $v_{resting} \approx 85$ mV that adjusts the offset in the APs appropriately (step 648).

The foregoing method is applicable in the case where at least one small area of the myocardium is in an unexcited state. To control this condition, we use the activation and recovery sequences obtained from the AP gradient. Note that the AP gradient does not contain the arbitrary additive constant because a gradient of a constant is equal to zero.

FIGS. 16(a) and 16(b) illustrate calibration and adjustment of the AP. FIG. 16(a) shows a flow chart illustrating one embodiment of such a calibration and adjustment. FIG. 16(b) shows distribution of the AP at a moment in time when point A is in the excited zone of the myocardium, and when point B is in the unexcited zone. The value of the AP in point B is equal to the known resting AP. Thus, we can use the pre-computed value of the AP at point B to adjust the reconstructed AP.

Figure 17A:
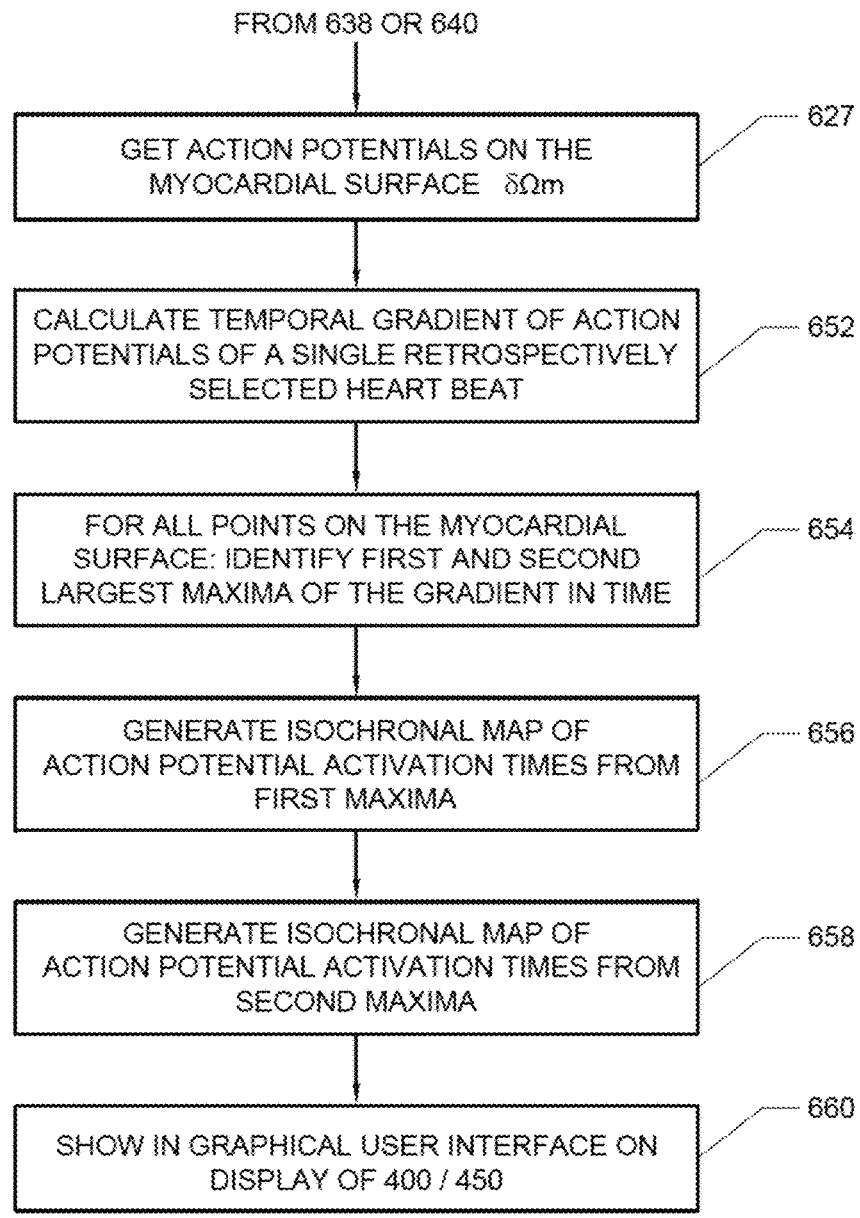
FIG. 17(a) illustrates one embodiment of a method of visualizing heart electrical activity.
Figure 17B:
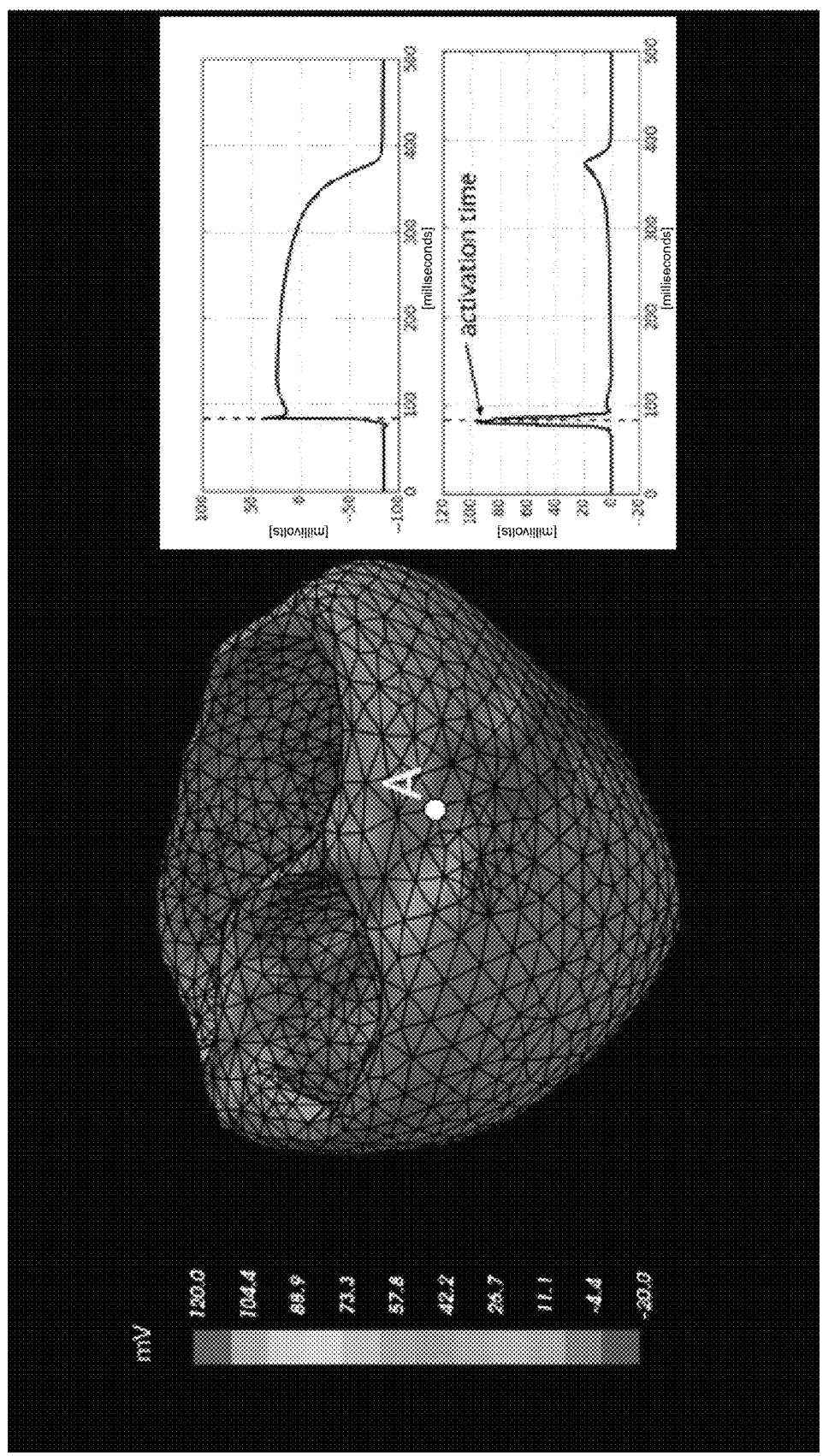
FIGS. 17(b) and 17(c) show some embodiments of visual representations associated with the method of FIG. 17(a)
Figure 17C:
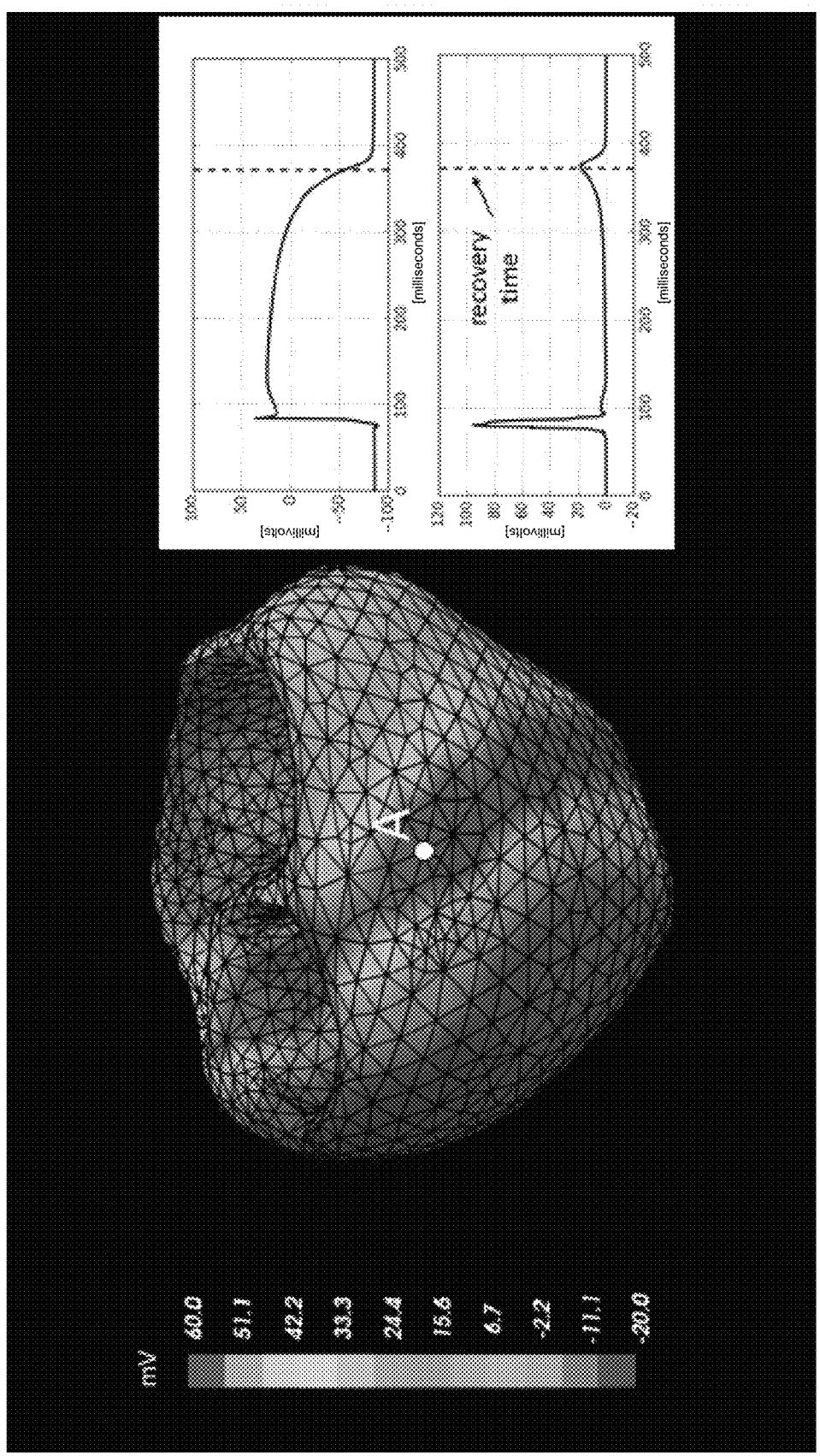

Referring now to FIGS. 17(a) through 17(c), in one embodiment of Step 642 in FIG. 10 there is provided a method of reconstructing sequences of myocardial depolarization (activation) and repolarization (recovery), and of providing graphical representations of such information in the form of isochronal maps.

In FIG. 17(a), and in some embodiments, such a method may include the steps of:
1. Obtaining the AP on the myocardial surface (step 627).
2. Calculating the AP temporal gradient and/or the AP gradient modulus as a function of time in each mesh node of the heart for a single retrospectively selected heart beat (step 652).
3. Detecting the first and second largest local maxima of the gradients in time for all nodes of the myocardial surface mesh (step 654). (The first maxima observed during the depolarization period are associated with the starting of the myocardial activation (see FIG. 17 (b)). The second maxima observed at the repolarization period are associated with the starting of the myocardial recovery process—see FIG. 17 (c)).
4. Obtaining activation times (step 656) and recovery times (step 658) as the times corresponding to the first and the second local AP gradient maxima, respectively, according to the following formula:

$$\tau_a(x_i) = \mathrm{argmax}_{t,} |\nabla v(x_i, t)|, t \in [0, T_D]$$

$$\tau_r(x_i) = \mathrm{argmax}_{t,} |\nabla v(x_i, t)|, t \in [T_D, T_R],$$

Where $x_i$ is a mesh node, i=1, 2, . . . , t is a time, $\tau_a$ is an activation time, $\tau_r$ is a recovery time, $|\nabla v(x_i,t)|$ is an AP gradient, $[0,T_D]$ is a depolarization period, and $[T_D,T_R]$ is a repolarization period.
5. Continuing to refer to steps 656 and 658, the gradient of the AP on the myocardial surface may be represented as a vector, one component of which is the co-normal derivative of the AP; the other two are the myocardial surface gradient. The normal derivative of AP can be derived from the co-normal derivative of the electrical potential using boundary conditions (Eqs. (6) and (7). The surface gradient can be calculated numerically on a triangular cardiac surface mesh using, for example, the method described above by Jyh-Yang Wu et al.
6. Visualizing the sequence of cardiac activation and recovery on the cardiac surface (step 660) using pre-calculated activation and recovery times in the mesh nodes using the conventional computer graphics means (such as an Open GL library).

Referring again to FIG. 17(a), there are shown reconstruction steps and the visualization of sequences of the cardiac depolarization and repolarization processes based on computed APs.

Referring also again to FIG. 17 (b), there is shown the determination of an activation time at a given point on the cardiac surface using the AP gradient. FIG. 17(b) shows the distribution of the AP gradient modulus on the surface of the heart ventricles at the moment when excitation signals arrive at point A. The upper plot presents the AP as a function of time at point A, while the lower plot represents the AP gradient as a function of time at point A. The first maximum of the AP gradient corresponds to the moment of myocardial activation at point A.

FIG. 17(c) shows the determination of the recovery time at a given point on the cardiac surface using the AP gradient. FIG. 17(c) demonstrates the distribution of the AP gradient modulus on the surface of the heart ventricles at the moment when excitation signals arrive at point A. The upper plot represents the AP as a function of time at point A, while the lower plot represents the AP gradient as a function of time at point A. The first maximum of the AP gradient corresponds to the moment of myocardial activation at point A.

In a different embodiment of Step 642 in FIG. 10, there is provided a method of visualizing and/or identifying myocardial fibrosis areas. This method is based on the fact that an regions exhibiting myocardial fibrosis on a patient's heart will be electrically non-conductive or of low conductivity. Thus, the AP gradient in such regions will be equal to zero or of small magnitude. Such a method includes the following steps:
1. Reconstruction of the AP gradient on the myocardial surface during the repolarization period of the cardiac cycle.
2. Determination of the minimal and the maximal values of the AP during the selected time period, and calculation of the magnitude of the AP at each node of the heart surface.
3. Depicting the AP magnitude as an AP voltage map on a display of PVM 400/450 using color encoding.
4. Classifying myocardial areas in which the AP magnitude is below a specified threshold as areas or regions of fibrosis.

Figure 19:
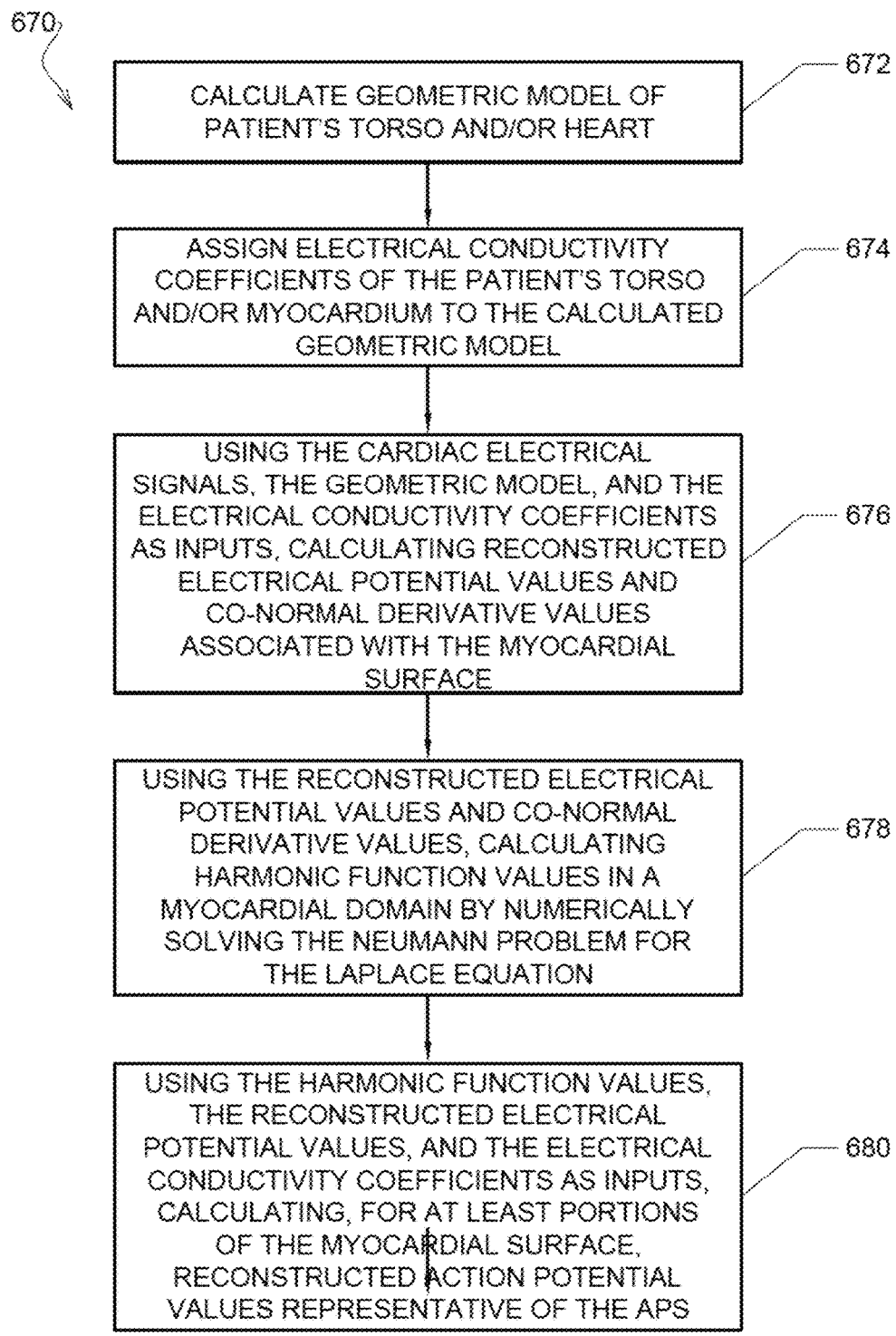
FIG. 19 shows one embodiment of a generalized method of generating reconstructed action potential values.

Referring now to FIG. 19, there is shown one embodiment of a generalized method of generating reconstructing action potential values, which may be employed after the pertinent cardiac electrical signals and imaging data have been obtained. Method 670 of FIG. 19 includes step 672, where a geometric model of the patient's torso and/or heart is calculated. At step 674, electrical conductivity coefficients of the patient's torso and/or myocardium are assigned to the calculated geometric model. At step 676, and using the cardiac electrical signals, the geometric model, and the electrical conductivity coefficients as inputs, reconstructed electrical potential values and co-normal derivative values associated with the myocardial surface are calculated. At step 678, and using the reconstructed electrical potential values and co-normal derivative values, harmonic function values in a myocardial domain are calculated by numerically solving the Neumann problem for the Laplace equation. At step 680, and using the harmonic function values, the reconstructed electrical potential values, and the electrical conductivity coefficients as inputs, for at least portions of the myocardial surface, reconstructed action potential values representative of the APs are calculated.

Figure 20:
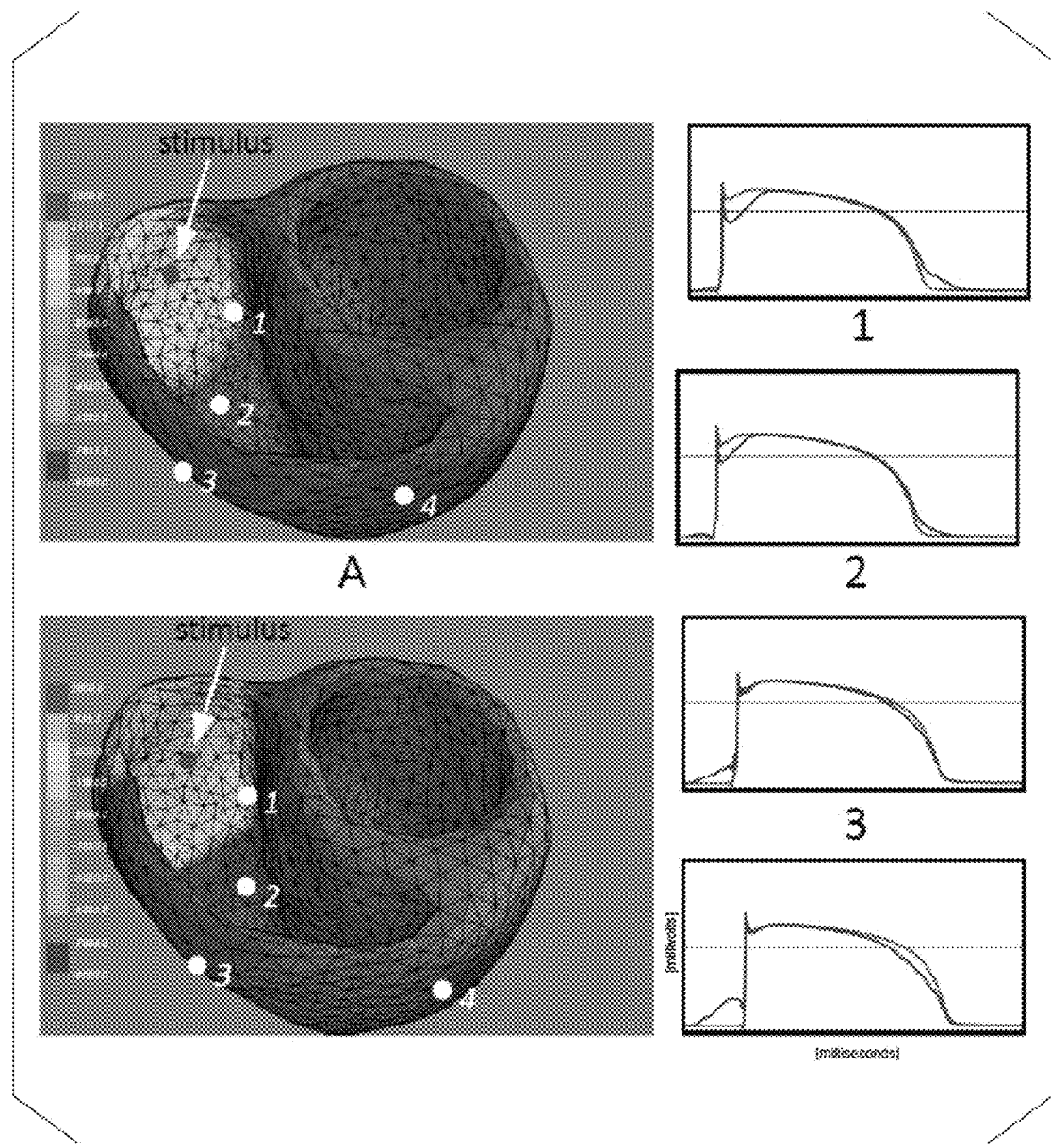
FIG. 20 provides an illustration of the performance of some of the methods disclosed and described herein.

FIG. 20 provides an illustration of the performance of some of methods disclosed and described herein. In FIG. 20, true action potentials are illustrated on a computer model of the heart in (A), and reconstructed action potentials (obtained using the inverse solution) are illustrated on the model of the heart in (B). The time courses of the true action potentials as well as the time courses of the inverse solutions are illustrated for points 1-4 on the model of the heart.

Continuing to refer to FIG. 20, true action potentials are generated using numerical simulations. These are based on virtual pacing methodology. To perform these simulations, we took the geometry of the human torso and ventricles as they were reconstructed from CT data using a method that is equivalent to step 630 in FIG. 10. Next, we applied virtual stimuli at arbitrary points of the ventricles and solved the forward problem to obtain electrical potentials on the body surface. Finally, we added noise to the forward solution and solved the following problems:

Reconstructing heart extracellular potentials from body surface potentials as obtained in the forward calculation (step 636 in FIG. 10), and Reconstructing action potentials from heart extracellular potentials (step 638 in FIG. 10).

For numerical simulations and inverse solutions, we used an isotropic model of the solution domain. Simulations were obtained using the Oxford Cardiac Chaste Modeling Tool using the Bidomain-With-Baths formulation of the problem. We used a realistic anatomy of the human heart that was obtained in a volume segmentation approach, and employed further in the Tusscher-Noble and Noble-Panfilov (TNNP) cell model. Inverse solutions were obtained using an implementation of the pseudo-code set forth in Table 1.

In view of the structural and functional descriptions provided herein, those skilled in the art will appreciate that portions of the described devices and methods may be configured as methods, data processing systems, or computer algorithms. Accordingly, these portions of the devices and methods described herein may take the form of a hardware embodiment, a software embodiment, or an embodiment combining software and hardware, such as shown and described with respect to the computer system of FIG. 21. Furthermore, portions of the devices and methods described herein may be a computer algorithm stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, systems, and computer algorithm products. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct a computer or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the an individual block, plurality of blocks, or block diagram.

Figure 21:
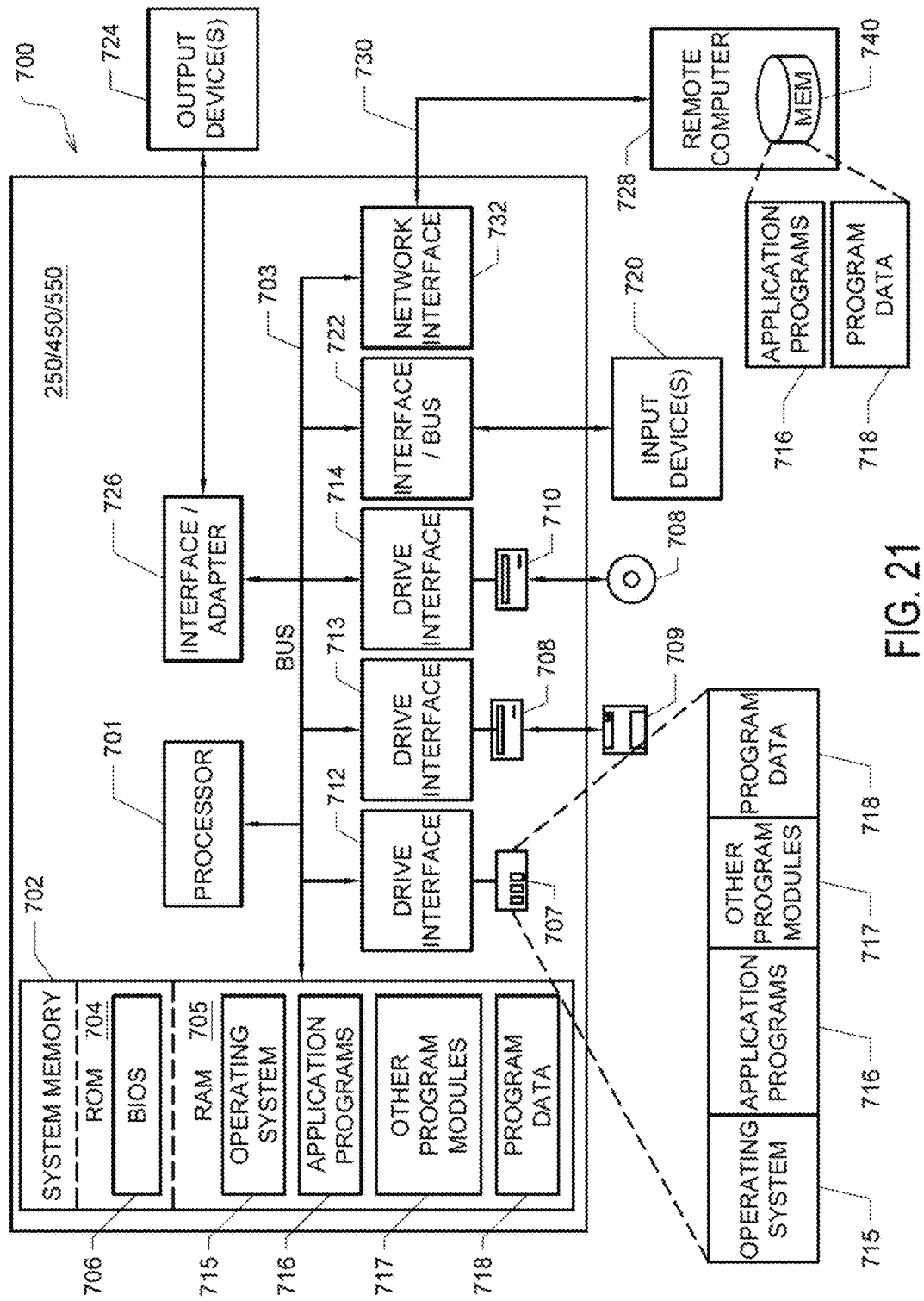
FIG. 21 shows one embodiment of a computer system 700.

In this regard, FIG. 21 illustrates only one example of a computer system 700 (which, by way of example, can be first computer or computer workstation 250, second computer or computer workstation 450, third computer of EP catheter system 500, or any combination of the foregoing computers or computer workstations) that can be employed to execute one or more embodiments of the devices and methods described and disclosed herein, such as devices and methods configured to acquire and process sensor data, to process image data, and/or transform sensor data and image data associated with the analysis of cardiac electrical activity and the carrying out of the combined electrophysiological mapping and analysis of the patient's heart 16. Continuing to refer to FIG. 21, computer system 700 can be implemented on one or more general purpose computer systems or networked computer systems, embedded computer systems, routers, switches, server devices, client devices, various intermediate devices/nodes or standalone computer systems. Additionally, computer system 700 or portions thereof may be implemented on various mobile devices such as, for example, a personal digital assistant (PDA), a laptop computer and the like, provided the mobile device includes sufficient processing capabilities to perform the required functionality.

In one embodiment, computer system 700 includes processing unit 701 (which may comprise a CPU, controller, microcontroller, processor, microprocessor or any other suitable processing device), system memory 702, and system bus 703 that operably connects various system components, including the system memory, to processing unit 701. Multiple processors and other multi-processor architectures also can be used to form processing unit 701. System bus 703 can comprise any of several types of suitable bus architectures, including a memory bus or memory controller, a peripheral bus, or a local bus. System memory 702 can include read only memory (ROM) 704 and random access memory (RAM) 705. A basic input/output system (BIOS) 706 can be stored in ROM 704 and contain basic routines configured to transfer information and/or data among the various elements within computer system 700.

Computer system 700 of FIG. 21 can include a hard disk drive 707, a magnetic disk drive 708 (e.g., to read from or write to removable disk 709), or an optical disk drive 710 (e.g., for reading CD-ROM disk 711 or to read from or write to other optical media). Hard disk drive 707, magnetic disk drive 708, and optical disk drive 710 are connected to system bus 703 by a hard disk drive interface 712, a magnetic disk drive interface 713, and an optical drive interface 714, respectively. The drives and their associated computer-readable media are configured to provide nonvolatile storage of data, data structures, and computer-executable instructions for computer system 700. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the devices and methods described and disclosed herein.

A number of program modules may be stored in drives and RAM 707, including operating system 715, one or more application programs 716, other program modules 717, and program data 718. The application programs and program data can include functions and methods programmed to acquire, process and display electrical data from one or more sensors, such as shown and described herein. The application programs and program data can include functions and methods programmed and configured to process data acquired from a patient for assessing heart function and/or for determining parameters for delivering a therapy, such as shown and described herein with respect to FIGS. 1-20 and Table 1.

A health care provider or other user may enter commands and information into computer system 700 through one or more input devices 720, such as a pointing device (e.g., a mouse, a touch screen, etc.), a keyboard, a microphone, a joystick, a game pad, a scanner, and the like. For example, the user can employ input device 720 to edit or modify the data being input into a data processing algorithm (e.g., only data corresponding to certain time intervals). These and other input devices 720 may be connected to processing unit 701 through a corresponding input device interface or port 722 that is operably coupled to the system bus, but may be connected by other interfaces or ports, such as a parallel port, a serial port, or a universal serial bus (USB). One or more output devices 724 (e.g., display, a monitor, a printer, a projector, or other type of display device) may also be operably connected to system bus 703 via interface 726, such as through a video adapter.

Computer system 700 may operate in a networked environment employing logical connections to one or more remote computers, such as remote computer 728. Remote computer 728 may be a workstation, a computer system, a router, a network node, and may include connections to many or all the elements described relative to computer system 700. The logical connections, schematically indicated at 330, can include a local area network (LAN) and/or a wide area network (WAN).

When used in a LAN networking environment, computer system 700 can be connected to a local network through a network interface or adapter 732. When used in a WAN networking environment, computer system 700 may include a modem, or may be connected to a communications server on the LAN. The modem, which may be internal or external, can be connected to system bus 703 via an appropriate port interface. In a networked environment, application programs 716 or program data 718 depicted relative to computer system 700, or portions thereof, may be stored in a remote memory storage device 740.

What have been described above are examples and embodiments of the devices and methods described and disclosed herein. It is, of course, not possible to describe every conceivable combination of components or methodologies for purposes of describing the invention, but one of ordinary skill in the art will recognize that many further combinations and permutations of the devices and methods described and disclosed herein are possible. Accordingly, the devices and methods described and disclosed herein are intended to embrace all such alterations, modifications and variations that fall within the scope of the appended claims. In the claims, unless otherwise indicated, the article "a" is to refer to "one or more than one."

The foregoing outlines features of several embodiments so that those skilled in the art may better understand the detailed description set forth herein. Those skilled in the art will now understand that many different permutations, combinations and variations of hearing aid 10 fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems in the use of electrophysiological mapping systems.

We claim:

1. An electrophysiological mapping system (EMS) configured to reconstruct myocardial surface action potentials (APs) corresponding to a patient's heart, comprising:
   (a) a plurality of electrical sensing electrodes configured to acquire cardiac electrical signals from at least portions of at least one of the patient's torso and the patient's heart;
   (b) a data acquisition device operably connected to the electrical sensing electrodes and configured to condition the cardiac electrical signals provided thereby;
   (c) an imaging system configured to generate patient geometry data, and
   (d) at least one non-transitory computer readable medium storing instructions executable by at least one processor configured to perform a method for receiving and processing the cardiac electrical signals and the patient geometry data to reconstruct the APs on a myocardial surface associated with the patient's heart, wherein the method comprises: (i) calculating a geometric model of at least one of portions of the patient's torso and portions of the patient's heart; (ii) assigning electrical conductivity coefficients of at least one the patient's torso and at least portions of the patient's myocardium to the calculated geometric model; (iii) using the cardiac electrical signals, the geometric model, and the electrical conductivity coefficients as inputs, calculating reconstructed electrical potential values and co-normal derivative values associated with the myocardial surface; (iv) using the reconstructed electrical potential values and co-normal derivative values, calculating harmonic function values in a myocardial domain by numerically solving the Neumann problem for the Laplace equation; and (v) using the harmonic function values, the reconstructed electrical potential values, and the electrical conductivity coefficients as inputs, calculating, for at least portions of the myocardial surface, reconstructed action potential values representative of the APs.

2. The EMS of claim 1, wherein the electrical conductivity coefficients correspond to myocardial extracellular and intracellular media.

3. The EMS of claim 1, wherein the action potential values are further obtained by subtracting the electrical potential values from the harmonic function values, and dividing the results by a coefficient which is ratio of the values of the electrical conductivity coefficients.

4. The EMS of claim 1, wherein at least some of the cardiac electrical signals are provided by surface electrodes configured to provide ECGs.

5. The EMS of claim 1, wherein at least some of the cardiac electrical signals are provided by electrodes forming a portion of an Electrophysiology (EP) catheter.

6. The EMS of claim 3, wherein the EP catheter comprises a balloon and the electrodes are non-contact electrodes configured to float within the patient's blood within the patient's heart.

7. The EMS of claim 1, wherein the reconstructed action potential values are calculated using the geometry of the heart only.

8. The EMS of claim 1, wherein the reconstructed action potential values are calculated numerically using a boundary element method.

9. The EMS of claim 1, wherein the reconstructed action potential values are calculated numerically using a finite element method.

10. The EMS of claim 1, wherein the imaging system comprises a CT, MRI or MRT.

11. The EMS of claim 1, wherein the reconstructed action potential values are calibrated and adjusted according to a determined resting potential of the patient's myocardium.

12. The EMS of claim 1, wherein the method further comprises reconstructing a sequence of cardiac activation and recovery by calculating a gradient on the myocardial surface corresponding to the reconstructed action potential values.

13. The EMS of claim 1, wherein the method further comprises identifying regions of myocardial fibrosis in the patient's heart in which magnitudes of the reconstructed action potential values fall below a predetermined threshold.

14. A non-transitory computer-readable medium comprising instructions which, when executed by a computer system, cause the computer system to carry out a method of reconstructing myocardial surface action potentials (APs) corresponding to a patient's heart including the following steps: (a) acquiring a plurality of cardiac electrical signals from at least portions of at least one of the patient's torso and the patient's heart;
  (b) acquiring patient geometry data from the patient;
  (c) calculating a geometric model of at least one of portions of the patient's torso and portions of the patient's heart;
  (d) assigning electrical conductivity coefficients of at least one of the patient's torso and at least portions of the patient's myocardium to the calculated geometric model;
  (e) using the cardiac electrical signals, the geometric model, and the electrical conductivity coefficients as inputs, calculating reconstructed electrical potential values and co-normal derivative values associated with the myocardial surface;
  (f) using the reconstructed electrical potential values and co-normal derivative values, calculating harmonic function values in a myocardial domain by numerically solving the Neumann problem for the Laplace equation, and
  (g) using the harmonic function values, the reconstructed electrical potential values, and the electrical conductivity coefficients as inputs, calculating, for at least portions of the myocardial surface, reconstructed action potential values representative of the APs.

15. The non-transitory computer-readable medium of claim 14, including further instructions, which, when executed by a computer system, cause the computer system to acquire at least some of the cardiac electrical signals using surface electrodes configured to provide ECGs.

16. The non-transitory computer-readable medium of claim 14, including further instructions, which, when executed by a computer system, cause the computer system to acquire at least some of the cardiac electrical signals using electrodes forming a portion of an EP catheter.

17. The non-transitory computer-readable medium of claim 16, wherein the EP catheter comprises a balloon and at least some of the electrodes are non-contact electrodes configured to float within the patient's blood and heart.

18. The non-transitory computer-readable medium of claim 14, including further instructions, which, when executed by a computer system, cause the computer system calculate reconstructed action potential values using the geometry of the heart only.

19. The non-transitory computer-readable medium of claim 14, including further instructions, which, when executed by a computer system, cause the computer system to calculate the reconstructed action potential values numerically using a boundary element method.

20. The non-transitory computer-readable medium of claim 14, including further instructions, which, when executed by a computer system, cause the computer system to calculate the reconstructed action potential values numerically using the finite element method.

21. The non-transitory computer-readable medium of claim 14, wherein the step of acquiring patient geometry data comprises using an imaging system that includes a CT, MRI or MRT device.

22. The non-transitory computer-readable medium of claim 14, including further instructions, which, when executed by a computer system, cause the computer system to calibrate and adjust the reconstructed action potential values according to a determined resting potential of the patient's myocardium.

23. The non-transitory computer-readable medium of claim 14, including further instructions, which, when executed by a computer system, cause the computer system to calculate a sequence of cardiac activation and recovery by calculating a gradient on the myocardial surface corresponding to the reconstructed action potential values.

24. The non-transitory computer-readable medium of claim 14, including further instructions, which, when executed by a computer system, cause the computer system to identify regions of myocardial fibrosis in the patient's heart in which magnitudes of the reconstructed action potential values fall below a predetermined threshold.

* * * * *